(12) United States Patent
Han et al.

(10) Patent No.: US 9,518,263 B2
(45) Date of Patent: *Dec. 13, 2016

(54) SIGNAL ACTIVATED RNA INTERFERENCE

(71) Applicant: CALIFORNIA INSTITUTE OF TECHNOLOGY, Pasadena, CA (US)

(72) Inventors: Si-ping Han, Yorba Linda, CA (US); Robert D. Barish, Pasadena, CA (US); William A. Goddard, III, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,256

(22) Filed: Apr. 20, 2015

(65) Prior Publication Data

US 2016/0046934 A1     Feb. 18, 2016

Related U.S. Application Data

(63) Continuation of application No. 12/316,372, filed on Dec. 10, 2008, now Pat. No. 9,029,524.

(60) Provisional application No. 61/007,004, filed on Dec. 10, 2007, provisional application No. 61/063,604, filed on Feb. 5, 2008.

(51) Int. Cl.
*C12N 15/113* (2010.01)
*C07H 21/02* (2006.01)
*C12N 15/11* (2006.01)

(52) U.S. Cl.
CPC ............. *C12N 15/113* (2013.01); *C07H 21/02* (2013.01); *C12N 15/111* (2013.01); *C12N 2310/11* (2013.01); *C12N 2310/14* (2013.01); *C12N 2310/141* (2013.01); *C12N 2310/3517* (2013.01); *C12N 2310/3519* (2013.01); *C12N 2310/53* (2013.01); *C12N 2320/10* (2013.01)

(58) Field of Classification Search
CPC ...................... C12N 15/113; C12N 2310/3519
See application file for complete search history.

(56) References Cited

U.S. PATENT DOCUMENTS 9,029,524 B2 *   5/2015   Han ....................... C07H 21/02
                                                    536/24.5

* cited by examiner

*Primary Examiner* — Jon E Angell
(74) *Attorney, Agent, or Firm* — Steinfl & Bruno, LLP

(57) ABSTRACT

The invention provides compositions and methods for signal activated RNA interference (saRNAi), preferably in vivo. The invention provides polynucleotides that switches between an inactive form and an active form upon covalent or non-covalent interaction with one or more specific chemical signals, such as disease-specific mRNA, miRNA, or other cellular RNA products with sequences that characterize diseased states of the cell. The interaction between the subject polynucleotides and the signals is preferably mediated by hybridization, which exposes, facilitates the formation, and/or allows the formation of a substrate that can be processed by proteins of the RNAi pathway (such as Dicer). The input and output of multiple different polynucleotides of the invention can form an in vivo signaling network. In addition, the multiple input signals can be integrated to modulate the activity of the subject polynucleotides.

25 Claims, 33 Drawing Sheets

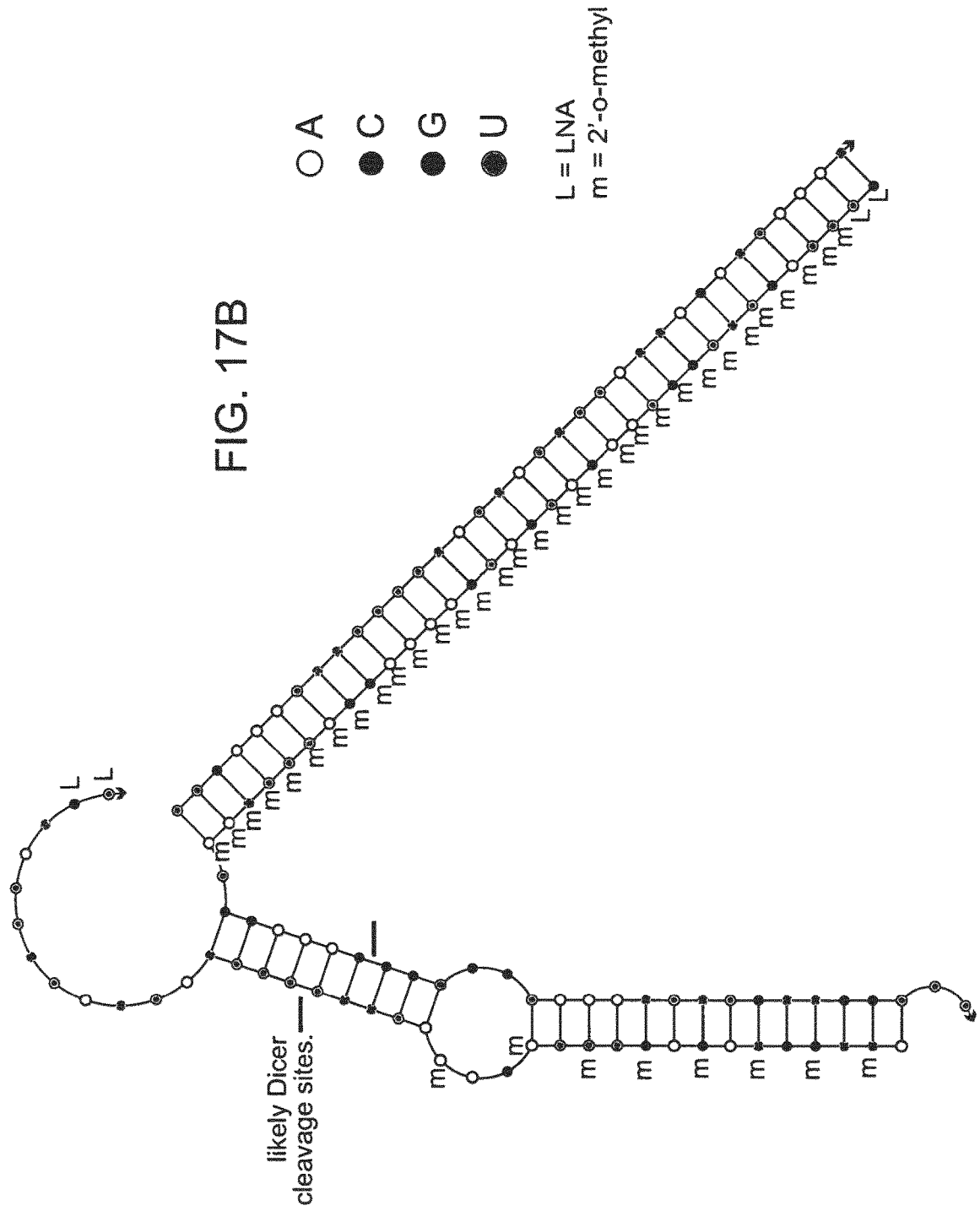

SIGNAL ACTIVATED RNA INTERFERENCE

REFERENCE TO RELATED APPLICATIONS

This application is a continuation of U.S. patent application Ser. No. 12/316,372, filed on Dec. 10, 2008, which, in turn, claims the benefit of the filing dates under 35 U.S.C. 119(e) of U.S. Provisional Applications 61/007,004, filed on Dec. 10, 2007, and 61/063,604, filed on Feb. 5, 2008, the entire contents of which, including all drawings, are incorporated herein by reference.

GOVERNMENT SUPPORT

The U.S. Government has certain rights in this invention pursuant to Grant No. CTS0608889 awarded by National Science Foundation (NSF).

BACKGROUND OF THE INVENTION

RNA interference (RNAi) has recently emerged as a promising new avenue for treating a wide range of disease conditions. However, there are a few practical problems associated with the use of RNAi as an effective therapeutic method.

One potential problem is that the repression of a disease associated mRNA is often insufficient to treat the disease itself. For example, the Panc-1 and Mia-Paca mutant forms of K-Ras are associated with more than 95% of pancreatic cancers. However, repression of either mutant gene is insufficient for killing the cancer cell (Fleming et al., *Molecular Cancer Research* 3: 413, 2005). An alternative strategy might involve repression of normal mRNAs that cancer cells up-regulate for proliferation. However, much like chemotherapy, this may cause non-specific harms to healthy cells and tissues, thus necessitating the delivery of RNAi complexes at a lower potency that may give cancer cells an opportunity to evolve drug resistance.

Another example is the treatment of nuclear integrating viruses such as HIV. While RNA interference may be able to temporarily stop viral replication by repressing key viral mRNAs, the presence of pro-viral DNA in the nucleus of long lived latent cells means that viral mRNAs could reemerge to reinitiate replication once treatment stops.

In addition, RNA interference often has side effects associated with the non-specific repression of mRNAs with partial sequence homology to the intended target ("off-target effect"). This problem could occur when multiple mRNAs in the same cell all have 3'-UTR regions susceptible to miRNAs targeted at one particular mRNA. In this case, attempt to inhibit the expression of one specific target gene could lead to simultaneous expression knock-down of others unintended targets in both diseased and healthy cells. This problem could also occur when a disease mRNA target is a close homolog of a wild type, as in, for example, single nucleotide polymorphisms. In this case, healthy cells may have their mRNAs repressed by RNA interference intended to target mutant genes.

Yet another problem frequently associated with RNAi therapy is the recognition of double stranded RNA structures by cellular immunity. Proteins associated with cellular immunity, such as Toll Like Receptors (TLR), duplex RNA binding protein kinases, Rig1 and others, could lead to apoptosis, interferon production, inducement of inflammation and other side effects in the presence of long stretch of double-stranded RNAs.

SUMMARY OF THE INVENTION

In one aspect, the invention provides a signal-activated polynucleotide construct, comprising: (1) a guide sequence and a sense sequence capable of forming a duplex region that can either become or be cleaved by Dicer to generate an siRNA or an miRNA comprising the guide sequence, wherein the guide sequence is substantially complementary to a transcript of a target gene; and, (2) a signal detecting sequence capable of hybridizing with either: (a) one or more signal polynucleotides, or, (b) one or more regions comprising part of the guide sequence and/or part of the sense sequence; wherein, (i) in the absence of the signal polynucleotides, the signal detecting sequence hybridizes with the one or more regions comprising part of the guide sequence and/or part of the sense sequence, wherein generation of the siRNA or miRNA is inhibited, and/or productive incorporation of the siRNA or miRNA into RISC is inhibited; (ii) in the presence of the signal polynucleotides, the signal detecting sequence hybridizes with the signal polynucleotides, and allows the formation of the duplex region for the generation of the siRNA or the miRNA.

In certain embodiments, in the absence of the signal polynucleotides, generation of the siRNA or miRNA and/or productive incorporation of the siRNA or miRNA into RISC is inhibited by at least about 2-fold (i.e., to 50%), 5-fold (i.e., to 20%), 10-fold (i.e., to 10%), or 20-fold (i.e., to 5%) or more.

In certain embodiments, the conformation of the construct in the absence of the signal polynucleotides is at least about 5 kcal/mole, preferably at least about 10 kcal/mole, lower in free energy at 37° C. in physiological conditions than the conformation in the presence of the signal polynucleotides.

In certain embodiments, the signal-activated polynucleotide construct comprises two or more single-stranded polynucleotides.

In certain embodiments, the nucleotides with chemical modifications, if any, are largely/mostly present on one or more the single-stranded polynucleotides.

In certain embodiments, the signal-activated polynucleotide is not activated in the absence of the signal polynucleotides when one or more the single-stranded polynucleotides are removed from the construct.

In certain embodiments, two or more of the single-stranded polynucleotides are covalently linked by a linker moiety (such as PEG) or a bond other than canonical polynucleotide linkage.

In certain embodiments, only one 5'-end and one 3'-end within the signal-activated polynucleotide construct is compatible for Dicer cleavage and RISC incorporation.

In certain embodiments, in the absence of the signal polynucleotides, the guide sequence and the sense sequence form a short duplex region of no more than 19 base pairs in length.

In certain embodiments, the short duplex region is about 16 base pairs in length.

In certain embodiments, the short duplex region is more than 11 base pairs in length.

In certain embodiments, the short duplex region comprises one or more chemical modifications that confer resistance to nuclease degradation.

In certain embodiments, in the absence of the signal polynucleotides, the guide sequence and the sense sequence form a double-stranded region comprising one or more chemical modifications that inhibits Dicer cleavage (e.g., modification at or around the Dicer cleavage site) and/or productive RISC incorporation.

In certain embodiments, the part of the guide sequence and the part of the sense sequence, when forming part of the duplex region, comprises one or more mismatched base pairs.

In certain embodiments, the part of the guide sequence is a continuous stretch of about 3 nucleotides or less.

In certain embodiments, the part of the sense sequence is a continuous stretch of about 5 nucleotides or less.

In certain embodiments, the guide sequence comprises a 2-nucleotide 3' overhang.

In certain embodiments, in the presence of the signal polynucleotides, an extension duplex region extends the duplex region formed by the guide sequence and the sense sequence.

In certain embodiments, each strand in the extension duplex region comprises about 7 nucleotides.

In certain embodiments, the extension duplex region comprises one or more mismatches.

In certain embodiments, in the absence of the signal polynucleotides, a first part of the signal detecting sequence hybridizes with the region comprising the part of the guide sequence to form a first additional duplex region.

In certain embodiments, a second part of the signal detecting sequence hybridizes with the regions comprising the part of the sense sequence to form a second additional duplex region.

In certain embodiments, neither the first additional duplex region nor the second additional duplex region triggers PKR-response in a mammalian cell.

In certain embodiments, the first additional duplex region and the second additional duplex region are each, independently, about 9, 10, 11, or 12 base pairs in length.

In certain embodiments, the guide sequence and the sense sequence form a short duplex region of no more than 19 base pairs in length, and wherein the combined length of any two of the short duplex region, the first additional duplex region, and the second additional duplex region is no more than 29 base pairs in length.

In certain embodiments, the first additional duplex region and/or the second additional duplex region are more than 20 base pairs in length, and comprise wobble base pairing or mismatch in every 4-8 nucleotides.

In certain embodiments, the wobble base pairing or mismatch is created by substituting U for C and/or G for A.

In certain embodiments, the signal-activated polynucleotide construct further comprises one or more 2'-o-methyl modifications that inhibit PKR and/or TLR activation.

In certain embodiments, the signal-activated polynucleotide construct further comprises one or more single-stranded segments and/or additional duplexes around: (1) the three-way junction region, (2) the first additional duplex region, and/or (3) the second additional duplex region.

In certain embodiments, the single-stranded segments and/or additional duplexes comprise non-canonical base-pairings or chelation of poly-valent cations.

In certain embodiments, one end of the first additional duplex region comprises a first unstructured single-stranded region.

In certain embodiments, one end of the second additional duplex region comprises a second unstructured single-stranded region.

In certain embodiments, the first and second unstructured single-stranded regions each comprise about 20 nucleotides.

In certain embodiments, the first unstructured single-stranded region and/or the second unstructured single-stranded region comprise modified bases that inhibit endonuclease (such as RNase A) degradation.

In certain embodiments, the signal detection sequence comprises one or more deoxyribonucleotides or chemically modified ribonucleotides.

In certain embodiments, the chemically modified ribonucleotides have one or more modifications on the ribose sugar ring, the phosphodiester backbone, and/or the base.

In certain embodiments, the chemically modified ribonucleotides have one or more attached bulky chemical groups or polymer molecules.

In certain embodiments, the signal-activated polynucleotide construct comprises one or more chemical modifications that are largely/mostly present on the sense sequence but are absent on the guide sequence.

In certain embodiments, the signal detecting sequence comprise one or more chemical modifications that promote hybridization between the signal detection sequence and the signal polynucleotides.

In certain embodiments, the signal-activated polynucleotide construct comprises one or more chemical modifications that facilitate the delivery of the construct.

In certain embodiments, the chemical modifications enhance non-covalent association with one or more of: cholesterol, antibody, nanoparticle, polymer, dendrimer, liposome, protein, and viral envelop.

In certain embodiments, the chemical modifications comprise chemical attachments to a 5'-end, an 3'-end, or an internal nucleotide of the construct.

In certain embodiments, the non-covalent association comprises one or more of electrostatic attraction, attachment via salt bridges, hydrogen bonds, polyion-condensation and charge inversion, van der Waals interactions, and hydrophobic/hydrophilic interactions.

In certain embodiments, the signal polynucleotides comprise an mRNA, an miRNA, an siRNA, a ribozyme, or a non-coding RNA.

In certain embodiments, the signal polynucleotides comprise two independent/unrelated signal polynucleotides.

In certain embodiments, at least one of the signal polynucleotides is not a transcript of the target gene.

In certain embodiments, the target gene is a wild-type gene with normal expression.

In certain embodiments, the mRNA is not a transcript of the target gene.

In certain embodiments, the mRNA is a transcript of the target gene.

In certain embodiments, the signal polynucleotides are within a 3'-UTR region.

In certain embodiments, the signal polynucleotides are substantially free of (significant) secondary structures.

In certain embodiments, the signal polynucleotides are within an evolutionary conserved site for miRNA binding.

In certain embodiments, the signal polynucleotides are calculated to lack sequence identity with other sequences in the human genome.

In certain embodiments, the signal polynucleotides comprise mutations associated with a disease or cellular process.

In certain embodiments, the sequence of the signal detecting sequence is adjusted to achieve optimal (not necessarily the maximum) level of hybridization with the signal sequence.

In certain embodiments, the guide sequence of the siRNA or miRNA is adjusted to achieve optimal (not necessarily the maximum) level of hybridization with the target gene transcript.

In certain embodiments, the signal detecting sequence hybridizes with the one or more regions comprising part of the guide sequence and part of the sense sequence, and comprises a 3-4 nucleotide single-stranded region between the sequences that hybridize to the part of the guide sequence and the part of the sense sequence.

In certain embodiments, two or more signal polynucleotides bind simultaneously or sequentially to different portions of the signal detecting sequence.

In certain embodiments, the presence of at least two of the signal polynucleotides are required for the generation of the siRNA or miRNA.

In certain embodiments, the presence of one of the two or more signal polynucleotides is sufficient for the generation of the siRNA or miRNA.

In certain embodiments, (i) in the absence of the signal polynucleotides, the signal detecting sequence hybridizes with the one or more regions comprising part of the guide sequence and part of the sense sequence to create two additional duplex regions, wherein one of the additional duplex regions is linked to a single-stranded loop with a nuclease-resistant sequence, and the other the additional duplex regions is linked to a hairpin structure comprising two DNA segments, one on each strand of the hairpin structure, wherein the two DNA segments base pair with each other at about 2 nucleotides; (ii) in the presence of the signal polynucleotides, the signal detecting sequence hybridizes with the signal polynucleotides, and disrupts the base pairing between the two DNA segments so as to allow RNase H to cleave an RNA sequence hybridized to one or both of the DNA segments.

In one aspect, the invention provides a signal-activated polynucleotide construct, comprising: (1) a guide sequence and a sense sequence capable of forming either an siRNA or an miRNA comprising the guide sequence, or a duplex region that can be cleaved by Dicer to generate the siRNA or miRNA, wherein the guide sequence is substantially complementary to a transcript of a target gene; (2) a blocking sequence capable of hybridizing with one or more regions comprising part of the guide sequence and/or part of the sense sequence; and, (3) one or more signal detecting polynucleotides, each capable of hybridizing with one or more signal polynucleotides, wherein, (i) in the absence of the signal polynucleotides, the blocking sequence hybridizes with the one or more regions comprising part of the guide sequence and/or part of the sense sequence, wherein generation of the siRNA or miRNA (e.g., by Dicer cleavage) is inhibited, and/or productive incorporation of the siRNA or miRNA into RISC is inhibited; (ii) in the presence of the signal polynucleotides, the signal detecting polynucleotides hybridize with the signal polynucleotides, and allow the formation of the duplex region for the generation of the siRNA or the miRNA (e.g., by Dicer cleavage).

In certain embodiments, the presence of the signal polynucleotides, the hybridization between the signal detecting polynucleotides and the signal polynucleotides enables hybridization of the blocking sequence with a compliment sequence and relieves its inhibitory hybridization with the one or more regions comprising part of the guide sequence and/or part of the sense sequence.

In certain embodiments, in the presence of the signal polynucleotides, the hybridization between the signal detecting polynucleotides and the signal polynucleotides weakens the hybridization of the blocking sequence with the one or more regions comprising part of the guide sequence and/or part of the sense sequence, and allows the formation of the duplex region.

In certain embodiments, (i) in the absence of the signal polynucleotides, a first part of the blocking sequence hybridizes with the region comprising the part of the guide sequence to form a first additional duplex region and a first unstructured single-stranded region, and optionally, a second part of the blocking sequence hybridizes with the region comprising the part of the sense sequence to form a second additional duplex region and a second unstructured single-stranded region, and inhibits the generation of the siRNA or miRNA (e.g., by Dicer cleavage); wherein the one or more signal detecting polynucleotides are within the first and/or second unstructured single-stranded regions; (ii) in the presence of the signal polynucleotides, at least one of the signal detecting polynucleotides hybridize with the signal polynucleotides, and enable cleavage of the first and/or second unstructured single-stranded regions at one or more cleavage sites to create 5'- or 3'-OH groups; wherein the creation of the 5'- or 3'-OH groups leads to degradation of the blocking sequence and the formation of the siRNA or the miRNA, or the formation of the duplex region for cleavage by Dicer to generate the siRNA or the miRNA.

In certain embodiments, the signal-activated polynucleotide construct further comprises one or more stretches of nuclease-resistant sequences that inhibit the degradation of the duplex region.

In certain embodiments, the stretches of nuclease-resistant sequences comprise a stretch of at least about 9 nucleotides of polyguanosine, DNA, 2'-O-methyl modified nucleotide, or LNA.

In certain embodiments, the cleavage sites are cleaved by an endonuclease in the presence of the signal polynucleotides.

In certain embodiments, the endonuclease is an endoribonuclease.

In certain embodiments, the endoribonuclease is RNase H.

In certain embodiments, the endoribonuclease is RNase P.

In certain embodiments, the endonuclease is an endodeoxyribonuclease.

In certain embodiments, the endodeoxyribonuclease is a restriction endonuclease.

In certain embodiments, the cleavage sites are cleaved by a ribozyme in the presence of the signal polynucleotides.

In certain embodiments, the ribozyme is a cis-acting hammerhead ribozyme that is incorporated into the first and/or second unstructured single-stranded regions, and is allosterically activated in the presence of the signal polynucleotides.

In certain embodiments, the blocking sequence is degraded by one or more exosomes and/or exonucleases.

In certain embodiments, two or more cleavage sites are present, at least two of which capable of being cleaved by different mechanisms.

In one aspect, the invention provides a signal-activated polynucleotide construct, comprising: (1) a hairpin structure comprising: (a) a duplex region formed from a guide sequence and a sense sequence; and, (b) a single-stranded loop linking the guide sequence and the sense sequence; wherein the duplex region can form a siRNA or an miRNA comprising the guide sequence, or be cleaved by Dicer to generate the siRNA or miRNA, wherein the guide sequence is substantially complementary to a transcript of a target gene; (2) a single-stranded blocking sequence having a free end, and is linked to the guide sequence or the sense sequence, the blocking sequence comprising: (c) a stretch of nuclease-resistant sequence at the free end that inhibits the degradation of the blocking sequence by exonuclease; and, (d) one or more signal detecting polynucleotides, each capable of hybridizing with one or more signal polynucleotides; wherein, (i) in the absence of the signal polynucleotides, the blocking sequence inhibits proper Dicer cleavage of the duplex region and/or proper loading of the guide sequence in a Dicer cleavage product into a RISC complex; and, (ii) in the presence of the signal polynucleotides, at least one of the signal detecting polynucleotides hybridize with the signal polynucleotides, resulting in cleavage of the single-stranded blocking sequence at one or more cleavage sites to create 5'- or 3'-OH groups, degradation of the blocking sequence, and proper loading of the guide sequence in the Dicer cleavage product into the RISC complex.

In certain embodiments, the duplex region is about 27 base pairs in length.

In certain embodiments, the guide sequence has a two-base pair nuclease-resistant sequence at its 5'-end.

In certain embodiments, the two-base pair nuclease-resistant sequence comprise 2'-F modification.

In certain embodiments, the single-stranded blocking sequence comprises deoxyribonucleotides and/or ribonucleotides.

In certain embodiments, the single-stranded blocking sequence is linked to the guide sequence.

In certain embodiments, the single-stranded blocking sequence is linked to the sense sequence.

In one aspect, the invention provides a signal-activated polynucleotide construct, comprising: (1) a duplex region that can be cleaved by Dicer to generate an siRNA or miRNA that inhibits the expression of a target gene via RNA interference mechanism; and, (2) a blocking sequence that hybridizes with a portion of the signal-activated polynucleotide, and creates steric hindrance that inhibits Dicer cleavage of the duplex region; wherein the steric hindrance is relieved upon binding of a signal polynucleotide to the signal-activated polynucleotide, allowing the duplex region to be cleaved by Dicer to produce the siRNA or miRNA.

In certain embodiments, the duplex region is the stem of a stem-loop structure, and wherein the blocking sequence is within an overhang of the duplex region and hybridizes with the loop region of the stem-loop structure.

In certain embodiments, the signal polynucleotide hybridizes with: (1) a sequence in the loop region that does not hybridize with the blocking sequence, (2) a sequence in the loop region that does hybridize with the blocking sequence, or (3) a sequence in a linker that is between the blocking sequence and the end of the duplex region.

In certain embodiments, the signal polypeptide hybridizes with the sequence in the linker, and leads to cleavage of the linker and relief of the steric hindrance.

In certain embodiments, the linker is cleaved by a cis-acting ribozyme, a trans-acting ribozyme, a DNase, an RNase, or a RISC complex.

In certain embodiments, the signal-activated polynucleotide construct further comprises a second blocking sequence with a second overhang of the duplex region and hybridizes with a second region within the loop region.

In certain embodiments, the duplex region comprises a mismatch that enables gross distortion of the duplex region upon binding of the blocking sequence to the portion of the signal-activated polynucleotide.

In certain embodiments, the blocking sequence is a single stranded polynucleotide that hybridizes with both an overhang of the duplex region and the loop region of the stem-loop structure.

In one aspect, the invention provides a signal-activated polynucleotide construct, comprising: (1) a guide sequence and a sense sequence forming a duplex region that can become an siRNA or an miRNA comprising the guide sequence, or be cleaved by Dicer to generate the siRNA or miRNA, wherein the guide sequence is substantially complementary to a transcript of a target gene; and, (2) a signal detecting sequence capable of hybridizing with either: (a) one or more signal polynucleotides, or, (b) one or more regions of the signal-activated polynucleotide other than the guide sequence and the sense sequence; wherein, (i) in the absence of the signal polynucleotides, the signal detecting sequence hybridizes with the one or more regions of the signal-activated polynucleotide, and creates steric hindrance to inhibit the generation of the siRNA or miRNA (e.g., by Dicer cleavage of the duplex region); (ii) in the presence of the signal polynucleotides, the signal detecting sequence does not hybridizes with the regions of the signal-activated polynucleotide, and allows the duplex region to form the siRNA or the miRNA, or be cleaved by Dicer to generate the siRNA or miRNA.

In certain embodiments, the duplex region is within a stem-loop structure, and wherein the signal detecting sequence hybridizes with the single-stranded loop region of the stem-loop structure in the absence of the signal polynucleotides.

In certain embodiments, the signal polynucleotides compete with the signal detecting sequence for hybridization with the single-stranded loop region.

In certain embodiments, the signal polynucleotides hybridize with the signal detecting sequence.

In certain embodiments, the signal detecting sequence is linked to one end of the duplex region via a linker sequence.

In certain embodiments, the signal polynucleotides hybridize with the linker sequence to eliminate the steric hindrance and allows the duplex region to be cleaved by Dicer to generate the siRNA or the miRNA.

In certain embodiments, in the presence of the signal polynucleotide, the linker sequence is cleaved to relieve the steric hindrance and allows the duplex region to be cleaved by Dicer to generate the siRNA or the miRNA.

In certain embodiments, the linker sequence is cleaved by an RNase H, an RNase P, a cis-acting ribozyme, a restriction endonuclease, or a miRNA-mediated mechanism.

In certain embodiments, the duplex region comprises a mismatch, and a resulting bend of the duplex region that inhibits Dicer processing.

In certain embodiments, the single-stranded loop region hybridize with an overhang sequence of the duplex region in the absence of the signal polynucleotide.

In certain embodiments, in the presence of the signal polynucleotide, the single-stranded loop region is cleaved to relieve steric hindrance and allows the duplex region to be cleaved by Dicer to generate the siRNA or the miRNA.

In certain embodiments, the signal detecting sequence is an overhang of the duplex region, and the one or more regions of the signal-activated polynucleotide is a separate single-stranded polynucleotide that hybridize to the overhang.

In one aspect, the invention provides a signal-activated polynucleotide construct, comprising two or more tandem stem-loop structures, each comprising: (1) a guide sequence and a sense sequence forming a duplex region that can become or be cleaved by Dicer to generate an siRNA or an miRNA comprising the guide sequence, wherein the guide sequence is substantially complementary to a transcript of a target gene; and, (2) a linker sequence linking two adjacent stem-loop structures; wherein, (i) in the absence of the signal polynucleotides, the loop region of the two adjacent stem-loop structures hybridizes with each other to create steric hindrance and to inhibit the generation of the siRNA or miRNA (e.g., by Dicer cleavage of the duplex regions); (ii) in the presence of the signal polynucleotides, hybridization between the adjacent loop regions is disrupted to allows the adjacent duplex regions to generate the siRNA or the miRNA, or be cleaved by Dicer to generate the siRNA or miRNA.

In certain embodiments, at least two of the duplex regions in the stem-loop structures are different.

In one aspect, the invention provides a signal-activated polynucleotide construct, comprising two or more tandem stem-loop structures, each comprising: (1) a guide sequence and a sense sequence forming a duplex region that can become an siRNA or an miRNA comprising the guide sequence, or be cleaved by Dicer to generate the siRNA or miRNA, wherein the guide sequence is substantially complementary to a transcript of a target gene; and, (2) a linker sequence linking two adjacent stem-loop structures; wherein, (i) in the absence of the signal polynucleotides, the loop regions of the two adjacent stem-loop structures hybridizes with each other to create steric hindrance and to inhibit the generation of the siRNA or miRNA (e.g., by Dicer cleavage of the duplex regions); (ii) in the presence of the signal polynucleotides, hybridization between the signal polynucleotides and the linker sequence results in the cleavage of the linker sequence and the relief of the steric hindrance, and allows the adjacent duplex regions to form the siRNA or the miRNA, or be cleaved by Dicer to generate the siRNA or miRNA.

In one aspect, the invention provides a signal-activated polynucleotide construct, comprising: (1) a guide sequence and a sense sequence capable of forming a duplex region that can become an siRNA or an miRNA comprising the guide sequence, or be cleaved by Dicer to generate the siRNA or miRNA, wherein the guide sequence is substantially complementary to a transcript of a target gene; and, (2) a single-stranded linker sequence linking the guide sequence and the sense sequence; wherein, (i) in the absence of one or more signal polynucleotides, the linker sequence hybridizes with a blocking polynucleotide to create steric hindrance and inhibit the formation of the duplex region and the generation of the siRNA or miRNA (e.g., by Dicer); (ii) in the presence of the signal polynucleotides, the signal polynucleotides hybridize with the blocking sequence to remove the steric hindrance and allows the formation of the duplex region for the generation of the siRNA or the miRNA (e.g., by Dicer cleavage).

In certain embodiments, the linker sequence comprises the blocking sequence.

In one aspect, the invention provides a signal-activated polynucleotide construct, comprising: (1) a stem-loop structure comprising a double-stranded stem region and a single-stranded loop region, wherein one end of the stem region comprises a single-stranded overhang; (2) a single-stranded second polynucleotide that hybridizes to the overhang to form an overhang duplex, wherein a single-stranded gap region links the overhang duplex to the stem region; wherein, (i) in the absence of the signal polynucleotides, the linker sequence hybridizes with a blocking polynucleotide to create steric hindrance and inhibit the formation of the duplex region and the generation of the siRNA or miRNA by Dicer; (ii) in the presence of a signal polynucleotides, the signal polynucleotides hybridizes with the single-stranded gap region and becomes covalently linked to the overhang duplex and the stem region to create a continuous duplex region, wherein the continuous duplex region is capable of being cleaved by Dicer to generate an siRNA or an miRNA that mediates sequence-dependent gene silencing of a target gene.

In one aspect, the invention provides a signal-activated polynucleotide construct, comprising a duplex region of less than 19 base pairs in length, wherein hybridization of the signal-activated polynucleotide with a signal sequence creates a duplex region of at least 19 base pairs in length, the duplex region capable of being cleaved by Dicer to generate an siRNA or miRNA that inhibits the expression of a target gene using an RNA interference mechanism.

In one aspect, the invention provides a signal-activated polynucleotide construct comprising a duplex region having one or more mismatches that inhibits the duplex region from being cleaved by Dicer, wherein hybridization of the signal-activated polynucleotide with a signal sequence creates a duplex region, the duplex region capable of being cleaved by Dicer to generate an siRNA or miRNA that inhibits the expression of a target gene using an RNA interference mechanism.

In one aspect, the invention provides a circular signal-activated polynucleotide construct, comprising: (1) a duplex region of at least 19 nucleotides, and (2) two single-stranded loop regions, one at each end of the duplex region, wherein one or both of the loop regions can hybridize with a signal polypeptide, wherein, (a) in the absence of the signal polypeptide, the duplex region is not a Dicer substrate, (b) in the presence of the signal polypeptide, the one or both loop regions hybridize with the signal polypeptide and enables cleavage of the loop regions, wherein the duplex region becomes a Dicer substrate upon cleavage of the one or both loop regions, and wherein cleavage of the duplex region by Dicer produces an siRNA or miRNA that inhibits the expression of a target gene through an RNA interference mechanism.

In one aspect, the invention provides a method to inhibit expression of a target gene, comprising providing an effective amount of the subject constructs and at least one the signal polynucleotides.

In certain embodiments, the target gene is within a cell.

In certain embodiments the cell is contacted with the subject constructs in vitro.

In certain embodiments the cell is that of a human, a non-human primate, a non-primate mammal, a rodent, a livestock animal, a bird, an insect (e.g., fly), a worm, or a plant.

In one aspect, the invention provides a pharmaceutical composition comprising an effective amount of one or more of the subject constructs, and a pharmaceutically acceptable amount of excipients, carriers, or diluents.

In one aspect, the invention provides a vector encoding the subject constructs.

In one aspect, the invention provides a cell comprising the subject constructs or a vector encoding the subject constructs.

In one aspect, the invention provides a non-human organism comprising the subject cell.

In one aspect, the invention provides a molecular signaling network or circuit, comprising: (1) one or more input signals; (2) one or more of the subject constructs, or a vector encoding the subject constructs, wherein each of the constructs is independently capable of being activated by at least one of the input signals, as manifested by the production of the siRNA or miRNA; and, (3) one or more target gene transcripts, wherein the expression of the target gene transcripts is inhibited by the siRNA or miRNA.

All the figures and the entire contents of the provisional applications U.S. Patent Application No. 61/007,004 and U.S. Patent Application No. 61/063,604 are hereby incorporated by reference.

It is contemplated that any embodiments described herein, including those only described under one of the many aspects of the invention, can be combined with any other embodiments described under any aspects of the invention whenever appropriate.

BRIEF DESCRIPTION OF THE DRAWINGS

" In FIG. 1, panel A, inactive (3-Arm Junction) Conformation is shown. In this conformation, the signal-activated polynucleotide construct cannot be processed by Dicer or the Rise Loading Complex (RLC). On left, labels identify the passenger strand stem (or sense sequence) in the truncated form (~16 nucleotides), and the guide strand stem (or guide sequence) in the truncated Form (~18 nucleotides). A separate region is responsible for junction formation and input sensing, and serves as the signal-detecting strand. There are ~20 nucleotides in an unstructured region of the polynucleotide construct. The input strand (or signal polynucleotide) hybridizes to and displaces the signal-detecting strand. The inputs may comprise probe outputs, mRNA, miRNA or any molecule, acting either alone or in combination. In addition, there may be one or two inputs that bind to ~9-12 nucleotides toeholds (see arrows) and "activate" the saRNAi. Constructs requiring two inputs is a 2-input AND gate for saRNAi activation. Using two identical inputs, or, alternately, using two different inputs gives rise to a 2-input AND gate. One or two inputs (probe outputs/mRNA/miRNA/etc.) bind to ~9-12 nt toeholds and 'activate' the saRNAi. Requiring two inputs makes a 2-input AND gate for saRNAi activation. FIG. 1, panel B, shows active (telescoped) conformation. In this conformation, the molecule can be processed by Dicer or the RLC. The passenger strand shown is ~21 nucleotides. The guide strand shown is ~21 nucleotides. There is also a 3' overhang comprising 2 nucleotides, and the total length of the duplex region is ~28 nucleotides, which includes ~21 nucleotides from the passenger strand paired to complementary sequences in the guide strand, and 7 additional nucleotides paired with complementary base pairs. Other patterns of mismatches or wobble bases can be used. Short arrows indicate Dicer cleavage positions. One input or two identical or different inputs (2-input AND gate) can be used to activate the saRNAi.

" FIG. 2, panel A, shows the inactive (masked) conformation. In this conformation, the signal-activated polynucleotide construct cannot be processed by Dicer or the RISC Loading Complex (RLC). The passenger strand stem (or sense sequence) in the truncated form (~16 nucleotides) and the guide strand stem (or guide sequence) in the truncated Form (~18 nucleotides) are labeled. The scheme will also work if this side is "masked." The chimeric mask (labeled) serves as the signal-detecting strand. The chimeric mask region shown comprises ~16 nucleotides. This strand may comprise DNA, LNA, 2'-OMe, other exemplary modified nucleotides, or other processable nucleotides that displace an all-RNA segment comprising ~12 nucleotides. Chimeric 'mask' (orange): DNS/LNA/2'-OMe/etc.nts displace ~12 nt all-RNA segment (red+black) and block dicer processing and/or RISC loading. Mask region is ~16(+) nts long. Orange region can potentially be all_RNA (non-chimeric) since large bulge (green/black/red) can act to inhibit proper dicer processing and RISC loading. Input strand (probe output/mRNA/miRNA/etc.) blinds ~9-12 nt toehold (unstructured orange) and 'activates' the (sa)RNAI by displacing the chimeric mask. This then allows the previously unstructured all-RNA region (red-black) to make an active Dicer substrate. It should also be possible to require two inputs (one on either side) to strip off the mask. This creates a 2-inout AND gate for (sa)RNAi activation. Alternately, this region may comprise all RNA (thus creating a non-chimeric molecule) since the formation of a large bulge may inhibit proper Dicer processing and RISC loading. Processing by Dicer and loading into RISC are blocked by the chimeric mask. The mask further serves as a sensing region and has a ssRNA toehold for mRNA binding. Also present is a ~20 nucleotides unstructured region. The input (or signal) strand show on the right may be an output probe, an mRNA signal, a miRNA or any molecule, acting either alone or in combination. The input strand can bind to a toehold of ~9-12 nucleotides and displaces the chimeric mask. This then allows the previously unstructured region to make an active Dicer substrate. In some embodiments, one or more signal strands may be required to displace the chimeric mask. A 2-input AND gate may be generated for this scheme of saRNAi activation. FIG. 2, panel B, shows the active (unmasked) conformation. In this conformation, the molecule may be processed by Dicer/RLC. The passenger strand shown is ~21 nucleotides. The guide strand shown is ~21 nucleotides. There is a 3' overhang comprising 2 nucleotides, and the total length of the duplex region is ~28 nucleotides, which includes ~21 nucleotides from the passenger strand paired to complementary sequences in the guide strand, and 7 additional nucleotides paired with complementary base pairs. Other patterns of mismatches or wobble bases can be used. Short arrows indicate Dicer cleavage positions.

FIG. 4, panel A, shows the inactive (3-arm junction) conformation. In this conformation, the signal-activated polynucleotide construct cannot be processed by Dicer or the Rise Loading Complex (RLC). Labels identify the passenger strand stem in the truncated form (~16 nucleotides) and the guide strand stem in the truncated form (~18 nucleotides). Also labeled are nuclease-resistant nucleotide bases, of which there may be at least 9 nucleotides. Nuclease resistance may be conferred by use of polyguanosine (>9 nucleotides), DNA, 2'-OMe, or LNA, or forms of RNase resistant bases. The input strand (labeled) represents one of many possible input strands that bind and induce cleavage of complementary sequences. The signal strands may be DNA or RNA, or miRNA as the system may be autocatalytic. An RNase H mechanism may be used for bound DNA and an Ago2 mechanism may be used for miRNA. The cleavage sites and alternate cleavage sites are indicated by asterisks. Many other binding sites are possible although not all are shown. RNase H mechanism for bound DNA & Ago2 mechanism for miRNA. In some embodiments, this scheme also allows for any allosteric ribozyme (can be on green strand and cis-acting) where cleavage is induced by a nucleic acid binding event and/or the binding of some other factor (TAAs/etc). In some embodiments, the allosteric ribozyme may be on the strand near to the asterisks, and may be cis-acting. In other embodiments, the cleavage may be induced by a nucleic acid binding event and/or the binding of any other factor. One exemplary factor is TAA. Processive exonucleases can degrade the regions indicated with free ends. Processive exonucleases (5'->3') Red)=Xrn1/etc., 3'->5' (Blue)=exosome/etc.) can only degrade strand region drawn in purple. 3'->5' activity unnecessary for saRNAi activation. The circle labeled 5' represents 5' to 3' processive exonucleases such as Xrn1, while the circle labeled 3' represents 3' to 5' processive exonucleases. The small black arrow points to a region comprising 30 or more nucleotides of ssRNA leader sequence. FIG. 4, panel B, shows the active (telescoped) conformation. In this conformation, the molecule may be processed by Dicer/RLC. The passenger strand shown is ~21 nucleotides. The guide strand shown is ~21 nucleotides. There is a 3' overhang comprising 2 nucleotides, and the total length of the duplex region is ~28 nucleotides, which includes ~21 nucleotides from the passenger strand paired to complementary sequences in the guide strand, and 7 additional nucleotides paired with complementary base pairs. Other patterns of mismatches/wobble bases can be used so long as they allow for initial three-arm junction configuration. Small arrows indicated the Dicer cleavage sites.

FIG. 5, panel A, shows the inactive (3-arm junction) conformation. In this conformation, the signal-activated polynucleotide construct cannot be processed by Dicer or the Rise Loading Complex (RLC). Labels identify the passenger strand stem in the truncated form (~16 nucleotides) and the guide strand stem in the truncated form (~18 nucleotides). Also labeled are nuclease-resistant nucleotide bases, of which there may be at least 9 nucleotides. Nuclease resistance may be conferred by use of polyguanosine (>9 nucleotides), DNA, 2'-OMe, or LNA, or forms of RNase resistant bases. The input strand (labeled) represents one of many possible input strands that bind and induce cleavage of complementary sequences. The signal strands may be DNA or RNA, or miRNA as the system may be autocatalytic. An RNase H mechanism may be used for bound DNA and an Ago2 mechanism may be used for miRNA. The cleavage sites and alternate cleavage sites are indicated by asterisks. Many other binding sites are possible (pink asterisks) although not all are shown. In some embodiments, this scheme also allows for any allosteric ribozyme. In some embodiments, the allosteric ribozyme may be on the strand near to the asterisks, and may be cis-acting. In other embodiments, the cleavage may be induced by a nucleic acid binding event and/or the binding of any other factor. One exemplary factor is TAA. Processive exonucleases can degrade the regions indicated with free ends. The circle labeled 5' represents 5' to 3' processive exonucleases such as Xrn1, while the circle labeled 3' represents molecules such as the exosome. 5' to 3' activity is not necessary for saRNAi activation. The small black arrow points to a region comprising 30 or more nucleotides of ssRNA leader sequence. FIG. 5, panel B, shows the active (telescoped) conformation. In this conformation, the molecule may be processed by Dicer/RLC. The passenger strand shown is ~21 nucleotides. The guide strand shown is ~21 nucleotides. There is a 3' overhang comprising 2 nucleotides, and the total length of the duplex region is ~28 nucleotides, which includes ~21 nucleotides from the passenger strand paired to complementary sequences in the guide strand, and 7 additional nucleotides paired with complementary base pairs. Other patterns of mismatches/wobble bases can be used so long as they allow for initial three-arm junction configuration. Small arrows indicated the Dicer cleavage sites.

FIG. 6, panel A, shows the inactive (masked) conformation. In this conformation, the signal-activated polynucleotide construct cannot be processed by Dicer or the Rise Loading Complex (RLC). Labels identify the passenger strand stem in the truncated form (~16 nucleotides) and the guide strand stem in the truncated form (~18 nucleotides). Also pictured are nuclease-resistant nucleotide bases, of which there may be at least 9 nucleotides. Nuclease resistance may be conferred by use of polyguanosine (>9 nucleotides), DNA, 2'-OMe, or LNA, or forms of RNase resistant bases. Represented on the figure are unstructured regions where signal strands may bind, and one of many possible input or signal strands that bind and induce cleavage of complementary sequences. The signal strands may be DNA or RNA or miRNA. The cleavage sites and alternate sites are indicated by (pink) asterisks. In some embodiments, this scheme allows for an allosteric ribozyme (can be on green strand and cis-acting). The allosteric enzyme can be on the unstructured region, and may be cis-acting. Cleavage is induced by a nucleic acid binding event, binding of other factors, or a combination of both events. TAAs are one example of factors that bind and induce cleavage. The chimeric mask is also labeled (orange). This region may comprise DNA, modified nucleotides, or other processable nucleotides that displace an all-RNA segment comprising ~12 nucleotides (red and black) and block dicer processing and/or RISC loading. The mask region may comprise ~16 nucleotides. Orange region can potentially be all-RNA (non-chimeric) since large burlge (green/black/red) can act to inhibit proper dicer processing and RISC loading. The signal-activated polynucleotide after cleavage has occurred, at or near the locations where the signal strand binds to complementary sequence. Once cleaved, the processive 5' to 3' exonucleases digest the chimeric mask and proximal sequences (purple). FIG. 6, panel B, shows the active (telescoped) conformation. In this conformation, the molecule may be processed by Dicer/RLC. The passenger strand shown is ~21 nucleotides. The guide strand shown is ~21 nucleotides. There is a 3' overhang comprising 2 nucleotides, and the total length of the duplex region is ~28 nucleotides, which includes ~21 nucleotides from the passenger strand paired to complementary sequences in the guide strand, and 7 additional nucleotides paired with complementary base pairs. Other patterns of mismatches/wobble bases can be used so long as they allow for initial three-arm junction configuration. Small arrows indicated the Dicer cleavage sites.

Figure 1:
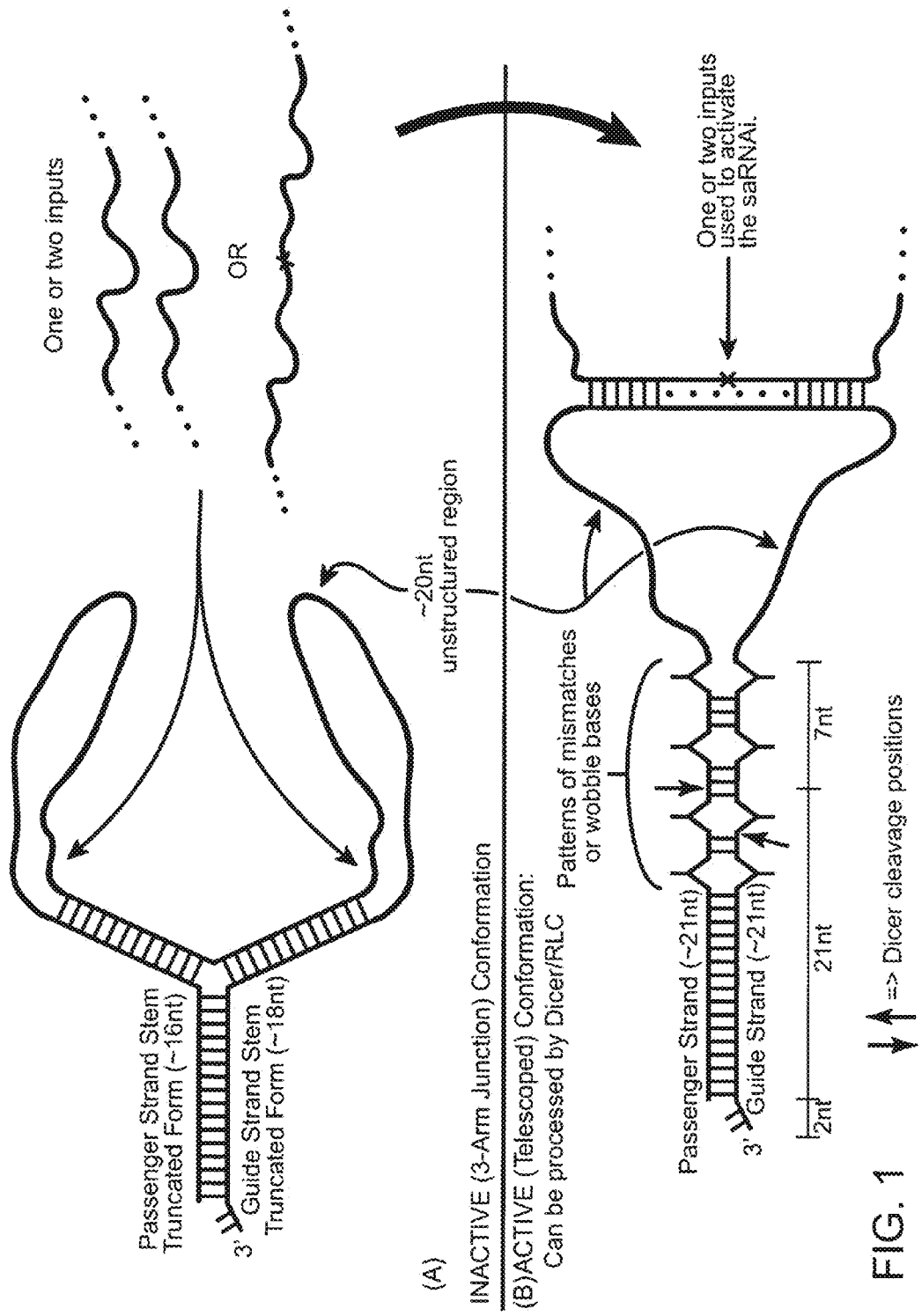
FIG. 1, panels A-B, shows an illustrative embodiment of the "Signal Activated (sa)RNAi—Telescoping Platform.
Figure 2:
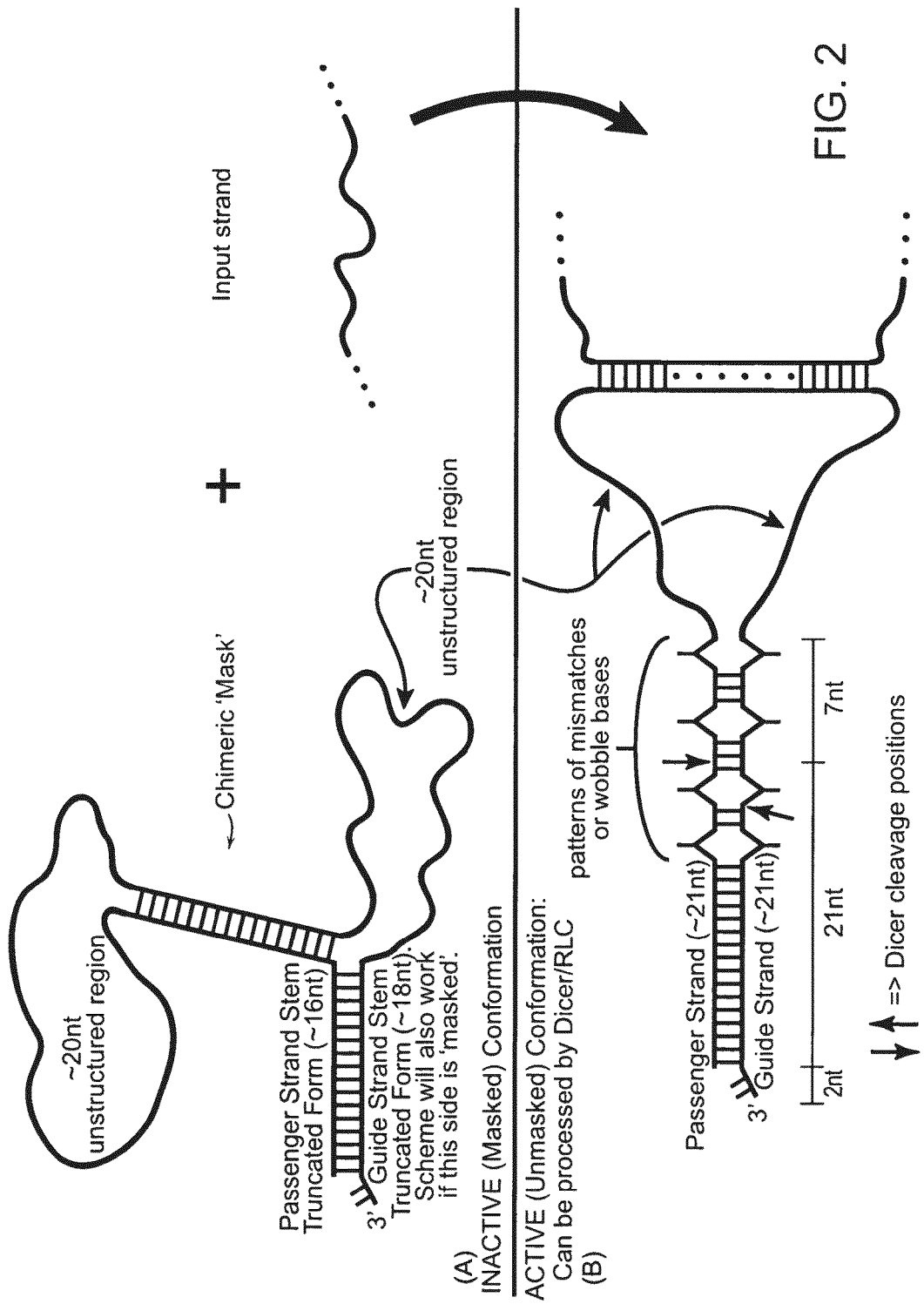
FIG. 2, panels A-B, shows an illustrative embodiment of the "Signal Activated (sa)RNAi—Chimera-Masking Platform.
Figure 3:
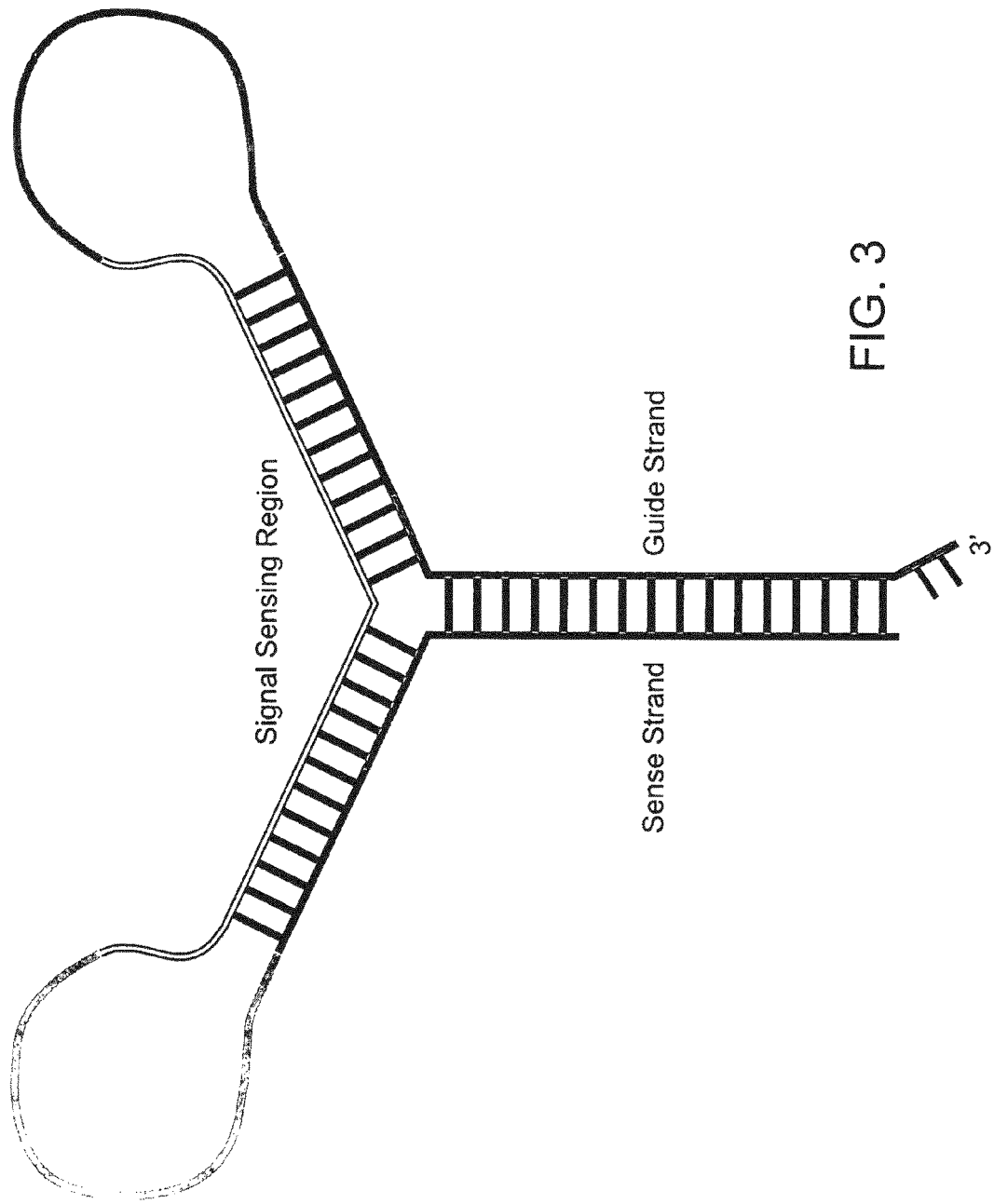
FIG. 3 shows a non-limiting list of advantages of the keyhead design for the subject constructs. Such advantages include inactivation mechanisms that act via pure secondary structure. The Single stable conformation is robust over wide range of conditions (as compared to tertiary structures). The three-way junction is stable in MD. The keyhead design is suitable for endogenous expression, as the secondary structure folds is <1 ms). Additional features of the keyhead design include ease of engineering overlap for arbitrary signal-target mix. The signal sensing region (orange) and guide strand (red) share only 3 bases. The sense strand (blue) shares 5 bases with orange but may have greater sequence freedom due to mismatches with guide strand. Designs may have shorter arms and even less homology. Two arbitrarily long loop input regions allow a large number of inputs for degradation based schemes. There may also be sites for attachment to delivery vehicles, an alternative export pathway by attaching to tRNA, and the two sensing arms give the intrinsic option of using 2-input AND gate. Safe degradation by 5' to 3' exo-nucleases is another potentially advantageous feature. There is little endonuclease in cytoplasm, and 5' to 3' degradation means the RNAi segment is destroyed first. The main stem shown is approximately 16 nucleotides long and the sensing stems are only 9-12 nucleotides each. The main stem is too short for Dicer processing (requires 19 nucleotide minimum). The total length of any two stems may be kept at less than 29 nucleotides in order to ameliorate the intracellular immune response. A 9-nucleotide arm prevents incorrect pri-miRNA processing. An optimal 3' miRNA overhang structure can mediate proper binding of the polynucleotide to the Dicer PAZ domain. A clear preference for the guide strand is created in RISC. The stronger duplex character reinforces Red strand preference. The minimal exo-ribonuclease toehold leads to long lifetimes, and proper nuclear export by exportin 5. Analogous structures include the theophylline aptamer inactive in vivo and CNG repeats active in vivo.
Figure 4:
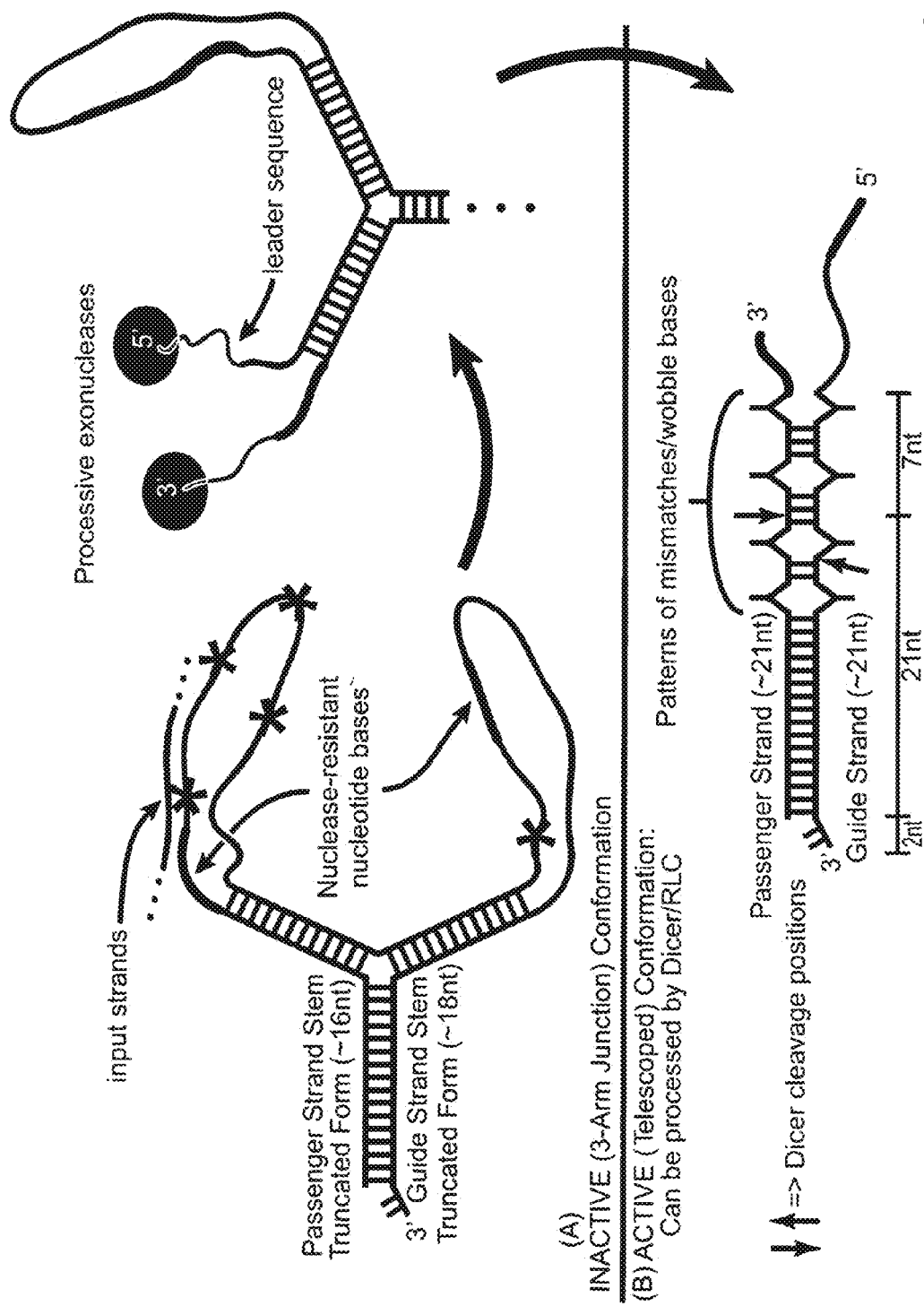
FIG. 4, panels A-B, shows an exemplary embodiment of the "degradation-activated, signal-activated (sa)RNAi," using a Xrn1 route with a telescoping platform.
Figure 5:
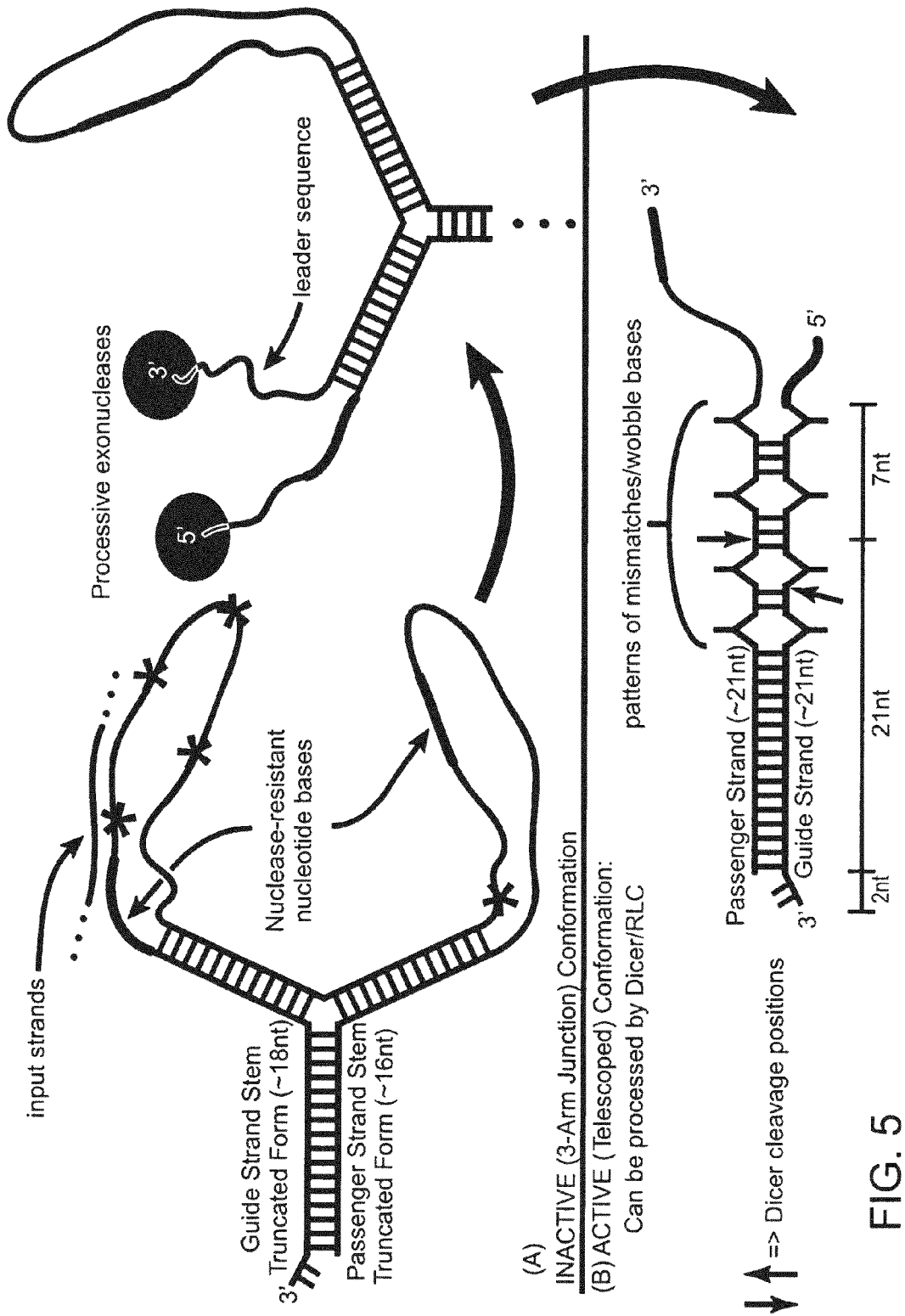
FIG. 5, panels A-B, shows an exemplary embodiment of the "degradation-activated, signal-activated (sa)RNAi," using an exosome route with a telescoping platform.
Figure 6:
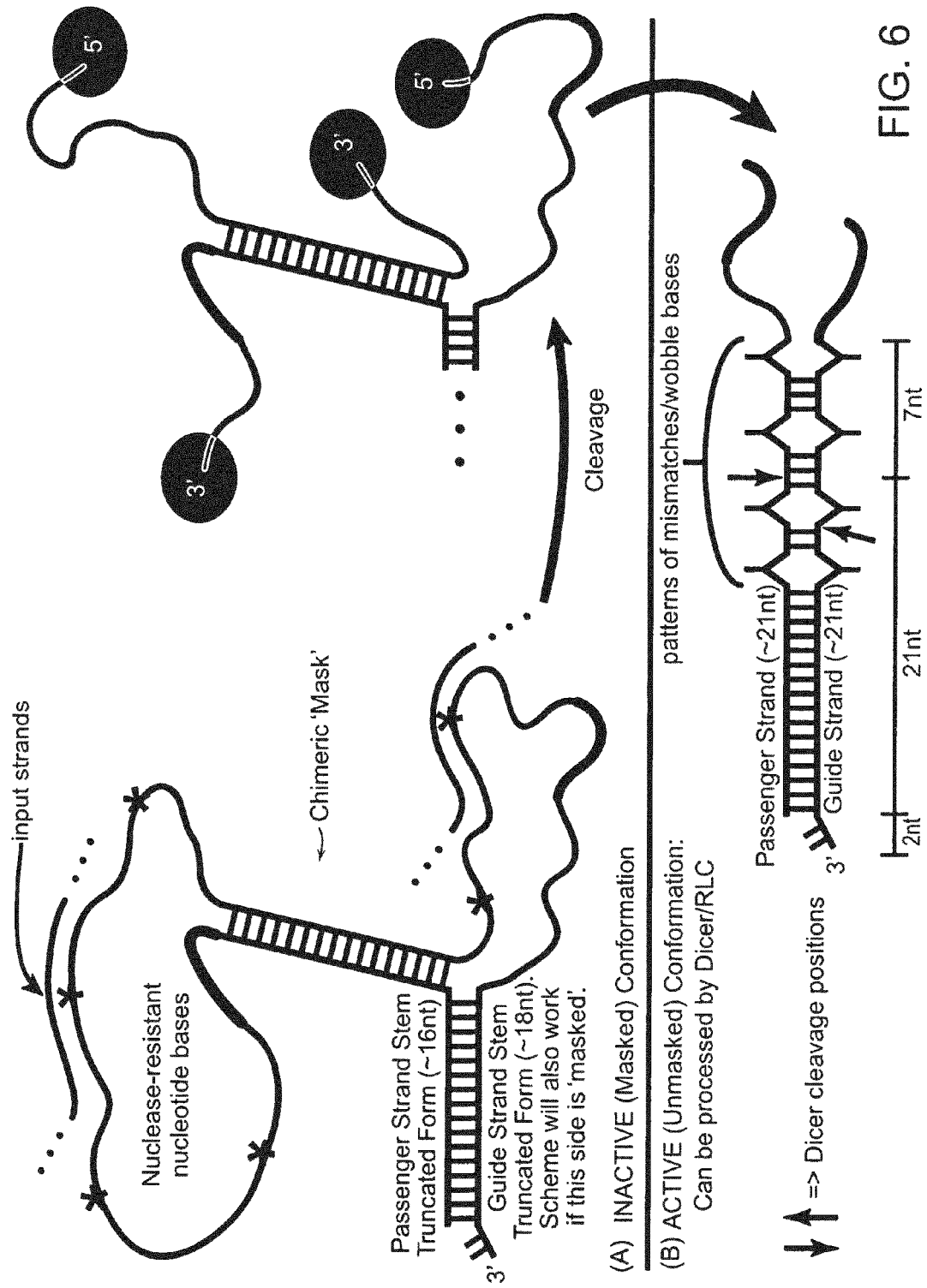
FIG. 6, panels A-B, shows an exemplary embodiment of the "degradation-activated, signal-activated (sa)RNAi," using a chimera masking platform.
Figure 7:
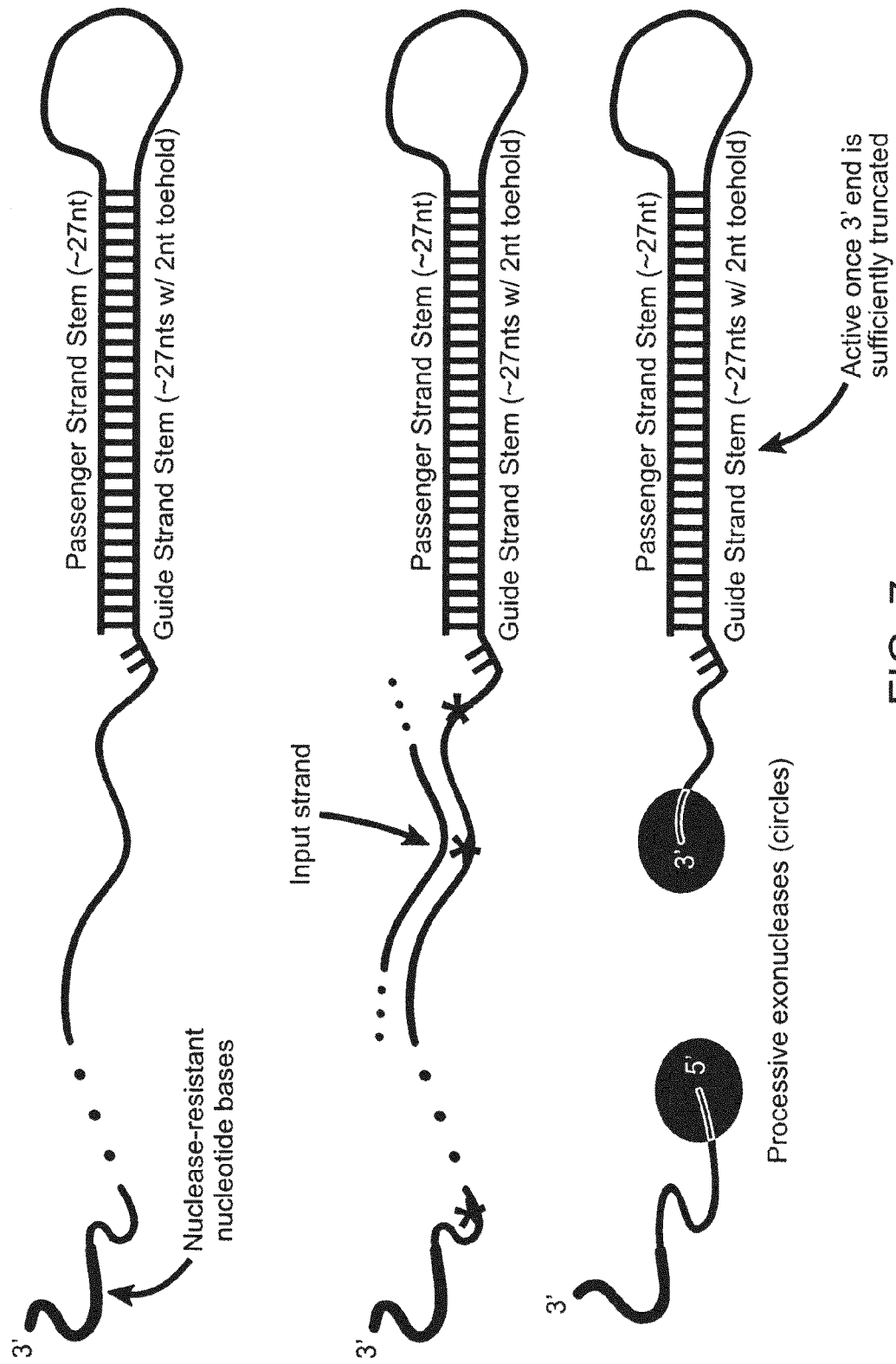
FIG. 7 shows an exemplary embodiment of the "degradation-activated, signal-activated (sa)RNAi," using a 3' tail truncation platform. Labeled are the passenger stem strand (~27 nucleotides long) and the guide strand stem (~29 nucleotides long). Located at the 3' end of the molecule are nuclease-proof nucleotide bases. Nuclease resistance may be conferred by use of polyguanosine (>9 nucleotides), DNA, 2'-OMe, or LNA, or forms of RNase resistant bases. The nuclease-proof nucleotides cap the end of a long single strand of nucleotides at the 3' end of the molecule. The signal strand binds and induces cleavage of complementary sequence. Cleavage sites and alternate cleavage sites are indicated with asterisks. The complementary sequence to which the signal strand binds may comprise RNA, miRNA, DNA, or other molecules. In some embodiments, this scheme allows for an allosteric ribozyme. The allosteric enzyme can be on the region pictured in near to the asterisks, and may be cis-acting. Cleavage is induced by a nucleic acid binding event, binding of other factors, or a combination of both events. TAAs are one example of factors that bind and induce cleavage. Only a single binding site is shown, but like in other schemes, many more can be encoded on extended 3' tail to make an N-OR gate for saRNAi activation (pink asterisks). After the cleavage reaction, various processive exonucleases digest the cleaved segment. The cleaved segment is pictured at the bottom left, where the circles labeled with 5' and 3' represent exonucleases that digest the cleaved segment, but stop at the guide strand toehold. In some embodiments, the guide strand may have a bases that cannot be processed by ribonucleases and therefore still allow for RISC loading. 2'-fluoro is one example of base that cannot be processed. In other embodiments, outside of a miRNA cleavage region, the region to be digested by exonucleases can be DNA, while the guide strand stem can be RNA. In further embodiments, the previous two embodiments may be varied such that blocking exonucleases may be halted by nucleotide-type switching, linkage-switching (2') and/or blocking agents. The duplex formed by the guide strand and the sense strand will be active once the 3' end is sufficiently truncated such that the 3' end fits into the PAZ domain of Dicer. Dicer processing should not occur earlier, due to the short stem (~27 nucleotides). This stem may be further truncated as necessary. If Dicer processing does occur, a long 3' tail should block RISC entry.
Figure 8:
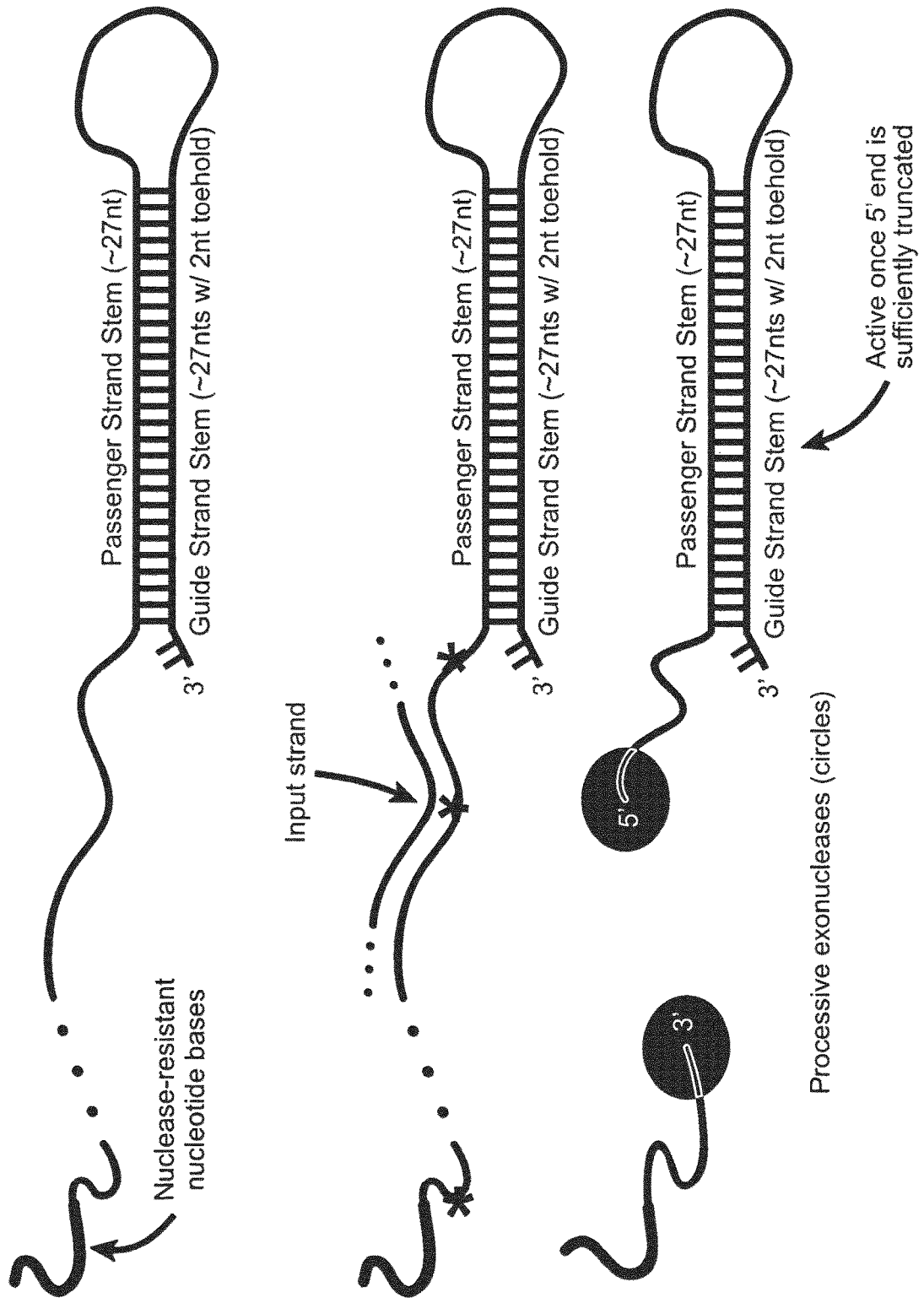
FIG. 8 shows an exemplary embodiment of the "degradation-activated, signal-activated (sa)RNAi," using a 5' tail truncation platform. Labeled are the passenger stem strand (~27 nucleotides long) and the guide strand stem (~29 nucleotides long). Located at the 5' end of the molecule are nuclease-proof nucleotide bases. Nuclease resistance may be conferred by use of polyguanosine (>9 nucleotides), DNA, 2'-OMe, or LNA, or forms of RNase resistant bases. The nuclease-proof nucleotides cap the end of a long single strand of nucleotides at the 5' end of the molecule. The signal (input) strand binds and induces cleavage of complementary sequence. Cleavage sites and alternate cleavage sites are indicated with asterisks. The complementary sequence to which the signal strand binds may comprise RNA, miRNA, DNA, or other molecules (at red asterisk). RNase H mechanism for bound DNA & Ago2 mechanism for miRNA. In some embodiments, this scheme allows for an allosteric ribozyme The allosteric enzyme can be on the region pictured in near to the a (green) asterisks, and may be cis-acting. Cleavage is induced by a nucleic acid binding event, binding of other factors, or a combination of both events. TAAs are one example of factors that bind and induce cleavage. Only a single binding site is shown, but like in other schemes, many more can be encoded on extended 5' tail to make an N-OR gate for saRNAi activation (pink asterisks). After the cleavage reaction, various processive exonucleases (brown/green) digest the cleaved (purple) segment. The cleaved segment is pictured at the bottom left, where the circles labeled with 5' and 3' represent exonucleases that digest the cleaved segment, but stop at the guide strand toehold or the dsRNA stem (passenger strand stem). In some embodiments, the passenger strand stem may have bases that cannot be processed by ribonucleases. Such bases may be 2'-OMe or DNA, though one should avoid allowing 5' tail (purple) to be all RNA to prevent two Dicer cleavage events that can potentially make an active RISC-loadable complex. Outside of a miRNA cleavage region, purple strand can be DNA and passenger strand stem can be RNA. Thus exonucleases chew to the stem and then, due to lack of toehold, RNA exonucleases take a long time to digest the now-active shRNA. Similarly, duplex itself may be sufficient to halt digestion. In other embodiments, the 5' single strand may comprise DNA and the guide strand stem may comprise RNA. In further embodiments, the previous two embodiments may be varied such that blocking exonucleases may be halted by nucleotide-type switching, linkage-switching (2') and/or blocking agents. The duplex formed by the guide strand and the sense strand will be active once the 5' end is sufficiently truncated to allow for RISC loading, which may occur after a Dicer cleavage event. Dicer processing may occur before the 5' is truncated, but a co-factor (possibly R2D2) that senses a 5' phosphate on the sense strand may block RISC entry if the tail is not removed. Variants of (1)+(2) and so on where nucleotide-type switching/linkage-switching (2'?)/blocking agents halt exonucleases at passenger strand stem.

Nuclease-proof nucleotide bases in the loop regions are also labeled. Nuclease resistance may be conferred by use of polyguanosine (>9 nucleotides), DNA, 2'-OMe, or LNA, or forms of RNase resistant bases. The nuclease resistant bases stop exonuclease digestion and act as checkpoints between hairpins for the N-Bit AND/NAND gates.

As used herein, an "N-bit gate" refers to a circuit that accepts "N" different binary inputs. The gate may be AND, OR, NAND, NOR, and more. For example, in an N-bit AND gate, "N" degradation or branch migration steps (in which polyguanosine, modified bases, etc. act as "stops" in the degradation process) are required to activate a given saRNA. Alternately, an N-bit NAND gate may require "N" degradation or branch migration steps to lead to the destruction or blockage (via hybridization) of a shRNA, siRNA, IRES, or other molecule. This molecule may be either active or inactive before the destruction step.

In some embodiments, an N-bit AND and a N-bit NAND gate may be coupled, to "race" the two different gates against each other. If the N-bit NAND gate wins, an inactive saRNA construct will be destroyed or permanently inactivated. In contrast, if the N-bit AND gate wins, the saRNA construct will be activated. In many embodiments, the activation will be permanent, because the oligonucleotide gets cleaved and/or loaded into RISC. The "race" may be determined by the presence and/or the relative concentration of different inputs.

For example, a certain mRNA may be downregulated in cancer (mRNA "A") while another is either static or upregulated (mRNA "B"). A standard saRNAi would be difficult to activate in a cancerous cell using the absence of "A" or a subtle change in the concentration of "A" as a signal. In contrast, the use of an N-bit NAND gate that accepts mRNA "A" signals and an N-bit AND gate that accepts mRNA "B" signals, would bypass this difficulty. Activation would occur only if mRNA "B" binding events are faster than mRNA "A" binding events. Notably, by increasing the number of inputs "N," it is possible to discriminate between very subtle differences in concentration of inputs, such as the case where there is only slightly less of A than B.

In some embodiments, allosteric ribozymes, miRNA binding sites, and more may be encoded into the loops of the hairpin structures. Using these embodiments, it may be possible to jump ahead on the chain without the need to go through the hairpins sequentially.

When all hairpins are bypassed, there are several potential outcomes. In certain embodiments, an NAND gate is used, the catalytic, antisense, masked miRNA, IRES etc. on an mRNA is degraded I inactivated. In certain embodiments, an AND gate is used, the opposite occurs and the (orange) strand is freed and/or activated. The (blue) tail on the opposite side of the gate hairpins can be nuclease-hardened or kept short to slow exonuclease action. RNase H mechanism can be used to degrade strand if tail is fully nuclease-hardened. This tail can also be sequestered by binding a freed region on the strand once the AND gate is activated, thus greatly slowing nuclease action. In certain embodiments, an AND gate and a NAND gate are placed on opposite sides of the hairpin containing the strand, and they "race" two or more inputs (such as RNA, miRNA, proteins, and more) against one-another for concentration dependent activation. Using the sequestering technique for the tail, if the AND gate is activated first it can inactivate digestion of the strand by the NAND gate.

Top right, box inset shows the N-Bit AND Gate, with the catalytic, antisense, masked miRNA, or IRES, etc. strand being gated. Bottom right, box inset shows the N-Bit NAND gate. The "hardened" (brown) region may be absent.

Figure 10:
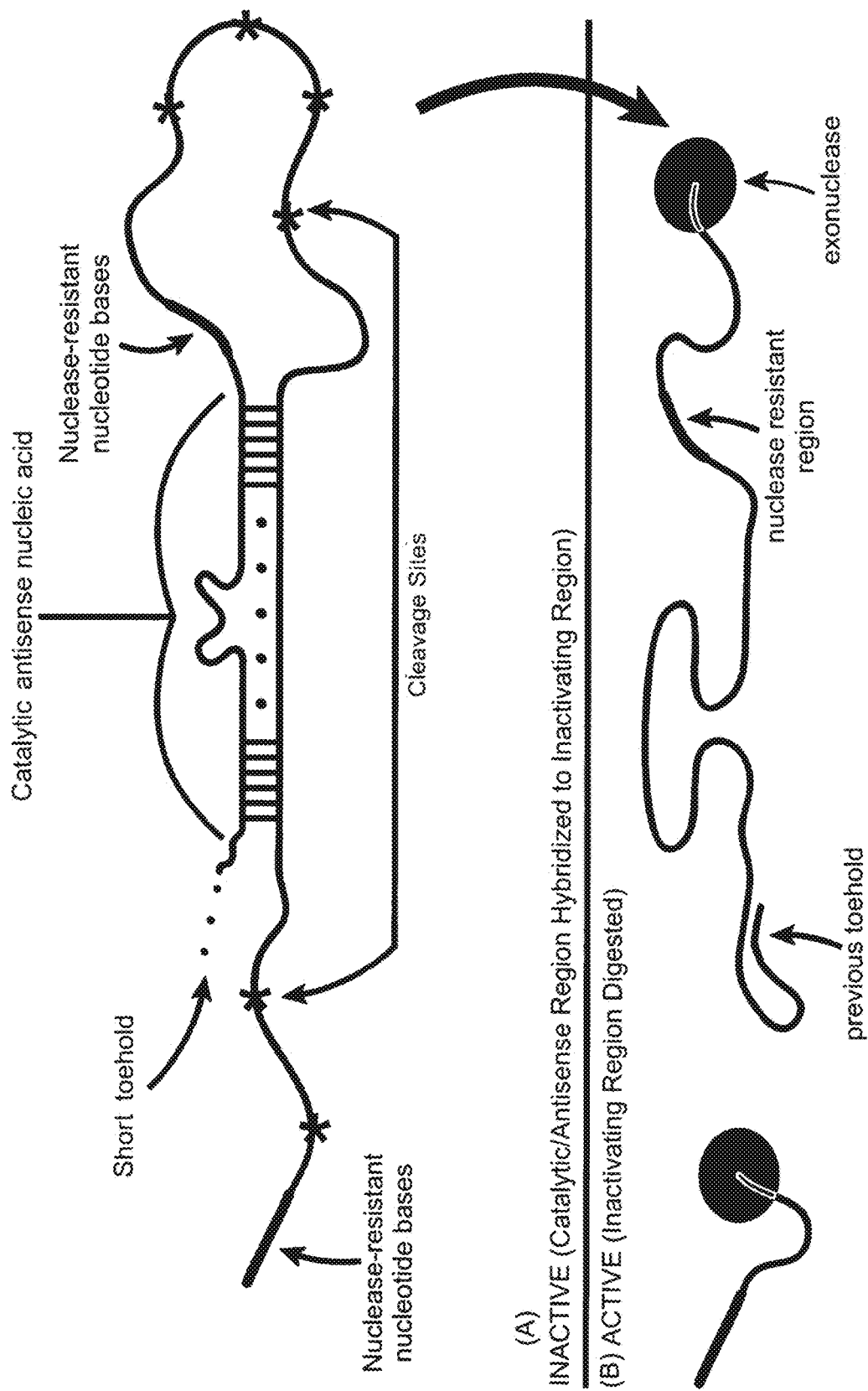

FIG. 10, panels A-B, shows an exemplary embodiment of the degradation-activation of catalytic/antisense I IRES etc. nucleic acids. FIG. 10, panel A, shows the inactive conformation (catalytic/antisense region hybridized to inactivating region). A short toehold (blue), comprising ssRNA, ssDNA, etc. (indicated with arrow and label), may be at 3' or 5' end, depending on scheme. This toehold slows digestion of a strand that may comprise a catalytic, antisense, masked miRNA, IRES on an mRNA, etc. strand (orange), or other type of nucleic acid. The strand may also comprise modified, nuclease resistant bases. Nuclease resistance may be conferred by use of polyguanosine (>9 nucleotides), DNA, 2'-OMe, or LNA, or forms of RNase resistant bases. The nuclease resistant bases stop exonuclease digestion and act as checkpoints between hairpins for the N-Bit AND/NAND gates.

Some nuclease activity at this end may provide a degradation pathway (without activation) for the catalytic/antisense/etc. region. In other embodiments, the RNase H degradation pathway is engineered were the inactivating (black) strand is DNA and catalytic or antisense (orange) strand is RNA or some other RNase H processible nucleic acid variant. Once activation occurs, the toehold can be hybridized to modified nucleic acids or simply bound to a complementary region to further slow digestion.

The catalytic (i.e. ribozyme/deoxyribozyme, etc.), antisense nucleic acid, masked miRNA, IRES on an mRNA, etc. (orange) strand is paired to an inactivating region or mask (black). Modified bases (are allowed) may be present, but these must permit progression of exonucleases. In other embodiments, an endonuclease (RNase H, etc.) degradation route may be engineered where the inactivating (black) strand is DNA and catalytic/antisense/etc. (orange) strand is RNA or some other RNase H processible nucleic acid variant.

Nuclease-resistant bases are labeled. Nuclease resistance may be conferred by use of polyguanosine (>9 nucleotides), DNA, 2'-OMe, or LNA, or forms of RNase (nuclease) resistant bases.

The input strand (bracketed) represents one of many possible input strands that bind and induce cleavage of complementary sequences. The cleavage sites, and other possible sites, are indicated in pink asterisks. Other possible cleavage sites are not indicated. The input strands may be DNA or RNA, or miRNA as the system may be autocatalytic. An RNase H mechanism may be used for bound DNA and an Ago2 mechanism may be used for miRNA. In some embodiments, this scheme also allows for any allosteric ribozyme. In some embodiments, the allosteric ribozyme may be on the green strand near to the asterisks, and may be cis-acting. In other embodiments, the cleavage may be induced by a nucleic acid binding event and/or the binding of any other factor. One exemplary factor is TAA.

FIG. 10, panel B, shows the active conformation (inactivating region digested). When the antisense/catalytic strand/IRES on an mRNA/etc. region has been activated, the previous toehold (arrow) may hybridize to a newly single-stranded region to further slow nuclease digestion. After the cleavage event, exonucleases start to digest the inactivating region and surrounding single-stranded extensions that facilitate nuclease initiation (purple region gets digested). Nucleases are corralled between nuclease-resistant regions. Here, 5'/3' ends are not specified and either orientation will work. In some embodiments, Xrn1 can handle 5' to 3' digestion of RNA, while 3' to 5' digestion may be handled by the exosome.

Figure 11:
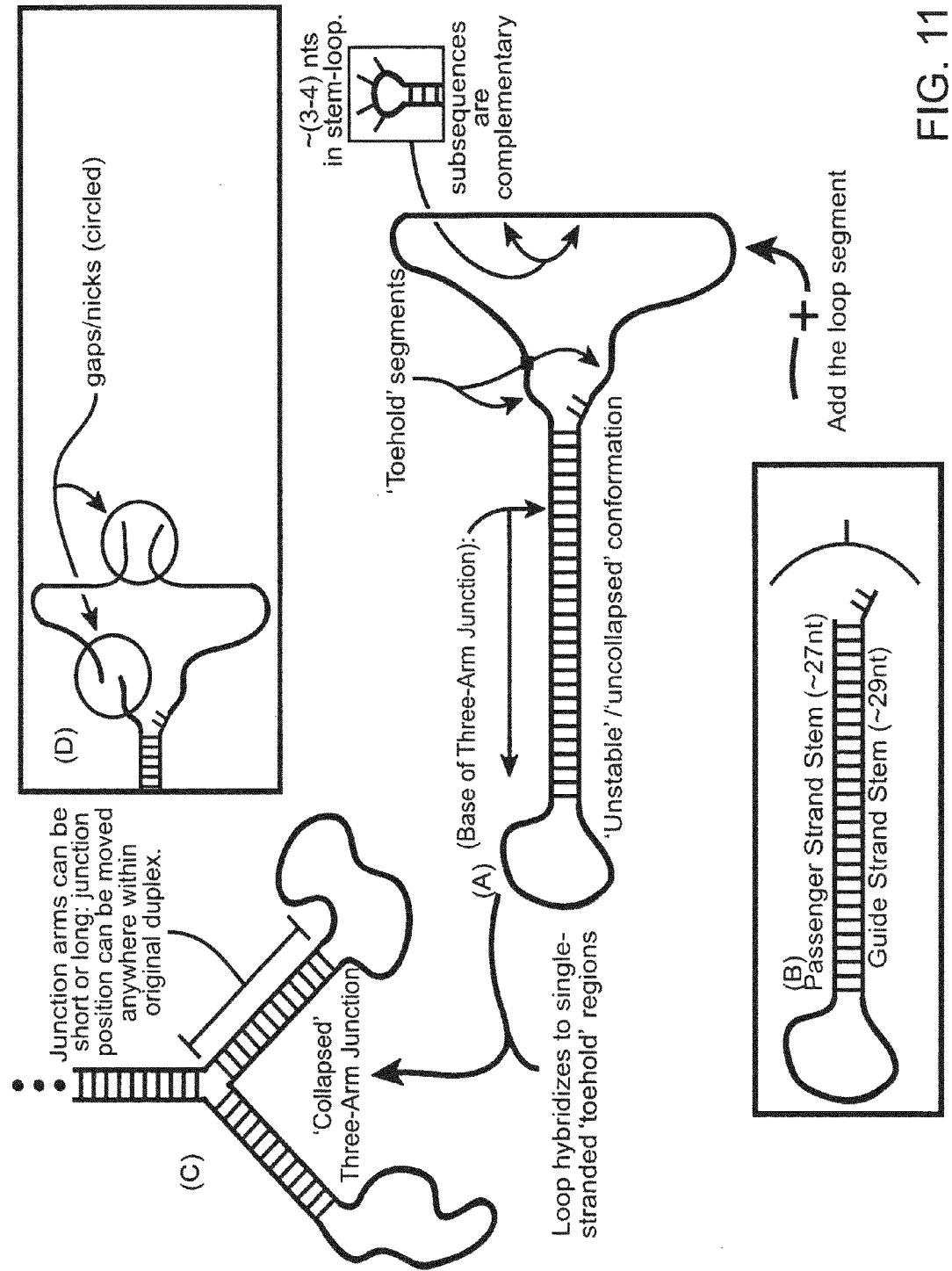

FIG. 11, panels A-D, shows an exemplary embodiment of the conversion of a nucleic acid duplex into a "collapsed" three-arm junction. FIG. 11, panel A, shows the "unstable" or "uncollapsed" conformation where attached loop has not yet formed three-arm junction. Subsequences (indicated by a double arrowhead at the far right) are complementary and can hybridize. However, due to steric constraints, they must form a hairpin with ~(3-4) nucleotides in the stem-loop (inset) and weakened stacking interactions between bases. If a nick/gap is present at the point between the subsequences, three-arm junction formation will usually still occur, since the four-arm junction alternative is energetically less favorable. "Toehold" segments (labeled) for stabilizing three-arm junction may be as short as ~(2-3) nucleotides or may be arbitrarily long. At the base of the three-arm junction (labeled), the position indicated with an arrow (pointing downwards) can be moved arbitrarily far into duplex (arrow pointing left).

FIG. 11, panel B, shows duplex stem formed by a passenger strand (~27 nucleotides) and guide strand (~29 nucleotides). A perfectly paired duplex may be used, or, alternately, a duplex with wobble-pairs and/or mismatches at one end of the duplex may be chosen. Pictured here is a perfectly paired stem for a 27 nucleotides shRNA with a 2-nucleotide toehold. A loop segment (indicated directly above with (+)-arrow) may be added to the end of the duplex stem where the three-arm junction should be formed. Matching shades indicate complementary subsequences. The loop hybridizes to single-stranded "toehold" regions at base of stem and duplex segments, creating a three-arm junction as shown. Matching colors indicate complementary subsequences. Partial hybridization to toeholds can create a four-way junction that is less energetically favorable than the "collapsed" three-arm junction. Instability elements (wobble pairs/mismatches) can be used to facilitate three-arm junction formation, as necessary.

FIG. 11, panel C, shows the "collapsed" three-arm junction. Junction arms can be as short as a few nucleotides as well as arbitrarily long: junction position can be moved anywhere within original duplex (top, vertically-positioned duplex).

FIG. 11, panel D, shows the possible presence of certain gaps/nicks (circled). Gap or nicks may affect the thermodynamics of the three-arm junction, but will not prevent its formation of the 'toehold' regions are a few nucleotides long. "Toehold" regions may be as short as ~(2-3) nucleotides in length, or may be arbitrarily long in all cases.

Figure 12:
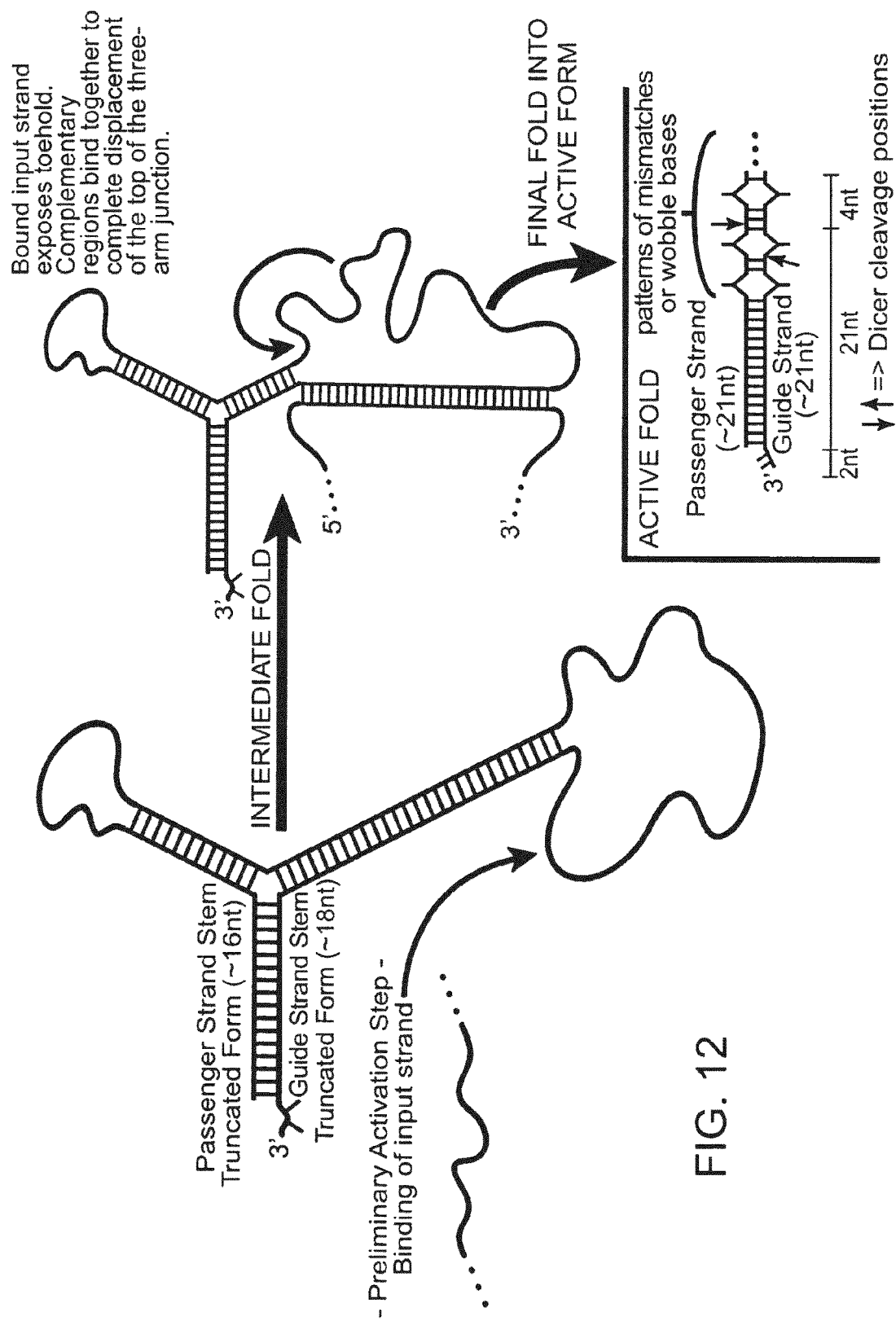

FIG. 12 shows an exemplary embodiment of the signal activated (sa)RNAi—Telescoping Platform with full input sequence independence. Labels identify the passenger strand stem in the truncated form (~16 nucleotides) and the guide strand stem in the truncated form (~18 nucleotides). Activation steps are first initiated by binding of the input strand to the signal-detecting region (arrow) on the construct. The inputs may comprise probe outputs, mRNA, miRNA or any molecule, either alone or in combination. Binding of the input strand displaces the signal-detecting strand on construct. This is the first step for (sa)RNAi activation. The length of the signal-detecting region can be adjusted as desired to allow for arbitrary mRNA/etc. Specificity, in certain embodiments, the total length may be less than <30 nucleotides. In other embodiments, where the signal-detecting region is 30 nucleotides or longer, wobble bases may be used every ~4-8 nucleotides to avoid a PKR response. The loop is shown topologically closed, thus Dicer should not be able to cleave the long stem. Since this initial branch-migration step does not completely displace top of three-arm junction, wobble bases can be used in the stem that is continuous with the signal-detecting sequence. Wobble bases may be used at some frequency such that the input strand has fewer wobble-pairings than the displaced segment. This will: (1)—continue to block premature activation, (2)—increase the energetic favorability of the displacement reaction, and (3)—facilitate making the resulting intermediate state of the construct kinetically inert until it refolds into the ACTIVE conformation.

The intermediate fold shows that, after input strand binding step, complex refolds into intermediate conformation. The bound input strand exposes toehold sequences (located at both ends of arrow). Complementary regions can now bind together to complete displacement of the top of the three-arm junction.

The active fold is shown in the bottom. In this conformation, the molecule may be processed by Dicer/RLC. The passenger strand shown is ~21 nucleotides. The guide strand shown is ~21 nucleotides. There is a 3' overhang comprising 2 nucleotides, and the total length of the duplex region is ~28 nucleotides, which includes ~21 nucleotides from the passenger strand paired to complementary sequences in the guide strand, and 7 additional nucleotides paired with complementary base pairs. Other patterns of mismatches/ wobble bases can be used so long as they allow for initial three-arm junction configuration. Small arrows indicated the Dicer cleavage sites.

Figure 13:
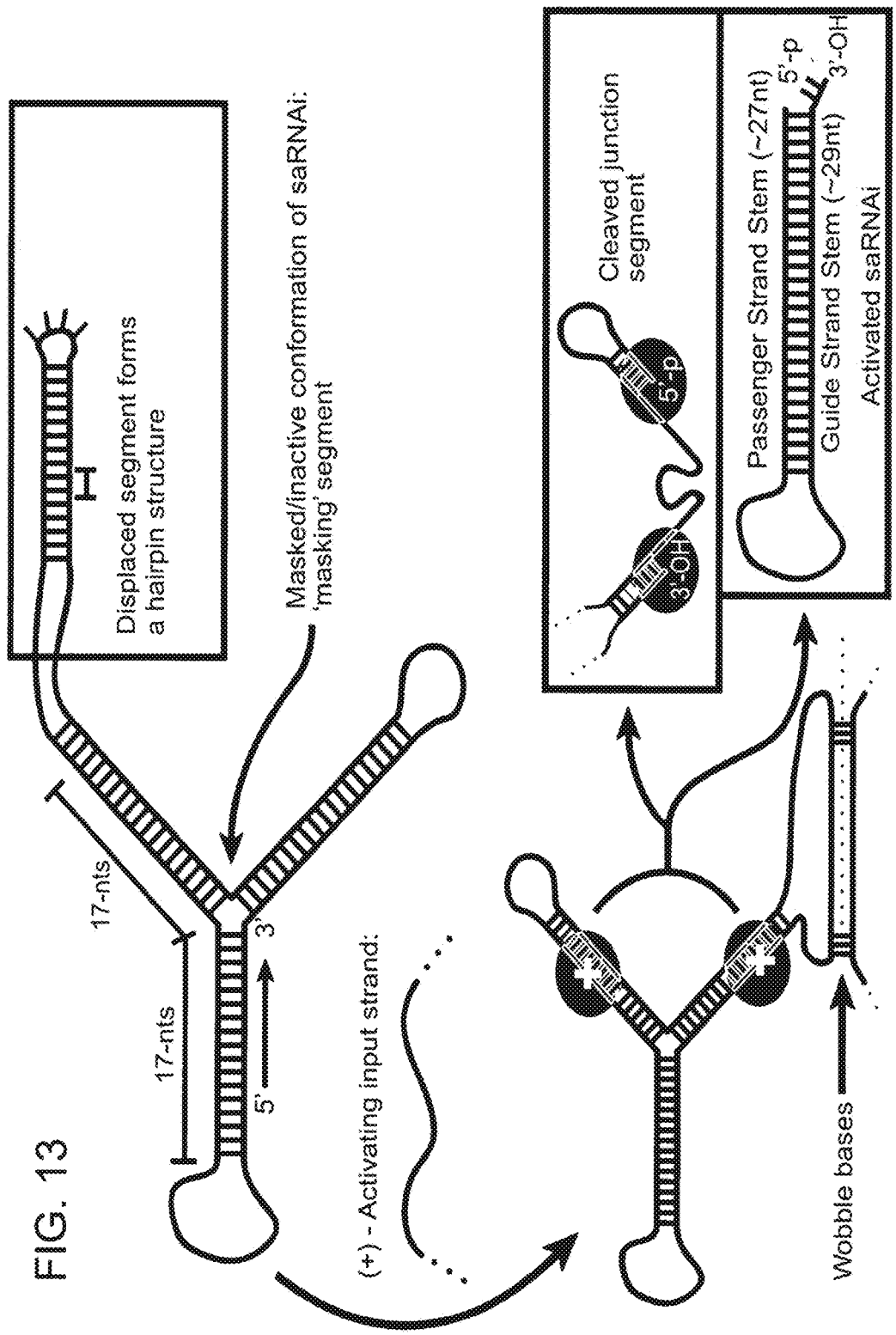

FIG. 13 shows an exemplary embodiment of the reversibly-cyclized saRNAi (RC-saRNAi)—RNase H mechanism with masking gate. Top left shows an (+)-activating input strand, with 5' to 3' direction and number of nucleotides in each branch indicated. In the inactive, masked conformation of the saRNAi, the "masking" segment (labeled) may be all-RNA or consists or other modified bases that block RNase H processing of construct. If an input RNA, such as mRNA, miRNA, or other exemplary inputs as described in the present disclosure, is present, the input will bind to toehold at loop and displace the "masking segment." The chimeric sequence (inset, top right) will bind with fewer total nucleotides than the "masking segment" and place DNA segments in a position to allow for appropriate RNase H processing. The top right inset shows that the displaced segment forms a hairpin structure where there is a 2 nucleotide overlap between the –5 nucleotide DNA segments. This ensures that no RNase H processing of the inactive construct will occur. Bottom left shows the conformation adopted when the input strand is bound to the "masking segment." Wobble bases can be used every ~4-8 nucleotides to avoid PKR/interferon response. The middle inset shows the cleaved junction segment, degradation by cellular exonucleases. Exonucleases are indicated in circles. The bottom right inset shows the activated saRNAi, capable of being cleaved by Dicer or loaded into RISC. The passenger strand stem (~27 nucleotides) and guide strand stem (~29 nucleotides), are both labeled.

Figure 14:
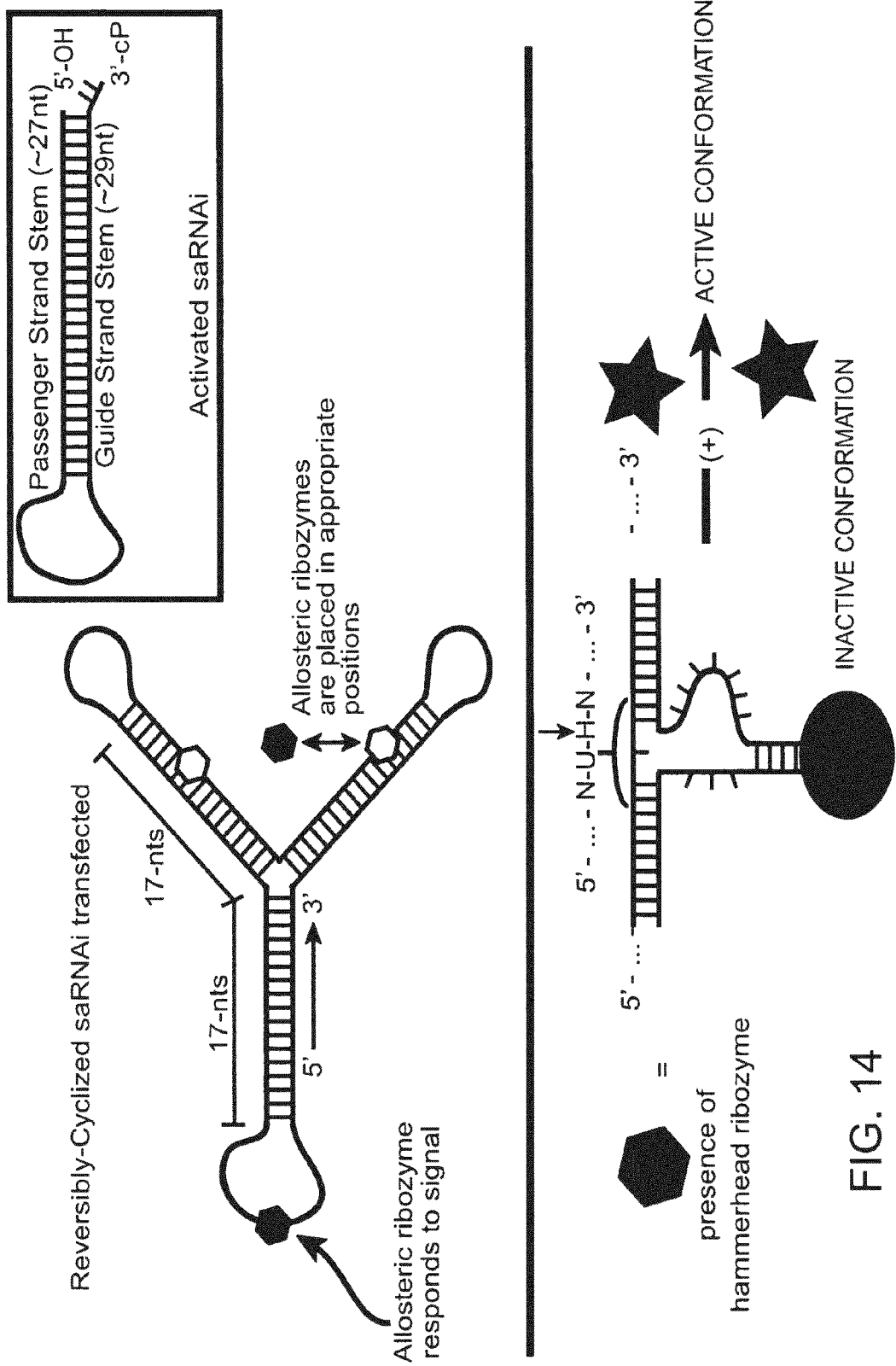

FIG. 14 shows an exemplary embodiment of the reversibly-cyclized saRNAi (RC-saRNAi)—allosteric ribozyme AND/NOT Gate implementation. Top left shows that the reversibly-cyclized saRNAi is transfected. Transfection may be performed by methods known in the art, such as naked injection, use nanoparticles, liposomes. In some embodiments, allosteric ribozymes may be designed such that their activating factors are not present in the extracellular serum/blood plasma. In these embodiments, like the RNase H version, allosteric ribozymes may be highly resistance to serum 3'/5' exonucleases. The left side shows allosteric ribozyme which responds to signal binding (hexagon). In some embodiments, the ribozyme is a NOT gate or potentially a "clock." Thus, if it is activated before the AND gate ribozymes, cellular exonucleases (3'/5') will degrade and inactivate saRNAi construct without Dicer processing/RISC loading. The right shows that the allosteric ribozymes are placed in appropriate positions so that they create an AND gate where BOTH need to be activated in order to generate a Dicer-cleavable/RISC-loadable construct. In some embodiments, Dicer needs a properly cleaved duplex (inset, top right). As indicated (LEFT), the same signal can be integrated or two different signals can be used. Here, the lighter shaded signal that activates the ribozyme is replaced by a dark shaded signal. (one 'yellow'-activated ribozyme is replaced by a 'pink'-activated ribozyme). The top right inset shows an activated saRNAi. Labels indicated the passenger strand stem (~27 nucleotides) and guide strand stem (~29 nucleotides). The cleaved region from the reaction shown at left is thermodynamically unstable, dissociating to create a Dicer-processible and RISC-loadable construct. The region near at the 5' and 3' of the duplex may contain wobble-pairs, mismatches, etc. to promote initial junction formation. Typical allosteric ribozyme OFF to ON catalytic rates range from $10^{-2}$-$10^{-4}$ min$^{-1}$ to ~$10^{-1}$-1 min$^{-1}$. The AND gate squares this, allowing for $10^{-4}$-$10^{-8}$ min$^{-1}$ OFF rates and $10^{-2}$-1 min$^{-1}$ ON rates. Bottom left shows "H" which represents any base but guanosine. The hexagon represents the presence of a hammerhead ribozyme, while a given fill or shading represents a unique "activator" small molecule, protein, etc. Multiple fills on different ribozymes allow for signal integration of various factors to create AND gates for the above construct. Bottom center shows the inactive conformation. Here, the hammerhead ribozyme is misfolded. The scissile phosphate (indicated by black arrow) is not cleaved. Bottom right shows the active conformation. Cleavage of scissile site leaves a cyclic 2',3' phosphodiester on the 3' end and a 5' hydroxyl (—OH) group. The 5' hydroxyl will quickly be phosphorylated by a cellular kinase and neither end groups will effect Dicer processing or RISC loading.

Figure 15:
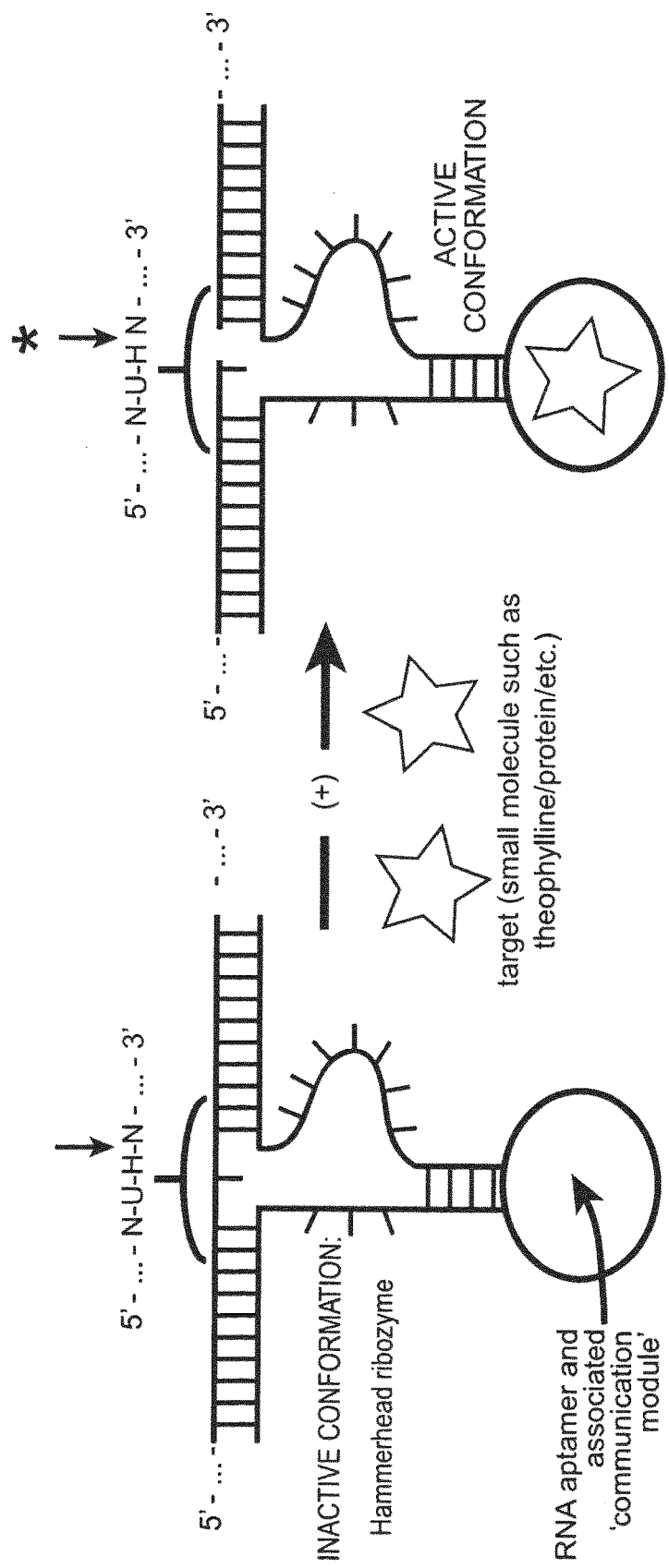

FIG. 15 shows an exemplary embodiment of the trans-cleaving allosteric hammerhead ribozyme. Top left shows a hammerhead ribozyme. "H" represents any base but guanosine. In the inactive conformation, hammerhead ribozyme is misfolded. Scissile phosphate (indicated by black arrow) not cleaved. Arrow points to the RNA aptamer and associated "communication module" attached to Stem II of ribozyme (circle). Star shape shows the target, for example, a small molecule such as theophylline, a protein, etc. The target binds the RNA aptamer that is connected by a "communication module" (circle) to Stem II of the ribozyme. The ribozyme refolds into active conformation (right). Cleavage of scissile phosphate (indicated by red arrow) occurs, leaving a cyclic 2',3' phosphodiester on the 3' end and a hydroxyl ('OH') group on the 5' end. Under normal physiological conditions, the RNA transesterification reaction is ~$10^{-7}$-$10^{-8}$ min$^{-1}$. The reaction leaves a cyclic 2',3' phosphodiester on the 3' end and a hydroxyl ('OH') on the 5' end. On an shRNA/siRNA, a cyclic 2',3' phosphodiester on the 3' end will not affect either dicer processing or RISC loading. The 5' hydroxyl will quickly be phosphorylated in vivo by a cellular kinase, and will also not affect dicer processing or RISC loading. (Adapted from: Li and Breaker, J Am. Chem. Soc. 121: 5364-5372, 1999).

Figure 16:
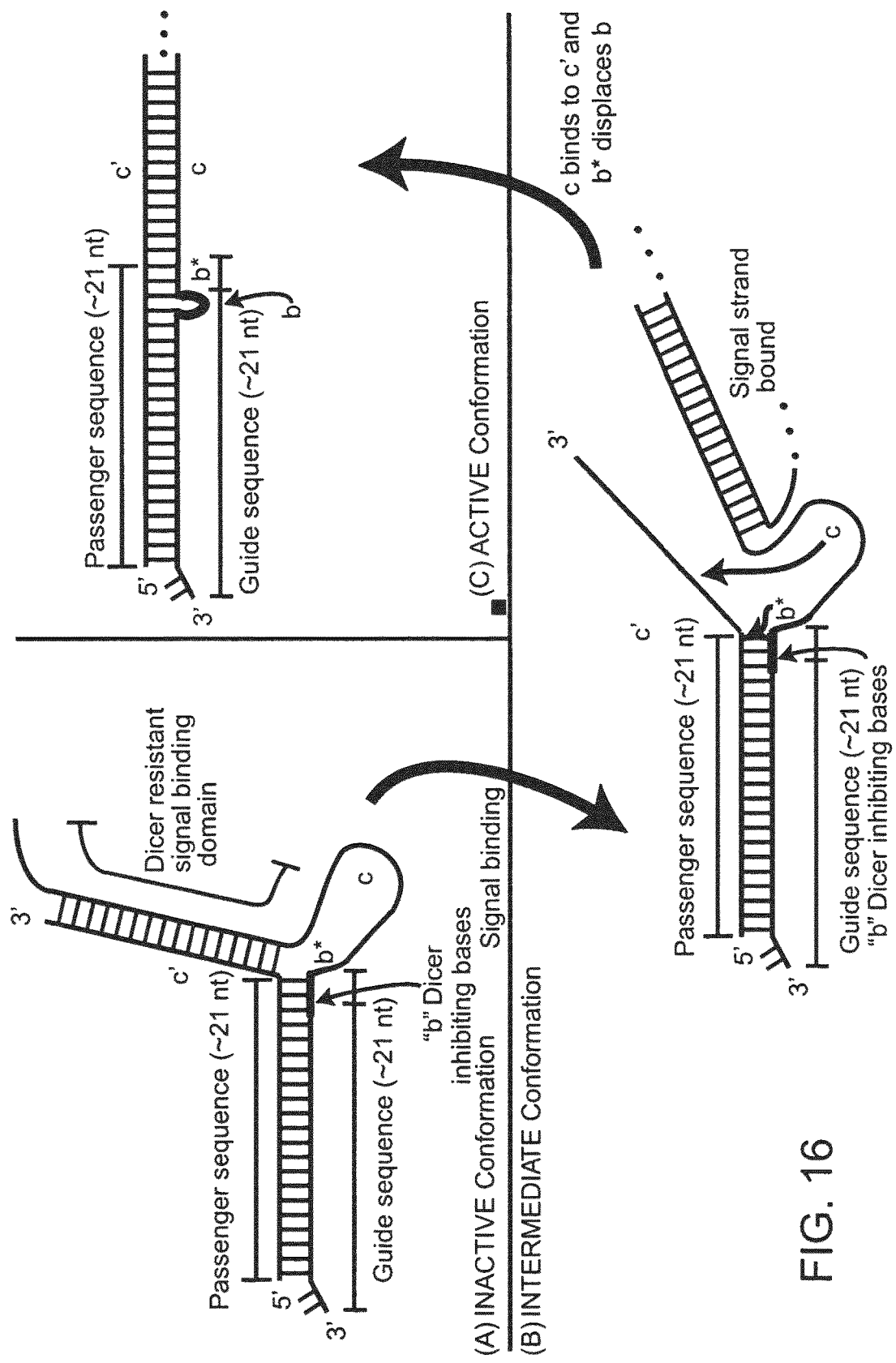

FIG. 16, panels A-C, shows an exemplary embodiment of the reverse chimera mask. FIG. 16, panel A, shows its inactive conformation. The passenger sequence (~21 nucleotides) and the guide sequence (~21 nucleotides) are labeled. The region labeled "b" comprises Dicer inhibiting bases. In some embodiments, region b comprises ~3 bases of DNA. The DNA bases are used to protect a substrate that is otherwise long enough for Dicer cleavage. The signal-binding domain is Dicer-resistant. FIG. 16, panel B, shows the intermediate conformation. Here, the input (or signal) strand has bound to the signal-detecting region. With the signaling strand in place, region c binds to c'. Region c establishes a toehold previously occupied by the signal-detecting strand. Because region b is DNA, and b* is RNA, and because RNA:RNA binding is more stable than DNA:RNA binding, then b* displaces region b. FIG. 16, panel C, shows the active conformation. Region b* is now placed over Dicer cleavage positions. The construct is activated.

Figure 17A:
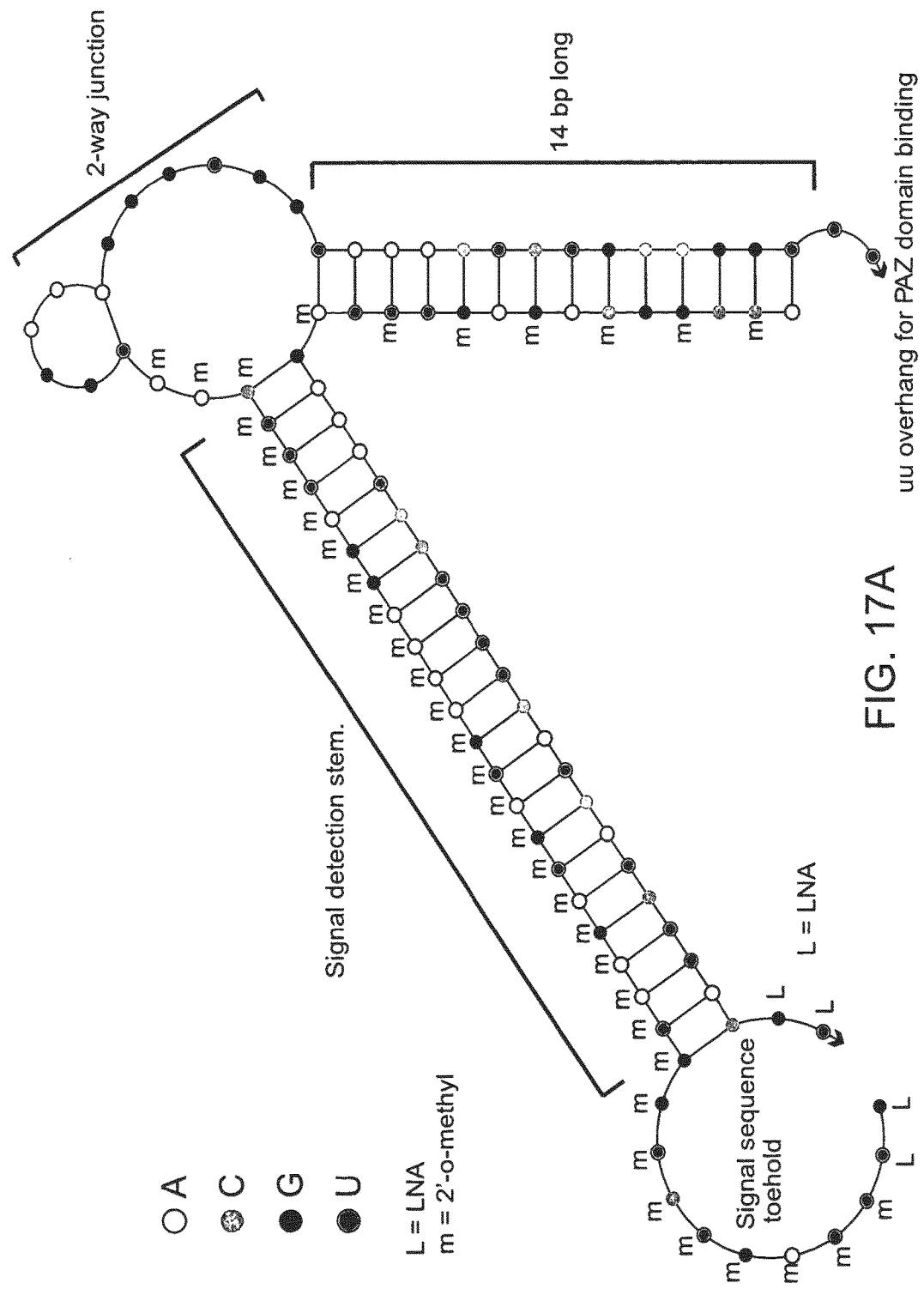

FIGS. 17A-B show an example of chimera mask with chemically modified bases. FIG. 17A shows the inactive conformation of a chimera mask with chemically-modified bases. In this figure, L=LNA, m=2'-o-methyl, while the bases are represented by the following colors: A (green), C (blue), G (black), U (red). Bottom left shows the signal sequence toehold. L=LNA, and help to prevent exonuclease degradation. Inverted-dT or DNA bases may also be used here. The modified bases may also discourage Dicer binding from this side. The center shows the signal detection stem.

This stem has been extensively modified with 2'-o-methyl bases (m) to prevent Dicer processing and immunostimulatory effects. Top right shows the 2'-o-methyl modifications that help resist endonucleases. A 2-way junction has been engineered into the molecule, although modified bases are not present on segments that will help form the activated Dicer cleavage site. Right center shows a duplex stem which is only 14 bp long because the overlap between the signal and target sequences gives flexibility to extend the signal detection stem. Notably, the targeting stem is considerably less well-protected than the signal detection stem. This design biases this side of the molecule toward degrading first. Here, the guide sequence has no modified bases whatsoever. Bottom right shows that the UU overhang has been engineered for PAZ domain binding. FIG. 17B shows the active conformation. Horizontal lines mark likely Dicer cleavage sites. Right, the stem area is bound to the mRNA signal sequence. The extensive 2'-o-methyl modifications should prevent Dicer processing of this sequence. Since 2'-o-methyl protects against PKR activation, mismatches are not required here.

Figure 18:
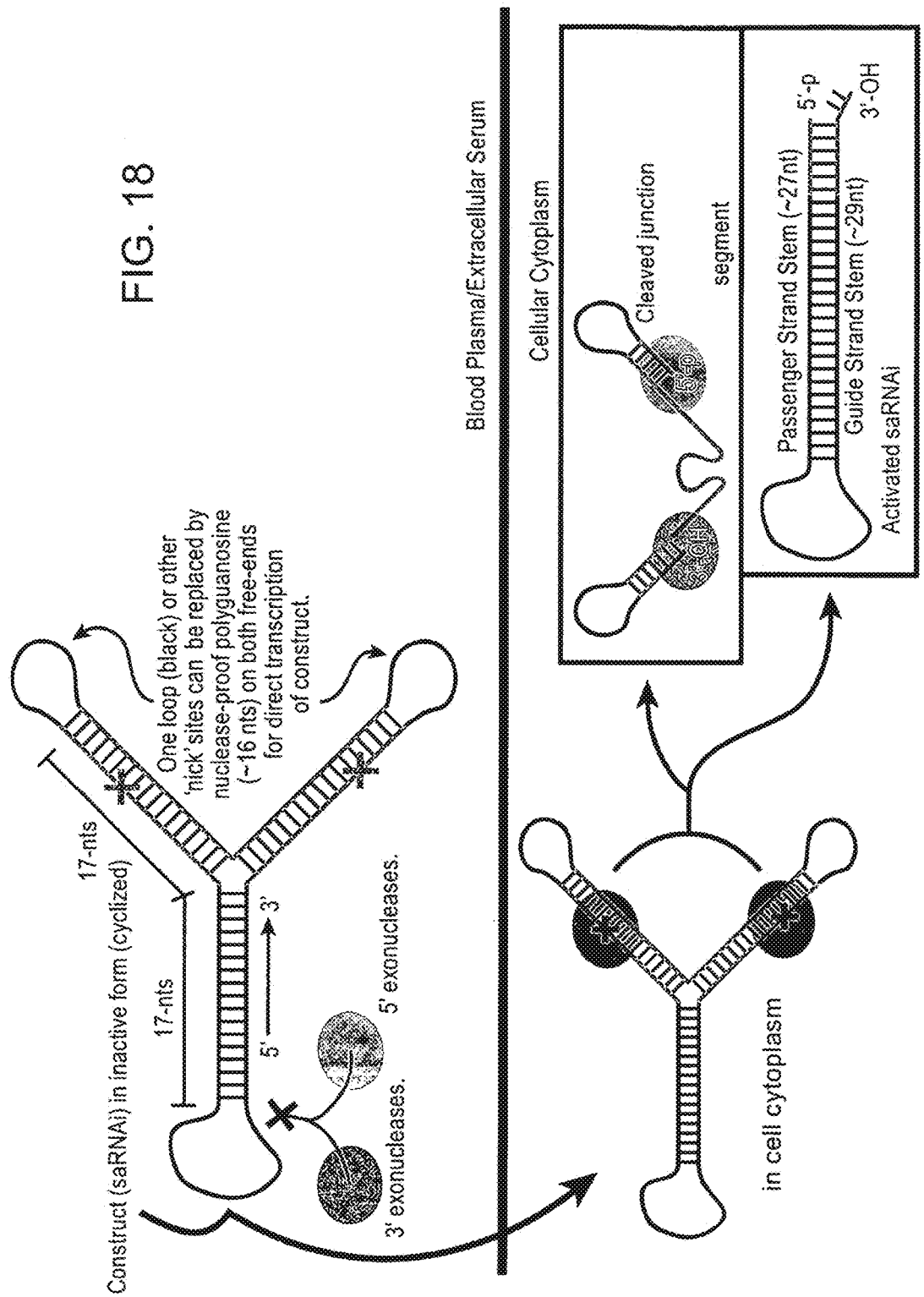

FIG. 18 shows an exemplary embodiment of the reversibly-cyclized saRNAi (RC-saRNAi)—RNase H mechanism. Top shows the saRNAi construct in blood plasma or extracellular serum. This construct is a covalently circularized "collapsed" three-arm junction with chimeric base composition. Top left shows that the saRNAi construct is delivered in inactive form (cyclized) to a given cell-type via any transfection method. Exemplary transfection methods comprise naked injection of RNA or make use of nanoparticles, liposomes, etc. Lack of serum RNase H activity and covalent circularization allows for long "unshielded" exposure times in serum with no degradation. Also shown are bases in main stem of saRNAi not participating in "collapsed" three-arm junction. Here, the 17 nucleotides are shown in the duplex region (left side, indicated by brackets and 17 nucleotides label), but this region may be as short as a few nucleotides or may be arbitrarily long. In other embodiments, this region can be all-RNA or have modified nucleotides. Covalent circularization (or polyguanosine (>9 nucleotides) on free-ends) confers extreme serum stability to the construct by blocking the initiation of serum exonucleases. Here, the light sphere represents 3' exonucleases, and the dark sphere represents 5' exonucleases. Top center shows one loop or other "nick" sites (arrows) can be replaced by nuclease-proof polyguanosine (~16 nucleotides) on both free-ends for direct transcription of construct. Lighter-shaded duplexes represent potentially all-RNA bases which participate in the junction structure. Bases in these regions can also be modified nucleotides. Here, 17 nucleotides are shown in these regions, but this region can be as short as a few nucleotides or may be arbitrarily long. Section can be all-RNA or have modified nucleotides. The main stem of the saRNAi construct (black duplex, left side of molecule) would need to be longer to compensate for the length of the junction and vice versa. Top right shows ~5 nucleotides DNA sequences that direct RNase H cleavage at 3'-most site on complementary RNA subsequence are pictured near to the X. The cleavage site is indicated by "X." In some embodiments, these sequences can be slightly longer at the expense of deterministic cleavage by human RNase HI, H2, etc. Bottom left shows the saRNAi in the cellular cytoplasm. Once in cell cytoplasm, RNase H (spheres) acts as the "activating" signal for the saRNAi, reversing the cyclization via cleavage at the indicated sites (see X, beneath the spheres). RNase H leaves a 5' phosphate (5'-p) and a 3' hydroxyl (3'-OH) terminus (bottom, box on upper right). Dicer cannot bind/process an uncleaved 'inactive' cyclized construct. The cleaved junction segment undergoes degradation by cellular exonucleases. Bottom right (lower box) shows that the activated saRNAi construct has a passenger strand stem (~27 nucleotides) and a guide strand stem (~29 nucleotides). The activated saRNAi may be cleaved by Dicer and/or loaded into the RISC complex.

Figure 19:
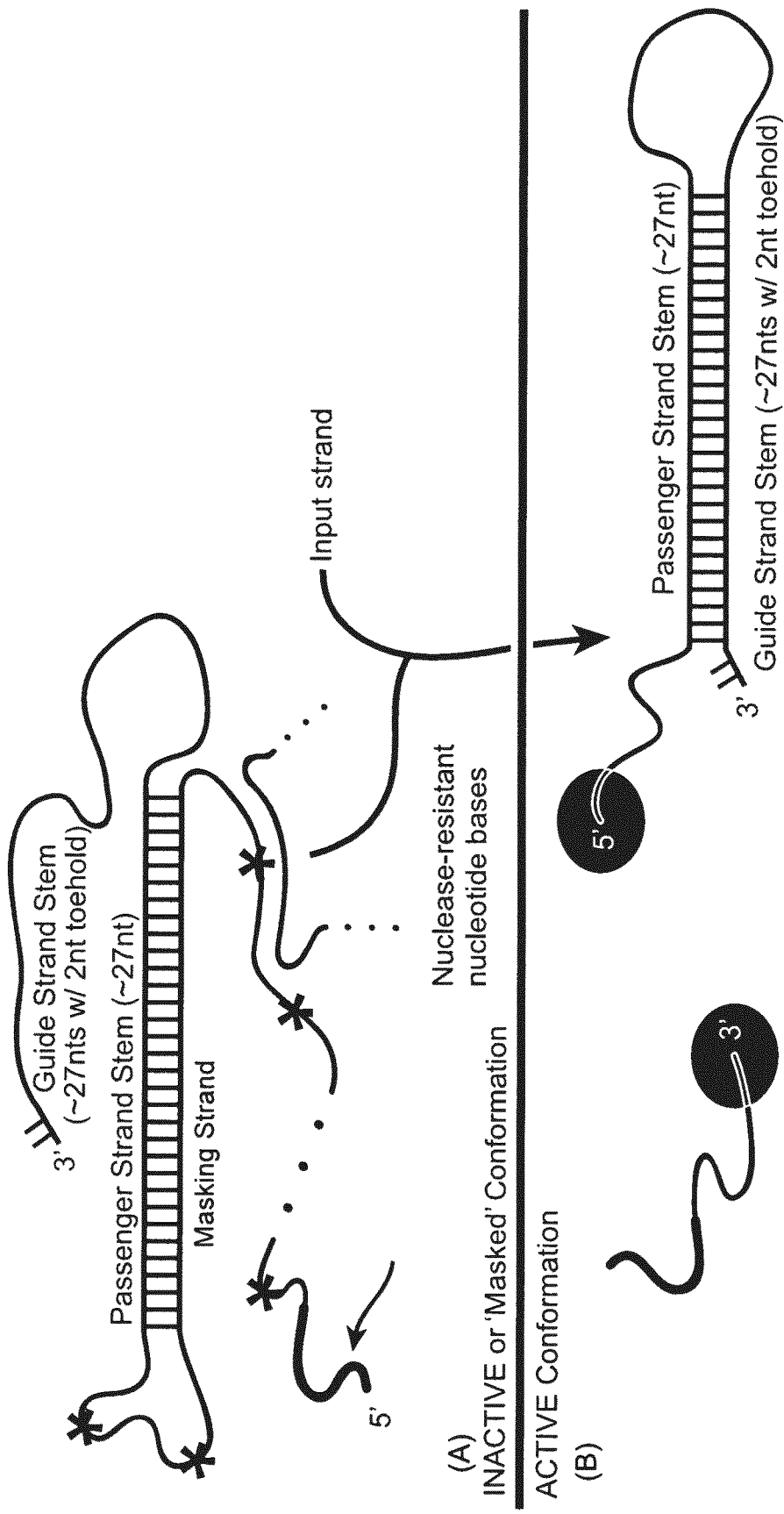

FIG. 19, panels A-B, shows an exemplary embodiment of the degradation-activated (sa)RNAi—alternative (5')-tail-based chimera-masking platform. FIG. 19, panel A, shows the inactive or "masked" conformation. In this conformation, the potentially 'Chimeric' "masking" strand (labeled) displaces the guide strand. The length of the masking segment may be adjusted, and may comprise DNA, RNA, etc., or may have some other nuclease processible base composition. To displace the guide strand, the masking strand may bind to nucleotides in the ACTIVE form's shRNA stem loop that is found in the active conformation. If the masking strand is not RNA, it will completely block Dicer cleavage, since Dicer requires a dsRNA duplex at the cleavage position(s). If the sequence is RNA, Dicer cleavage will be blocked by long 3'/5' extensions. In some embodiments, these extensions may be preferable to long extensions on 5' or 3' end only.

The input strand binds and induces cleavage of complementary sequence which can be RNA/etc. (see asterisk where input strand has bound to the saRNAi construct). The input strands may be DNA or RNA, or miRNA as the system may be autocatalytic. An RNase H mechanism may be used for bound DNA and an Ago2 mechanism may be used for miRNA. In some embodiments, this scheme also allows for any allosteric ribozyme. In some embodiments, the allosteric ribozyme may be on the strand near to the asterisks, and may be cis-acting. In other embodiments, the cleavage may be induced by a nucleic acid binding event and/or the binding of any other factor. One exemplary factor is TAA. Here, only a single binding site is shown, but many more can be encoded on extended 5' tail to make an N-OR gate for saRNAi activation (see asterisks). Also labeled is the single-stranded guide strand stem, which comprises ~27 nucleotides w/ 2-nucleotide toehold. The passenger strand stem comprises ~27 nucleotides. At the 5' end of the construct are nuclease-resistant nucleotide bases, of which there may be at least 9 nucleotides. Nuclease resistance may be conferred by use of polyguanosine (>9 nucleotides), DNA, 2'-OMe, or LNA, or forms of RNase resistant bases.

FIG. 19, panel B, shows the active conformation. Various processive exonucleases (circles labeled 3' and 5') digest cleaved segments but stop at the passenger strand stem. This can be accomplished in a variety of ways: (i) The passenger strand stem can have ribonuclease-unprocessible bases (2'-OMe/DNA/etc.). However, the 5' tail (labeled) should not comprise only RNA, because two Dicer cleavage events could occur and create an active RISC-loadable complex. (ii) Outside of a miRNA cleavage region, the single-stranded tail may comprise DNA, and the passenger strand stem may comprise RNA. Thus, exonucleases digest up to the stem and then, due to lack of a toehold, RNA exonucleases may take a long time to digest the now-active shRNA. Similarly, the duplex itself may be sufficient to halt digestion. (iii) Variants of (i) and (ii) may be envisioned, where nucleotide-type switching/linkage-switching (possibly 2')/blocking agents halt exonucleases at passenger strand stem. Bottom right shows that the saRNAi construct is active once the 5' end is sufficiently truncated to allow for RISC loading after a Dicer cleavage event. Dicer processing may occur before then, but cofactor that senses 5'-phosphate on passenger strand (e.g., R2D2/TRBP) blocks RISC entry if tail is not removed. In the active conformation, the passenger strand stem is ~27 nucleotides while the guide strand stem is ~27 nucleotides with a 2-nucleotide overhang.

Figure 20:
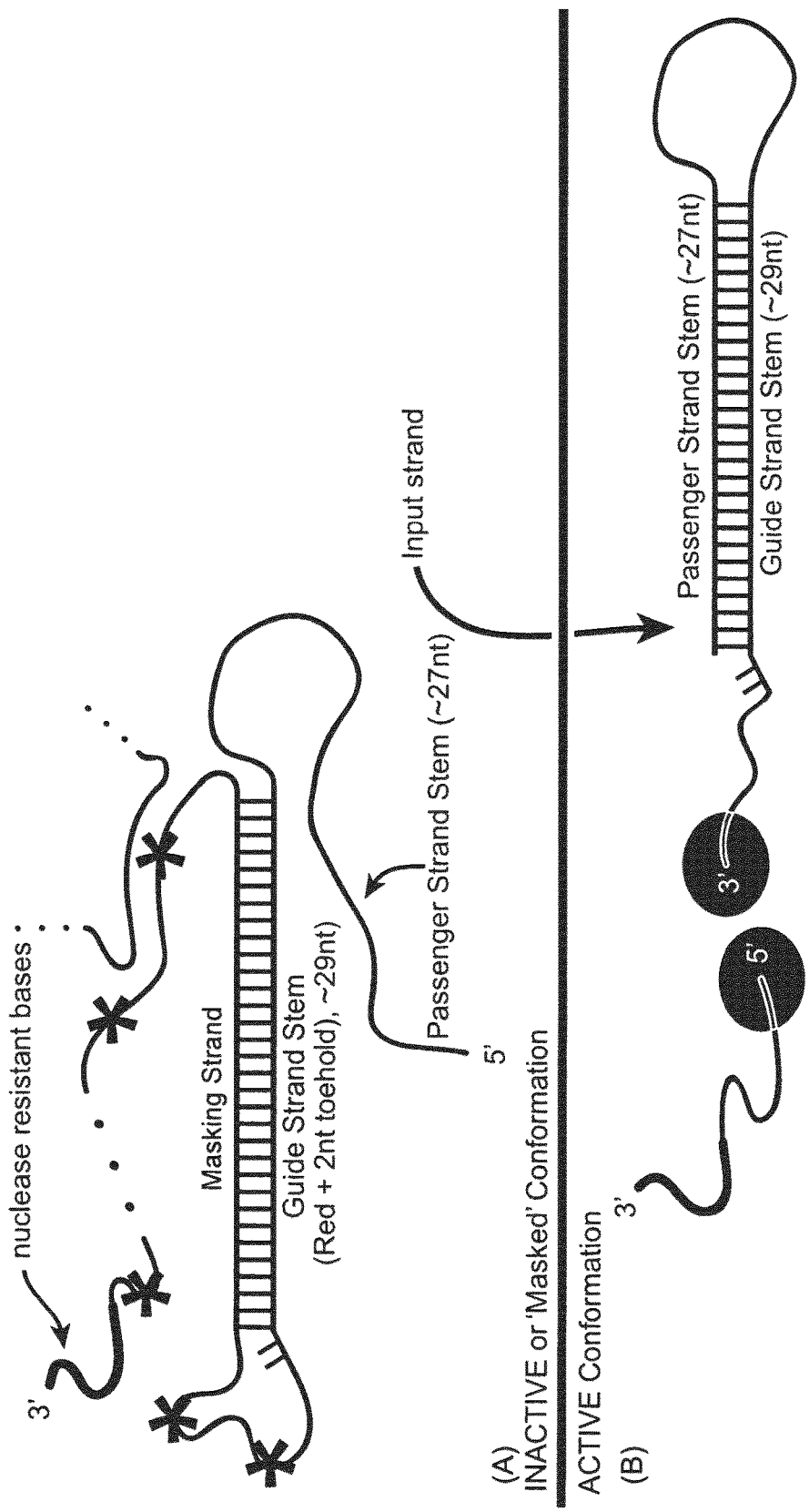

FIG. 20, panels A-B, shows an exemplary embodiment of the degradation-activated (sa)RNAi—alternative (3')-tail-based chimera-masking platform. FIG. 20, panel A, shows the inactive or "masked" conformation. In the inactive or "masked" conformation, the "masking" strand (labeled) displaces the guide strand. The length of the masking segment may be adjusted, and may comprise DNA, RNA, etc., or may have some other nuclease processable base composition. To displace the guide strand, (length of masking segment can be adjusted and toehold can also be covered—not shown) the masking strand may bind to nucleotides in the shRNA stem loop that is found in the active conformation. If the masking strand is not RNA, it will completely block Dicer cleavage, since Dicer requires a dsRNA duplex at the cleavage position(s). If the sequence is RNA, Dicer cleavage will be blocked by long 3'/5' extensions. In some embodiments, these extensions may be preferable to long extensions on 5' or 3' end only. The input strand binds and induces cleavage of complementary sequence which can be RNA, etc. (see asterisk where input strand has bound to the saRNAi construct). The input strands may be DNA or RNA, or miRNA as the system may be autocatalytic. An RNase H mechanism may be used for bound DNA and an Ago2 mechanism may be used for miRNA. In some embodiments, this scheme also allows for any allosteric ribozyme. In some embodiments, the allosteric ribozyme may be on the strand near to the asterisks, and may be cis-acting. In other embodiments, the cleavage may be induced by a nucleic acid binding event and/or the binding of any other factor. One exemplary factor is TAA. Here, only a single binding site is shown, but many more can be encoded on extended 5' tail to make an N-OR gate for saRNAi activation (see asterisks). Also labeled is the single-stranded guide strand stem, which comprises ~27 nucleotides w/ 2-nucleotide toehold. The passenger strand stem comprises (~27 nucleotides). At the 3' end of the construct is the signal-detecting strand, capped by at least 9 nuclease-resistant nucleotide bases. Nuclease resistance may be conferred by use of polyguanosine (>9 nucleotides), DNA, 2'-OMe, or LNA, or forms of RNase resistant bases.

FIG. 20, panel B, shows the active conformation. Various processive exonucleases (circles labeled 3' and 5') digest cleaved segments but stop at the passenger strand stem. This can be accomplished in a variety of ways: (i) The guide strand stem can have a few ribonuclease-unprocessible bases (2'-fluoro, etc.) that still allow for RISC loading. (ii) Outside of a miRNA cleavage region, the single-stranded tail may comprise DNA, and the passenger strand stem may comprise RNA. Thus, exonucleases digest up to the stem and then, due to lack of a toehold (ssRNA initiation), RNA exonucleases may take a long time to digest the now-active shRNA. Similarly, the duplex itself may be sufficient to halt digestion. (iii) Variants of (i) and (ii) may be envisioned, where nucleotide-type switching/linkage-switching (possibly 2')/blocking agents halt exonucleases at the toehold or the stem of the guide strand. Bottom right shows that the saRNAi construct is active once the 3' end is sufficiently truncated to allow Dicer processing, when the 3' end fits in PAZ domain. Dicer processing should not be able to occur before then due to short (~27 nucleotides) stem, which can be further truncated if necessary. If Dicer processing does occur, a long 3' tail should block RISC entry.

Figure 21A:
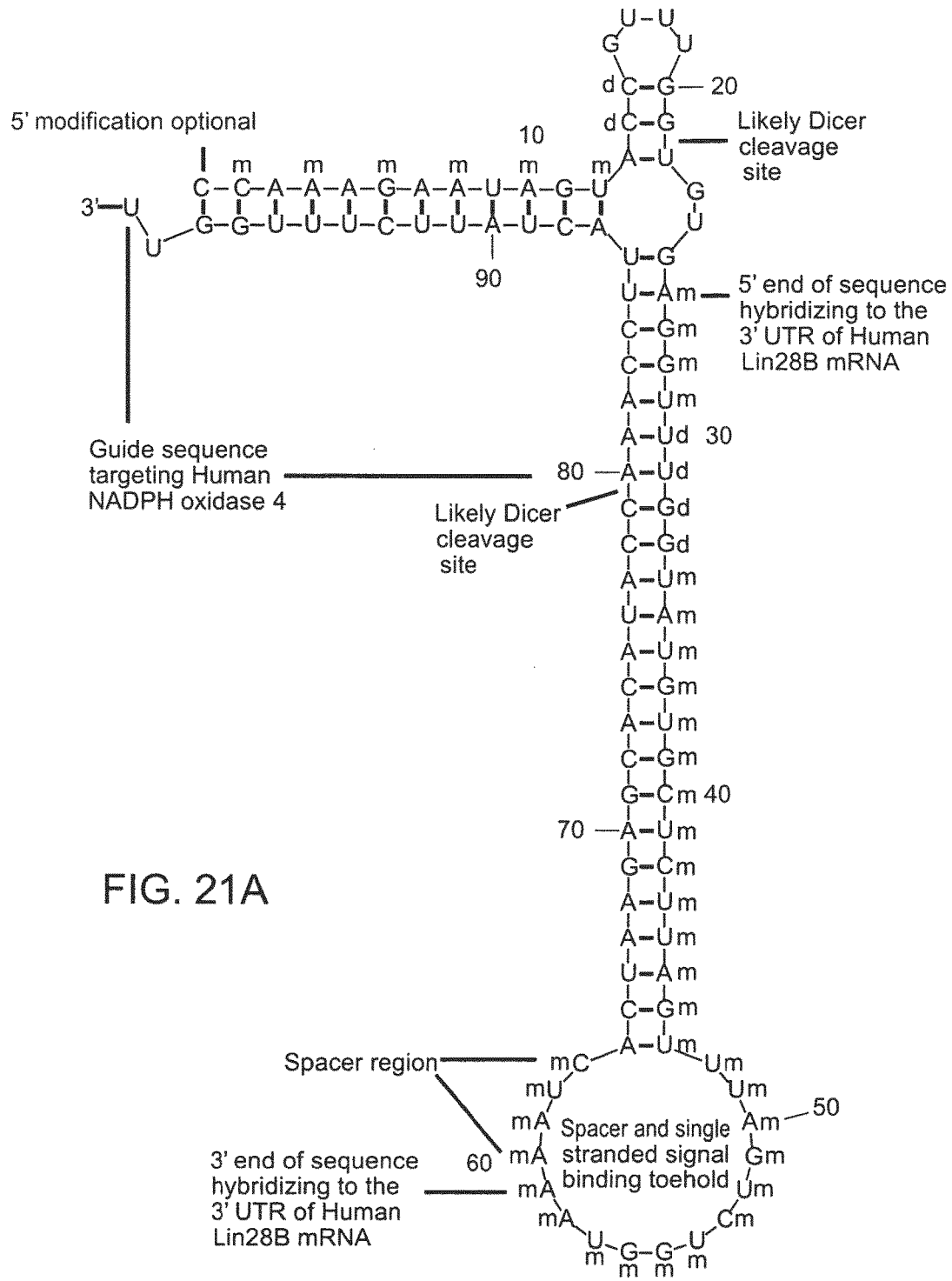
Figure 21B:
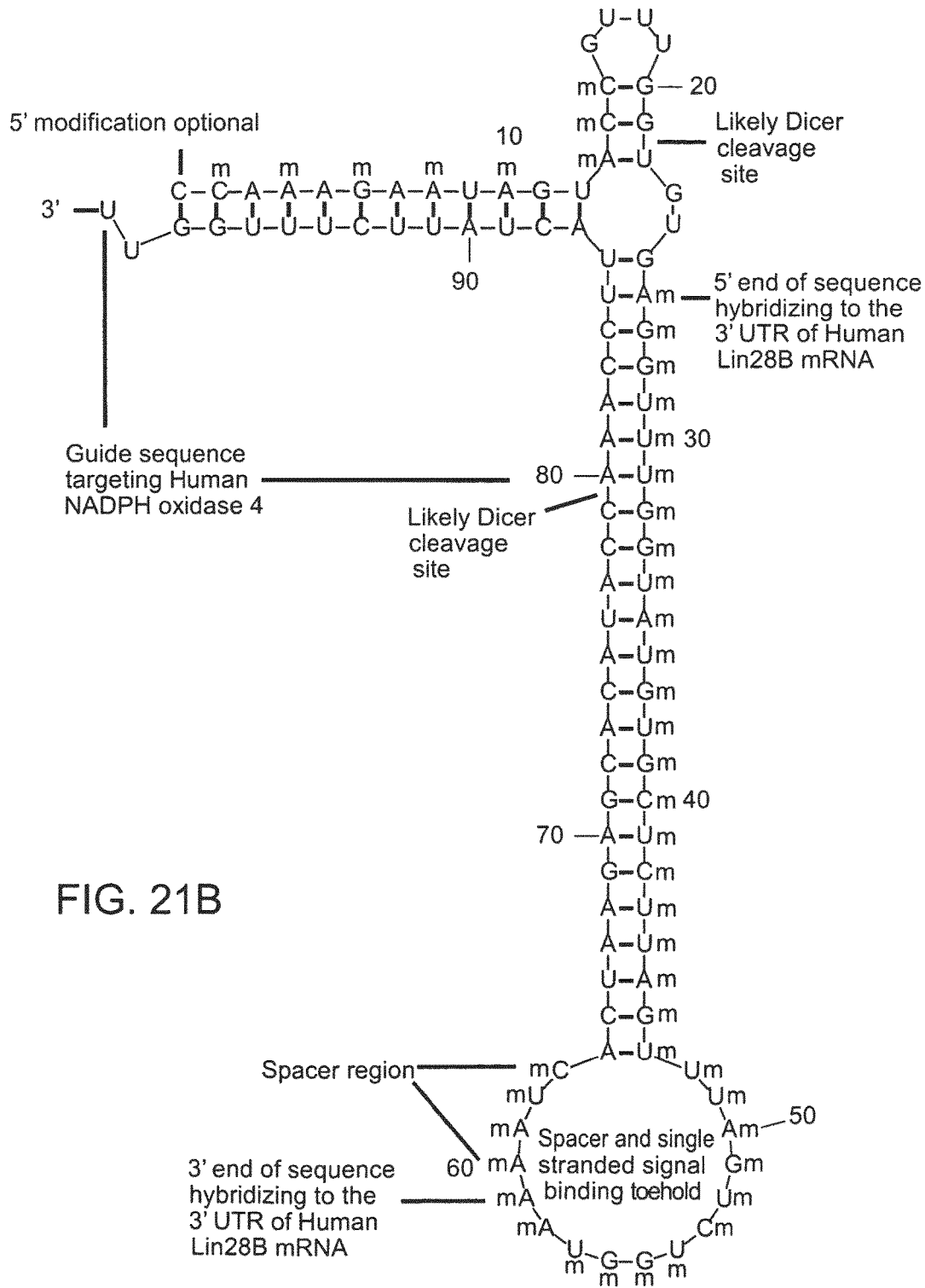

FIGS. 21A-B show an exemplary embodiment of the chimera-masking construct, inactive conformation, Human Lin-28b. FIG. 21A shows the inactive conformation. The 5' modification is optional. The guide sequence targets Human NADPH oxidase 4. Horizontal black lines indicate likely Dicer cleavage sites when the saRNAi construct is activated. Indicated on the sequence is the 5' end of sequence hybridizing to the 3' UTR of Human Lin28B mRNA. Spacer regions are labeled. The 3' end of sequence hybridizing to the 3' UTR of Human Lin28B mRNA. Bottom right shows, within in the loop structure, the spacer and single stranded signal binding toehold.

FIG. 21B shows an alternative embodiment, wherein certain DNA modification ("d") replace 2'-O-Me ("m") modification, see nucleotides #14, 15, 30, 31, 32, 33, and 34.

Figure 22:
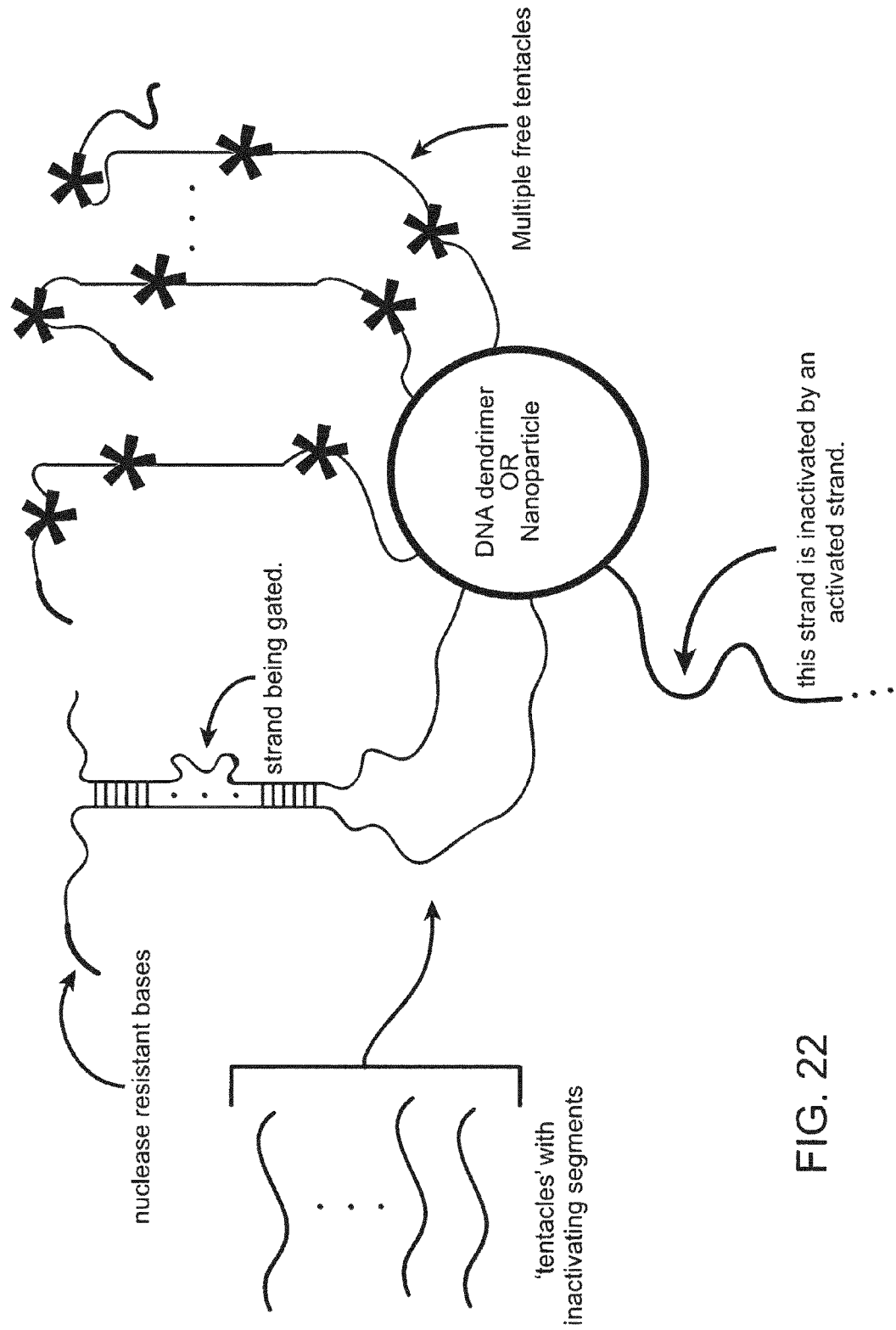

FIG. 22 shows an exemplary embodiment of the degradation-based N-Bit AND, N-Bit NAND, and concentration sensing gates, with dendrimeric or nanoparticle-based inactivating I activating strand implementation. The shown N-Bit AND or NAND gate comprises a series of "tentacle" structures (e.g., single-stranded polynucleotides). All tentacles need to be inactivated and/or degraded in order for lasting activation or lasting inactivation of the labeled strand. The labeled strand may be catalytic, antisense, masked miRNA, IRES on mRNA. Polyguanosine (>9 nucleotides) OR-2'-OMe/LNA/etc. nuclease resistant bases (labeled) may be used to block exonuclease degradation in the absence of signal polynucleotides. In the presence of the proper signal (e.g., signal polynucleotide), cleavage occur at the respective signal-activated cleavage points (labeled as asterisks), thus creating free 5' or 3' ends for exonuclease degradation.

In the NAND gate scheme, the tentacles are required for the labeled strand to be active. Alternately, activation of the labeled strand leads to the inactivation of a second strand (see arrow, bottom center). In some embodiments, the labeled strand may encode a ribozyme that, when active, cleaves and/or otherwise disables the second strand. If the tentacle currently bound to the labeled strand is degraded, high local concentration of other free tentacles ensure that another immediately binds on. Each tentacle has either a cleavage site (for a miRNA, allosteric cis-acting ribozyme, etc.) or can be bound and inactivated by a complementary nucleic acid segment (when bound to labeled strand, a toehold for branch migration will be presented).

Figure 9:
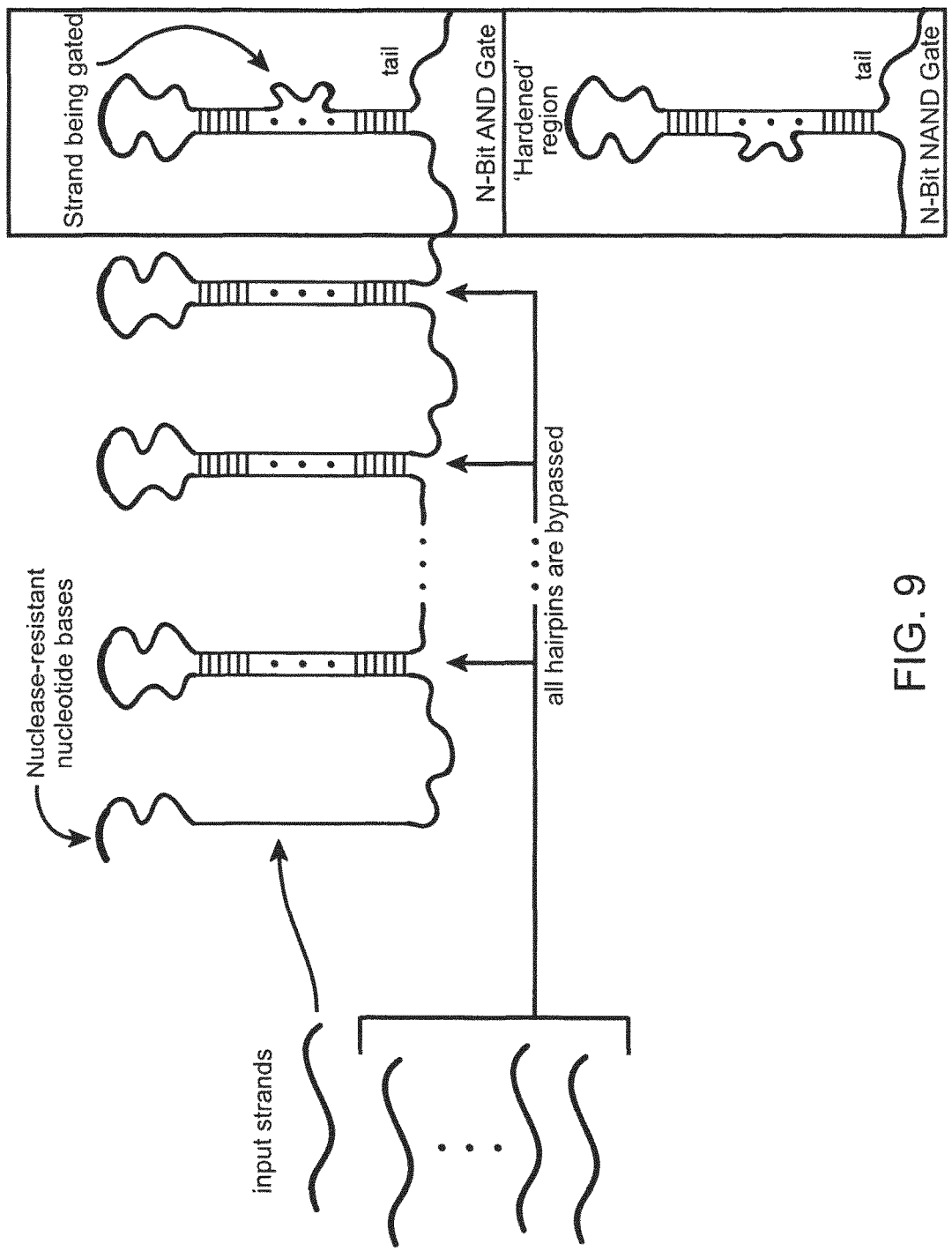
FIG. 9 shows an exemplary embodiment of the degradation-based N-AND, N-NOT, and concentration sensing gates. One of many possible input strands (DNA/miRNA/ribozyme (system can be autocatalytic)/etc.) binds at the indicated site and induces cleavage of complementary sequence which can be RNA (miRNA0/DNA/etc. RNase H mechanism for bound DNA & Ago2 mechanism for miRNA. Scheme also allows for any allosteric ribozyme (can be on red strand and cis-acting) where cleavage is induced by a nucleic acid binding event and/or the binding of some other factor (TAA. etc). The N-Bit AND/NAND gates may comprise a series of individual hairpins, which need to be bypassed sequentially if all N inputs are to be required for activation/inactivation of a function domain (catalytic, antisense, masked miRNA, IRES, etc., shown in the two boxes on the right). A series of input signals, such as signal polynucleotides, may sequentially bind to the hairpins in succession. Upon the binding of the first signal to the first hairpin, strand displacement may dissolve the next hairpin to form a new duplex region between the incoming signal and the signal detection sequence found in two adjacent hairpins. This structure may be cleaved by any one of the aforementioned mechanisms (RNase H, miRNA, cis-acting ribozymes, etc.). The cleavage results in the creation of free 5' or 3' ends that can be used to digest the cleaved strands by endo- and exo-nucleases, until the nucleases hit the next polyguanosine block (or other nuclease resistant modified nucleotides) in the next hairpin loop. In some embodiments, shortcuts where interlinking segments between hairpins are cut (or serve as branch migration toeholds) are used. Each time a hairpin is cut (and an exonuclease processed) or opened by branch migration, it releases a new cleavage site (for a miRNA, allosteric cis-acting ribozyme, etc.) or branch migration toehold for the next hairpin. The inputs may all be identical or may be different, and multiple different mechanisms (as described herein) can be used for bypassing a given hairpin or different hairpins. Exemplary mechanisms make use of miRNA, branch migration, cis-acting allosteric ribozyme, and more. The input strand (labeled) represents one of many possible input strands that bind and induce cleavage of complementary sequences. The input strands may be DNA or RNA, or miRNA, ribozyme, etc., and the system may be autocatalytic. An RNase H mechanism may be used for bound DNA and an Ago2 mechanism may be used for miRNA for the cleavage event. In some embodiments, this scheme also allows for any allosteric ribozyme. In some embodiments, the allosteric ribozyme may be on the strand near to the asterisks, and may be cis-acting. In other embodiments, the cleavage may be induced by a nucleic acid binding event and/or the binding of any other factor. One exemplary factor is TAA. In some embodiments, the saRNAi construct may bind to one or more inputs. In those embodiments where a multiplicity of inputs is used, the inputs can all be the same, all can be different, certain inputs can be encoded redundantly, and any other combinations or permutations that may be put into practice by one of skill in the art.

Inputs can all be the same or unique, and multiple unique inactivation I degradation inducing mechanisms can be used for each individual tentacle (miRNA, branch migration, cis-acting allosteric ribozyme, etc.). AND and NAND gates can both be present and compete (see FIG. 9 and its legend).

Center circle shows DNA dendrimer that may be a non-covalent or covalent (doublers, treblers, etc.) variety OR a nanoparticle, etc., which all the tentacles attach. For one potential NAND gate implementation, the second strand (lower left quadrant of center circle) can be a catalytic, antisense, masked miRNA, or IRES on an mRNA, and may be cut, bound, degraded or otherwise inactivated by an activated labeled strand. Multiple free tentacles can each have a unique sequence for hybridization based sequestering and/or each can have a unique cleavage-inducing signal (and potentially degradation inducing signal) for an allosteric cis-acting ribozyme, a unique miRNA recognition site, etc. Potential sites for cleavage are shown (asterisks) but, as in all other schemes, many additional ones are possible (additional asterisks). Since tentacle inactivation is target concentration dependent, for the AND gate the number of tentacles (or binding sites on tentacles) can set a "timer" that only goes off before the labeled strand is normally degraded if a certain target concentration is present. Likewise, for the NAND gate, the 'timer' can set the labeled strand's lifetime.

In some embodiments, the inputs may not need to bind and function in a sequential manner.

Figure 23:
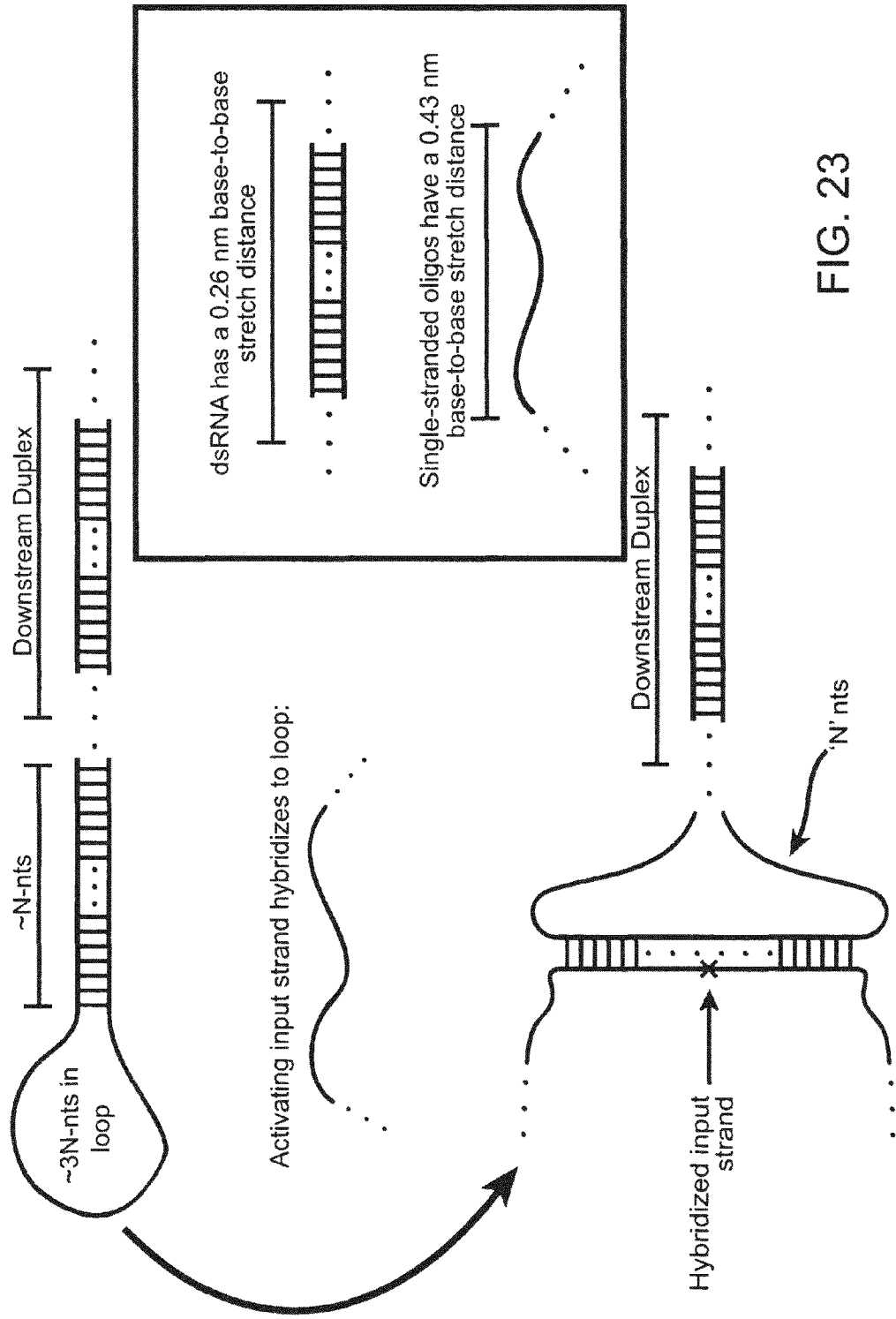

FIG. 23 shows an exemplary embodiment of the "Rip Loop" scheme. Top left shows the inactive conformation comprising ~3N nucleotides in loop, ~N nucleotides in one duplex, and a downstream duplex. Center left shows an activating input strand that hybridizes to the loop. Center right, box inset compares the stretch distances. dsRNA has a 0.26 nm base-to-base stretch distance (0.34 nm for dsDNA, 0.30 nm for DNA/RNA hybrids). Single-stranded oligos have a 0.43 nm base-to-base stretch distance. Bottom left shows the hybridized input strand (marked with "X") dissociates ~N base-pairs in immediately proximal stem by binding to ~3N nucleotides. More precisely, ~3.3N nucleotides should be bound when forming an RNA/RNA duplex, ~2.9N nucleotides for RNA/DNA and so on. Bottom center shows a downstream duplex that is labeled. "N" nucleotides on either side are now dissociated. Two dissociated "N" nucleotide oligos have a combined maximum stretch distance approximately 3 times longer than the original hybridized duplex.

Figure 24:
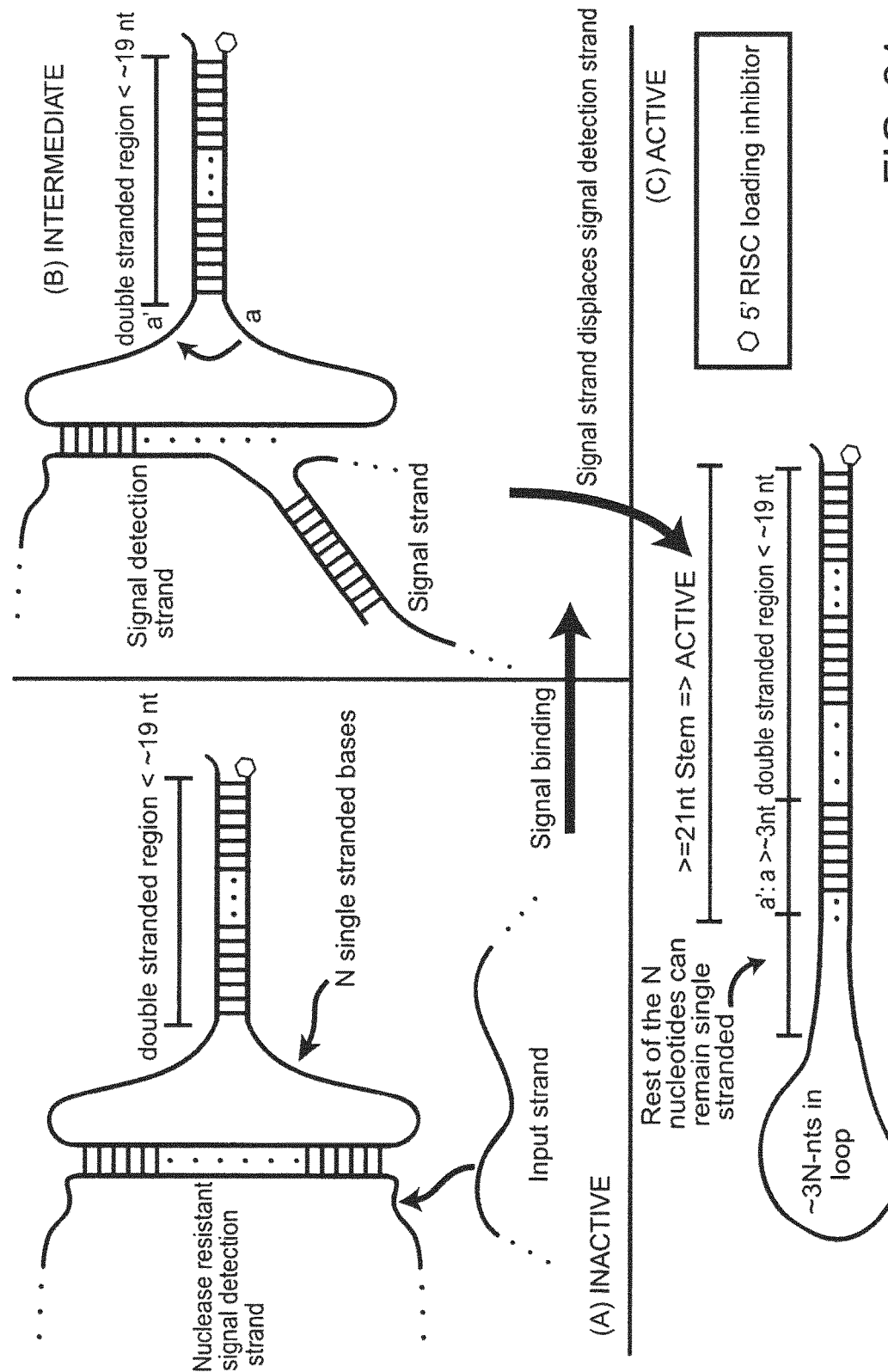

FIG. 24, panels A-C, shows an exemplary embodiment of the "Reverse Rip Loop Scheme" that allows total sequence independence. FIG. 24, panel A, shows the inactive conformation. The hexagon represents a 5' RISC loading inhibitor. A nuclease-resistant signal-detection strand is bound to the saRNAi construct. There is a double-stranded region (~19 nucleotides) and N single-stranded bases on each side of the double-stranded region, with a pattern of nuclease-resistant modifications. The input strand is labeled. FIG. 24, panel B, shows the intermediate conformation. After the input strand binds to the signal-detection strand, the complementary regions marked a and a' bind. The regions a and a' are >~3 nucleotides. Eventually, the signal strand displaces the signal-detection strand. FIG. 24, panel C, shows the active conformation. Here, a duplex stem of >21 nucleotides has formed. This stem comprises the <~19 nucleotide region indicated in FIG. 24, panels A-B, and further comprises the duplex formed by binding of a and a'. The remainder of the N nucleotides may remain single stranded. A loop structure that comprises ~3N-nucleotides is formed.

Figure 25:
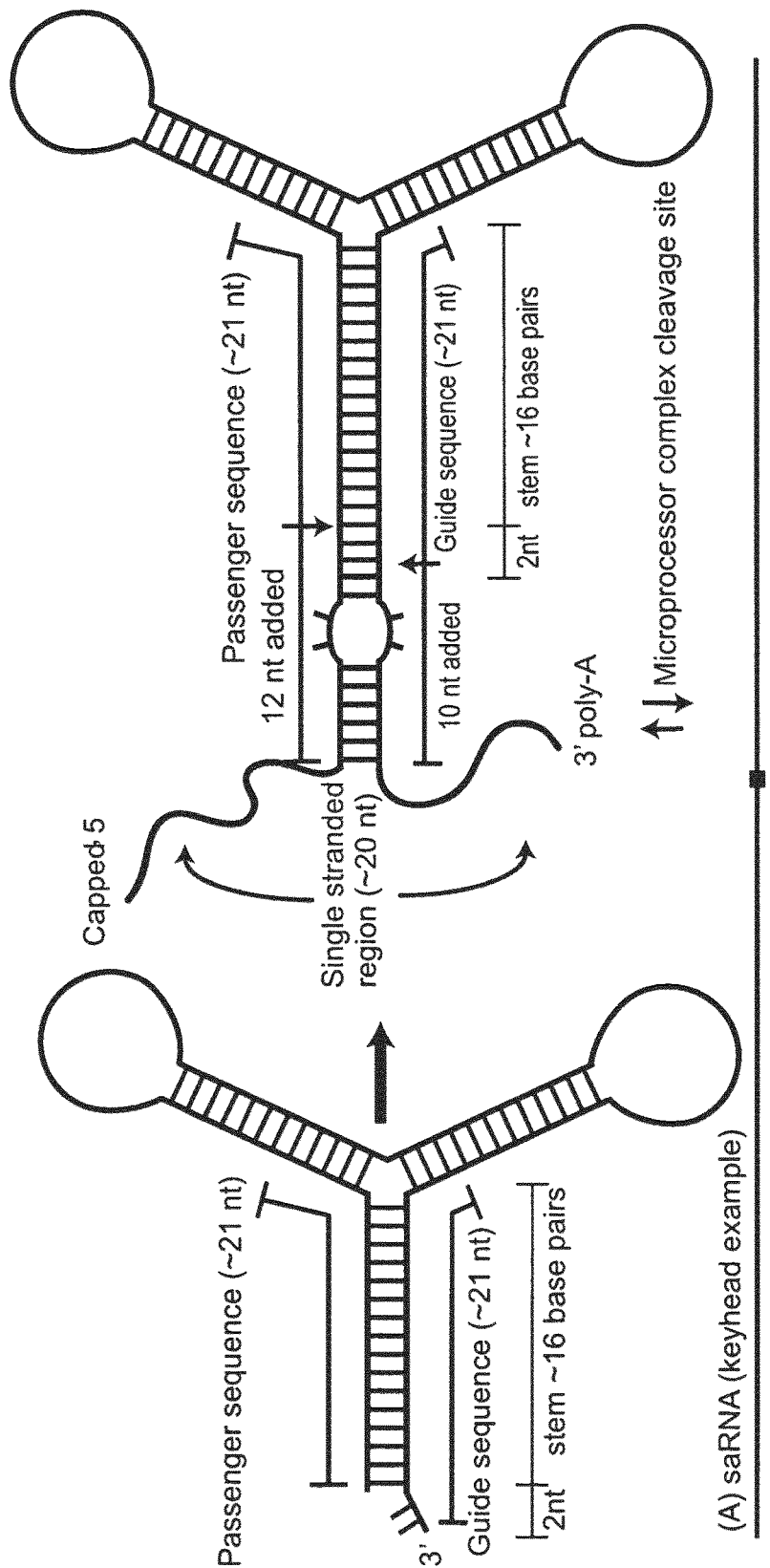

FIG. 25 shows an exemplary scheme to add a microprocessor domain to any saRNA. Shown in the left part of the figure is the saRNA keyhead design. Labels indicate the passenger sequence (~21 nucleotides) and the guide sequence (~21 nucleotides). At the 3' end, there are 2 nucleotide overhangs. The stem comprises ~16 base pairs. Arrow indicates saRNA, now further comprising a microprocessor domain. This microprocessor comprises single-stranded regions (~20 nucleotides) that extend from the 5' end from the 3' end of the saRNA construct. In addition, additional nucleotides have been added to the length of the duplex that is formed between the passenger sequence and the guide sequence. The small black arrows indicate the microprocessor complex cleavage sites.

Figure 26:
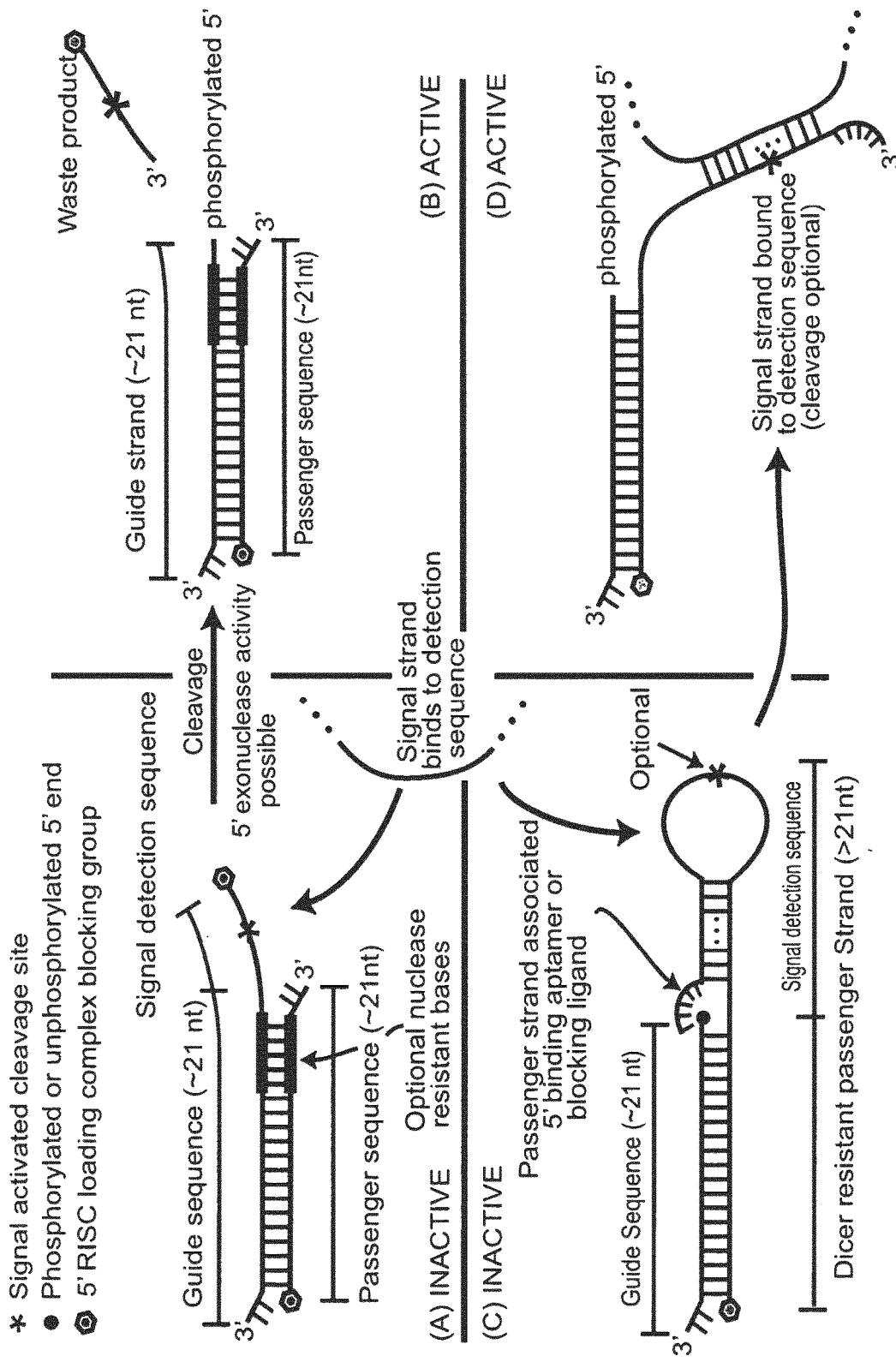

FIG. 26, panels A-D, shows some basic designs for direct RISC loading. In all of the examples illustrated here, the asterisk represents a signal-activated cleavage site, the filled circle represents a phosphorylated or unphosphorylated 5' end, and the hexagon represents a 5' RISC loading complex blocking group. FIG. 26, panel A, shows an inactive form, in which the signal strand binds to the detection sequence (indicated by arrow). FIG. 26, panel B, shows an active form. Following cleavage at the site indicated by the asterisk, where 5' exonuclease activity is possible, the active duplex form is produced. A waste product is also produced (pictured). FIG. 26, panel C, shows another inactive form. The signal strand binds to the signal-detection sequence (indicated by arrow). Here, the passenger strand is associated with a 5' binding aptamer or blocking ligand. The cleavage site (asterisk) is optional. FIG. 26, panel D, shows the corresponding active form for FIG. 26, panel C, which is a duplex stem. The signal strand is bound to the signal-detection sequence. Cleavage of this region is optional.

Figure 27:
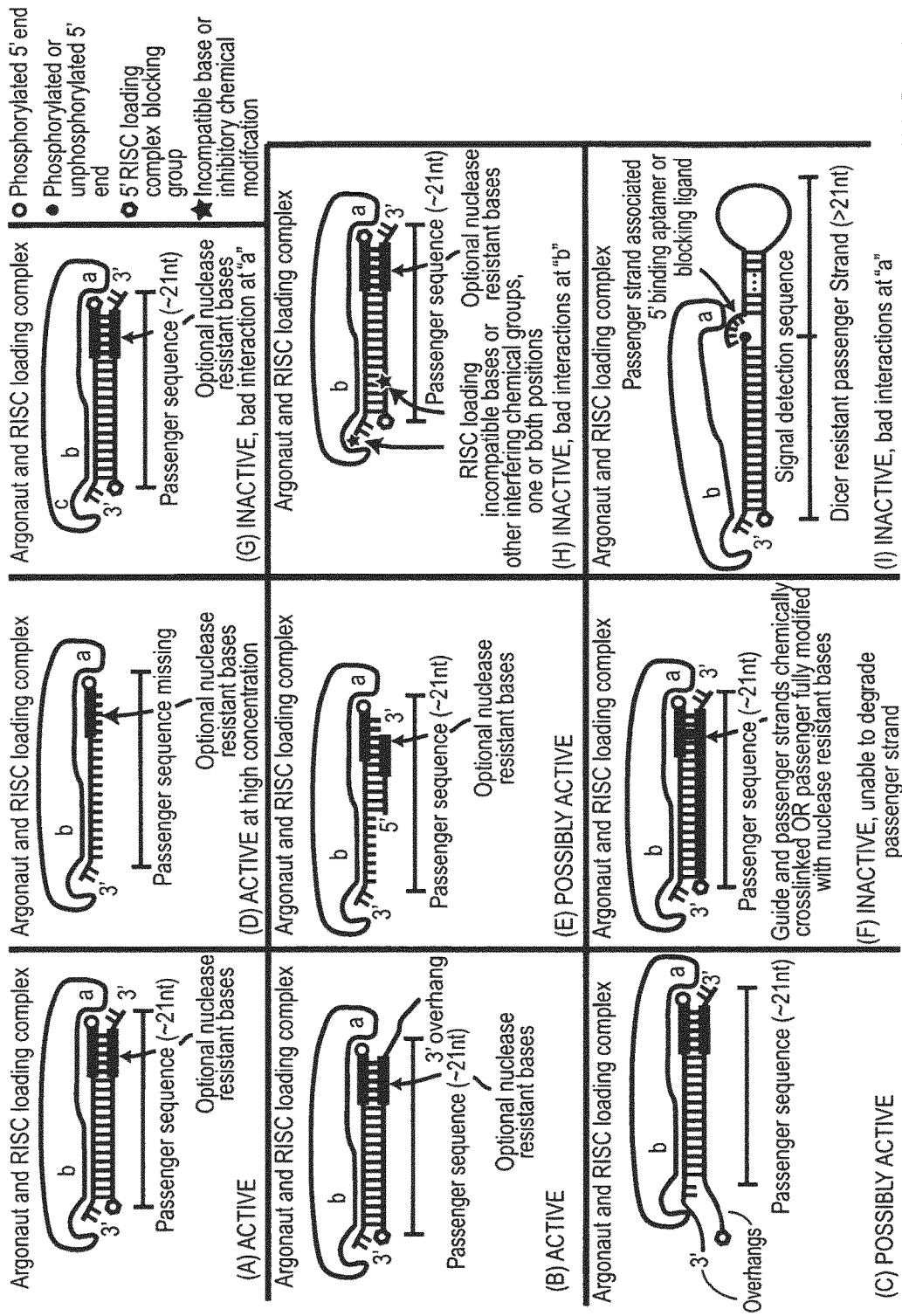

FIG. 27, panels A-I, shows some examples of active and inactive substrates for direct RISC Loading. In all of the examples illustrated here, an outlined circle represents a phosphorylated S' end, a filled circle represents a phosphorylated or unphosphorylated S' end, a hexagon represents a 5' RISC loading complex blocking group, and a star shape represents incompatible base or inhibitory chemical modifications. The following examples represent active and inactive substrates for Argonaut and the RISC loading complex. FIG. 27, panel A, shows an active form. The passenger sequence (bottom strand of duplex) is ~21 nucleotides. There are 3' overhangs on both the passenger strand and the guide strand (top strand of the duplex). Optional nuclease-resistant bases are indicated with a black arrow. FIG. 27, panel B, shows another active form. The passenger sequence is ~21 nucleotides. There is a 3' overhang on the passenger strand and a long single-stranded 3' overhang on the passenger strand. Optional nuclease-resistant bases are indicated with a black arrow. FIG. 27, panel C, shows a possibly active form. Optional nuclease-resistant bases are indicated with a black arrow. There is a 5' overhang and a 3' overhang on the passenger strand and a 3' overhang on the guide strand (upper strand of duplex). FIG. 27, panel D, shows an active form at high concentration. Here, the passenger sequence is missing. Optional nuclease-resistant bases are indicated with a black arrow. FIG. 27, panel E, shows a possibly active form. A short duplex has formed between the passenger sequence and a longer guide strand. Optional nuclease-resistant bases are indicated with a black arrow. FIG. 27, panel F, shows as inactive form, which is unable to degrade the passenger strand. Here, the guide and passenger strands are either chemically-crosslinked, or else the passenger strand is fully-modified with nuclease-resistant bases. FIG. 27, panel G, shows an inactive form, with defective interaction at "a." At point a, the interaction between the guide strand and Argonaut/the RISC loading complex is disrupted by the presence of a S' RISC loading complex blocking group on the guide strand. Optional nuclease-resistant bases are indicated with a black arrow. FIG. 27, panel H, shows an inactive form, with defective interactions at "b." At point b," the interaction between the guide strand and Argonaut/the RISC loading complex is disrupted. Either RISC-loading incompatible bases or other interfering chemical groups may be located at one or both of the positions indicated by star shapes. Optional nuclease-resistant bases are indicated with a black arrow. FIG. 27, panel I, shows an inactive form, with defective interactions at "a." The passenger strand is associated with a 5' binding aptamer or a blocking ligand. The Dicer-resistant passenger strand (>21 nucleotides) is also associated with a signal-detection sequence.

Figure 28:
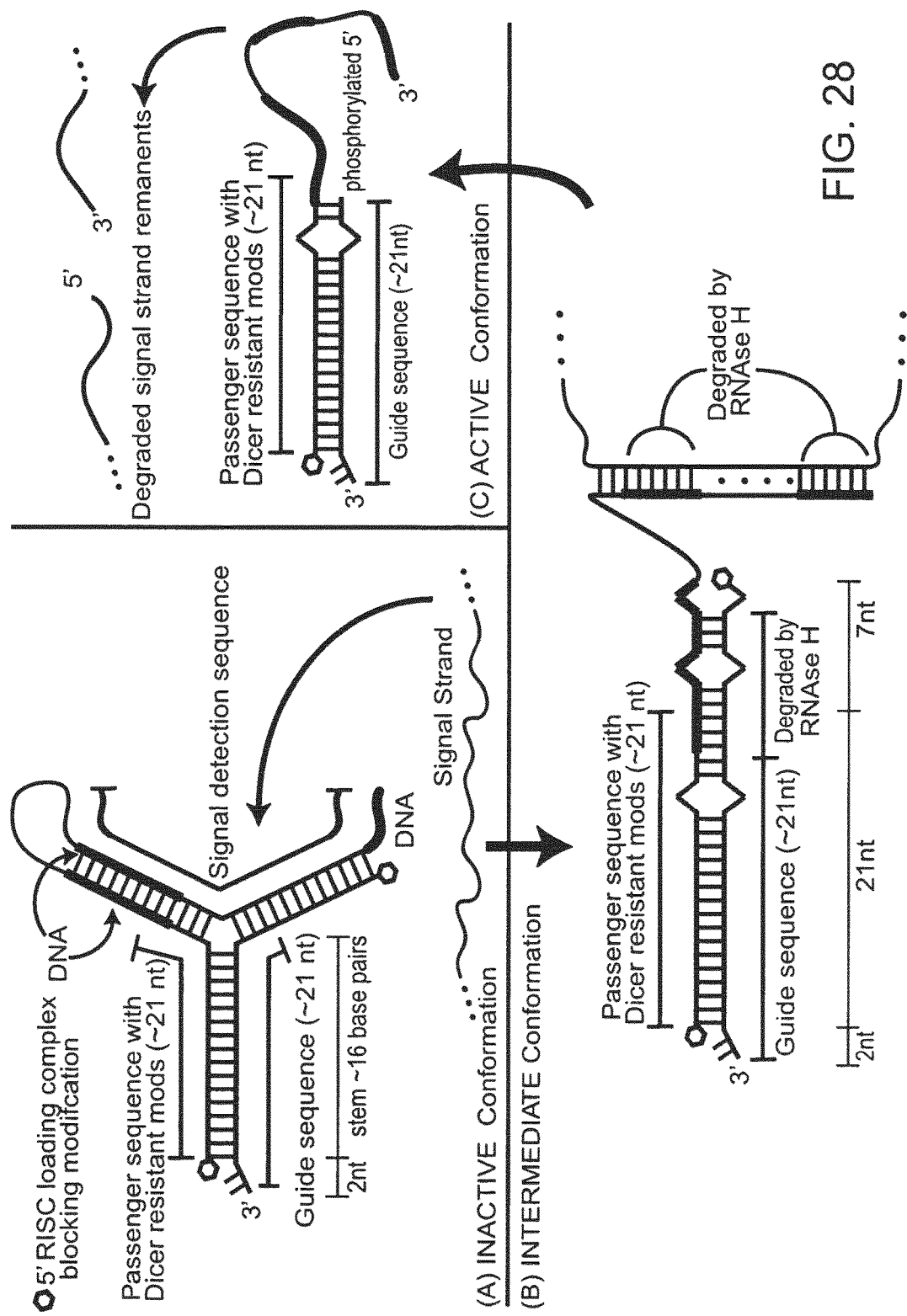

FIG. 28, panels A-C, shows an exemplary embodiment of keyhead (telescoping) design with direct RISC loading. FIG. 28, panel A, shows an inactive conformation. Hexagon shape, 5' RISC loading complex blocking modification. In the inactive conformation, the saRNAi construct comprises a guide sequence (~21 nucleotides) and a passenger sequence with Dicer resistant modifications (~21 nucleotides). Also indicated are 2 nucleotides at the 3' end, and two additional arms forming a 3-arm junction. The signal detecting sequence and regions comprising DNA are indicated. FIG. 28, panel B, shows an intermediate conformation. After binding of the signal strand, the saRNAi construct adopts an intermediate conformation. A duplex (~21 nucleotides) is formed from a guide sequence (~21 nucleotides) and a passenger sequence with Dicer resistant modifications (~21 nucleotides). This region is adjacent to a RNA:DNA hybrid (here, 7 nucleotides in length), which may be degraded by RNase H. In a duplex formed by the signal strand and the signal-detecting strand, any DNA:RNA hybrid regions may also be degraded by RNase H. FIG. 28, panel C, shows the active conformation. The active conformation comprises a duplex formed from the guide sequence (~21 nucleotides) and a passenger sequence with Dicer resistant modifications (~21 nucleotides). The 5' end of the guide sequence is phosphorylated. The sequence at the 3' end of the passenger sequence is indicated, as are the degraded signal strand remnants.

Figure 29:
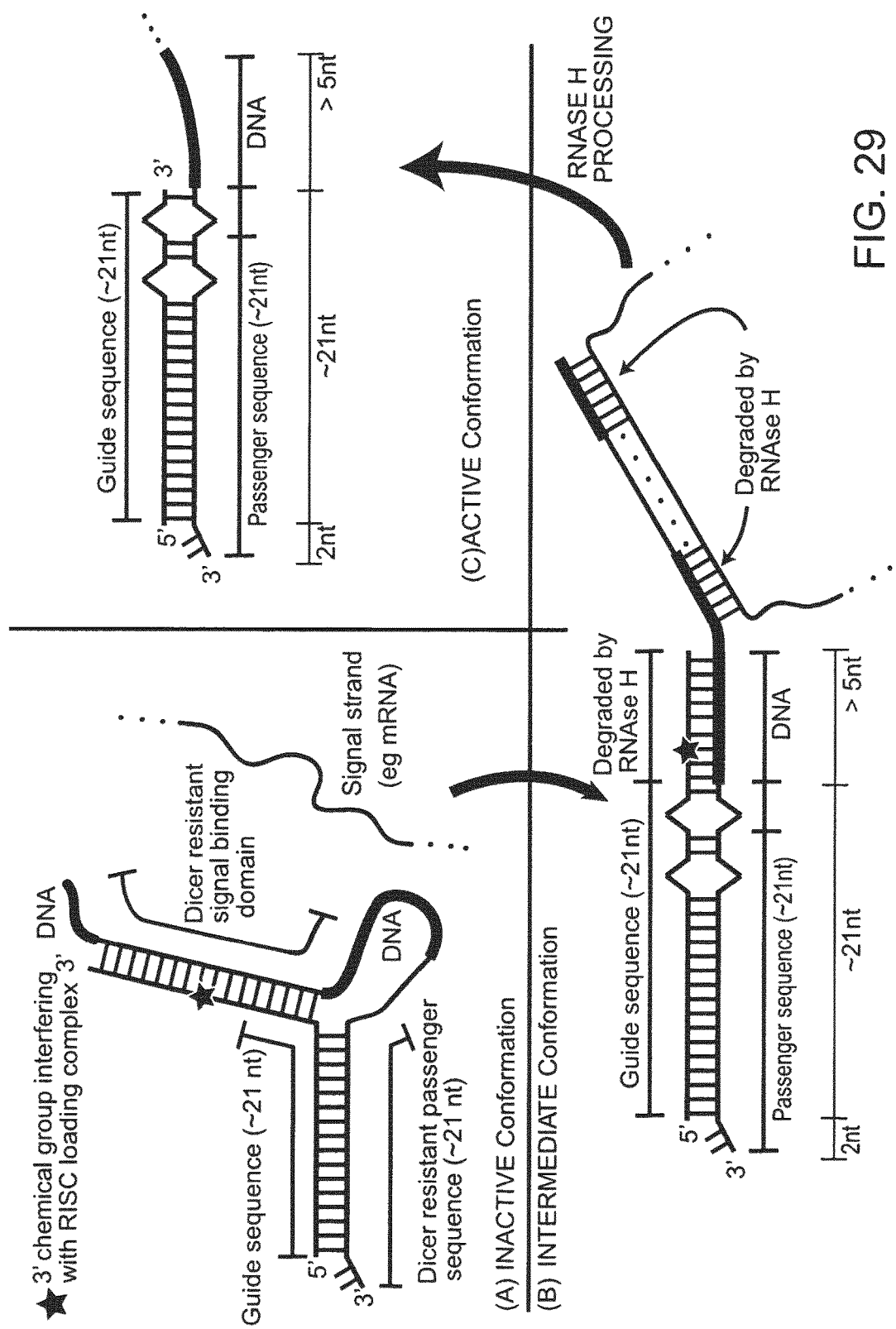

FIG. 29, panels A-C, shows an exemplary chimera-masking design with direct RISC loading. FIG. 29, panel A, shows the inactive conformation. The star shape represents a 3' chemical group interfering with RISC loading complex. Labels indicated the guide sequence (~21 nucleotides) and the Dicer-resistant passenger sequence (~21 nucleotides). One region comprises a Dicer-resistant signal-binding domain. There are also DNA bases in 2 regions. Also indicated is the signal strand. In some embodiments, the signal strand may be mRNA. FIG. 29, panel B, shows the intermediate conformation. Here, the guide sequence is ~21 nucleotides, and the passenger sequence is ~21 nucleotides. The duplex region comprises ~21 nucleotides, plus 2 nucleotides at the 3' end, and is adjacent to a RNA:DNA duplex of >5 nucleotides. This DNA:RNA is degraded by RNase H, as are regions where the signal strand has bound to DNA sequences. FIG. 29, panel C, shows the active conformation. Following RNase H processing, the saRNAi construct adopts the active conformation. Labels indicate the guide sequence (~21 nucleotides) and the passenger sequence (~21 nucleotides), which together form a duplex of ~21 nucleotides. There is also a 3' overhang of 2 nucleotides, and a DNA region that comprises >5 nucleotides.

Figure 30:
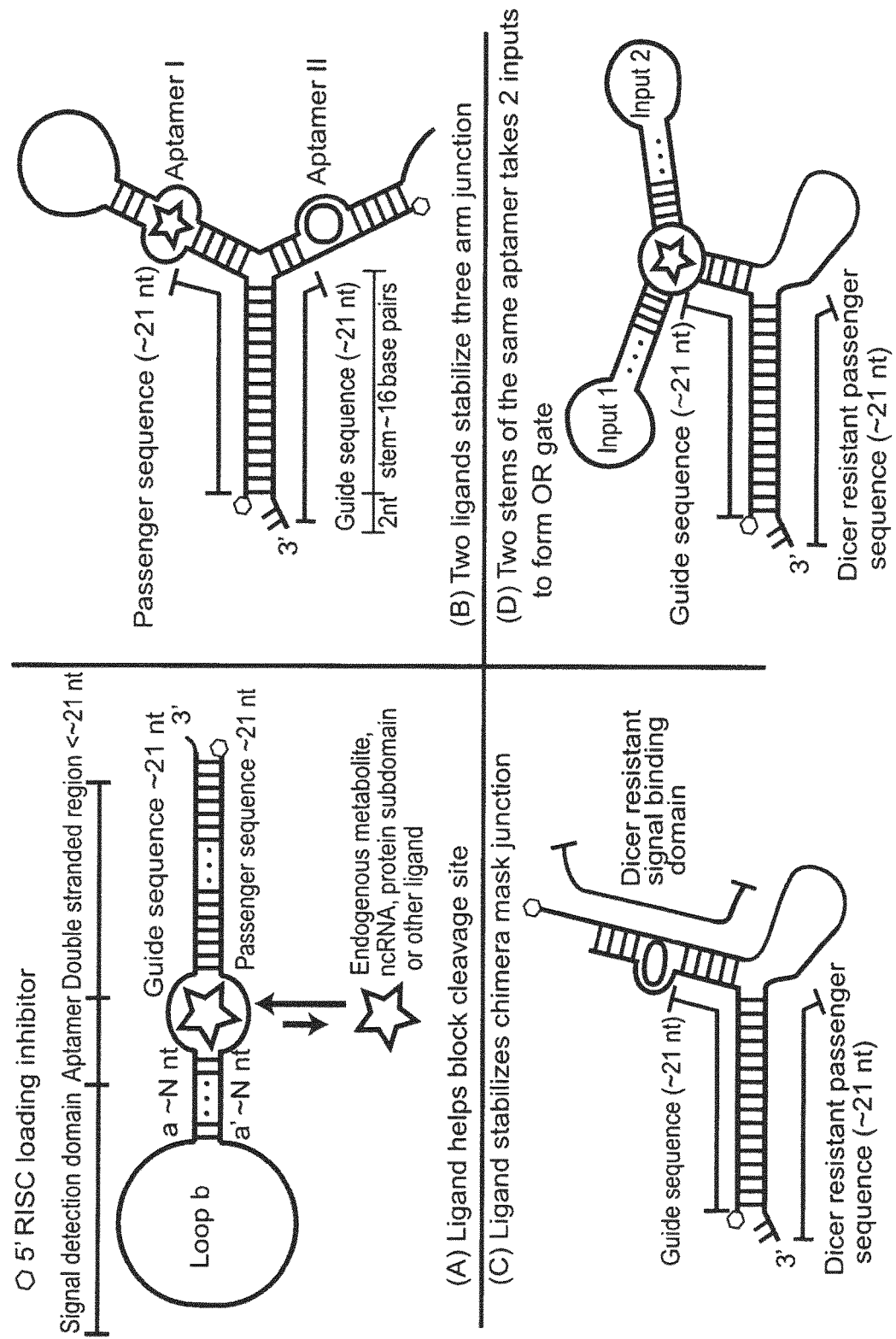

FIG. 30, panels A-D, shows an exemplary embodiment of the endogenous ligand-stabilized saRNA, which ligand stabilizes a number of inactive conformations. FIG. 30, panel A, shows that the ligand helps block cleavage site. Hexagon, 5' RISC loading inhibitor. Labels indicate the signal detection domain, comprising loop b; aptamer; and double stranded region <~21 nucleotides, comprising the guide sequence ~21 nucleotides and passenger sequence ~21 nucleotides. Loop b and regions a and a' are marked. Star shape, endogenous metabolite, ncRNA, protein subdomain or other ligand. FIG. 30, panel B, shows that two ligands stabilize three arm junction. The passenger strand (~21 nucleotides) and the guide sequence (~21 nucleotides) are labeled. The duplex stem is ~16 base pairs, and there is a 2 nucleotide overhang at the 3' end. Two ligands, indicated by the star shape (Aptamer II) and the circle shape (Aptamer II), are bound. FIG. 30, panel C, shows that a ligand stabilizes a chimera mask junction. Labels indicate the guide sequence (~21 nucleotides) and the Dicer resistant passenger sequence (~21 nucleotides). In addition, there is a Dicer-resistant signal-binding domain. FIG. 30, panel D, shows that two stems of the same aptamer takes 2 inputs to form OR gate. Input 1 and Input 2 are labeled. The star shape represents the endogenous metabolite, ncRNA, protein subdomain or other ligand. As indicated, the guide sequence is ~21 nucleotides, while the Dicer resistant passenger sequence is ~21 nucleotides.

Figure 31:
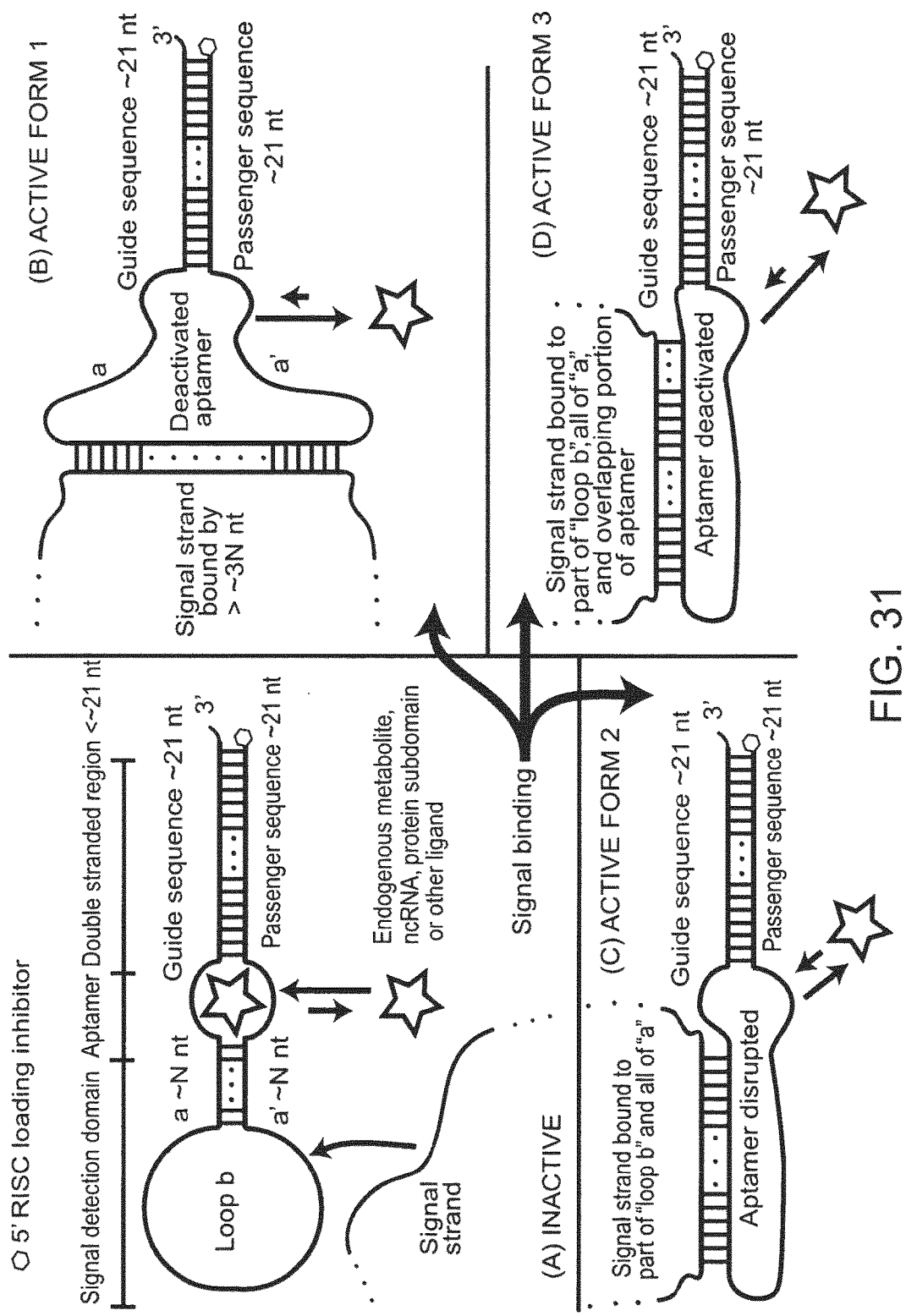

FIG. 31, panels A-D, shows an exemplary embodiment where an endogenous ligand-stabilized saRNA is deactivated (i.e., the saRNA is activated). FIG. 31, panel A, shows the inactive form stabilized by the ligand. Hexagon, 5' RISC loading inhibitor. Labels indicate the signal detection domain, comprising loop b; aptamer; and double stranded region <~21 nucleotides, comprising the guide sequence ~21 nucleotides and passenger sequence ~21 nucleotides. Loop b and regions a and a' are marked. Star shape, endogenous metabolite, ncRNA, protein subdomain or other ligand. The signal strand binds to loop region b. FIG. 31, panel B, shows active form 1. Here, the signal strand is bound by >~3N nucleotides. The deactivated aptamer is labeled. The guide sequence is guide sequence ~21 nucleotides, while the passenger sequence ~21 nucleotides. FIG. 31, panel C, shows active form 2. Here, the signal strand is bound to part of "loop b" and all of "a." The aptamer is disrupted. The guide sequence is guide sequence ~21 nucleotides, while the passenger sequence ~21 nucleotides. FIG. 31, panel D, shows active form 3. Here, the signal strand is bound to part of "loop b", all of "a", and an overlapping portion of the aptamer. The aptamer is deactivated.

The entire contents, including all figures, of U.S. provisional applications 61/007,004, filed on Dec. 10, 2007, and 61/063,604, filed on Feb. 5, 2008, are incorporated herein by reference.

DETAILED DESCRIPTION OF THE INVENTION

I. Overview

The present invention provides various constructs that modulate target gene expression through the RNA interference (RNAi) pathway, which constructs may be described as signal-activated polynucleotide constructs (SAPs or SAPCs). Such signal activated polynucleotide constructs are advantageous over the traditional RNAi constructs in several respects.

For example, the subject signal activated polynucleotide constructs are only activated in cells with known disease signatures, therefore, any associated side effects are minimal. Secondly, the subject signal activated polynucleotide constructs uses disease-associated RNA as signals to activate RNA interference against target not limited to the disease-associated RNA itself. This opens a new avenue for disease prevention or intervention by disrupting the function of critical cellular pathways, induce apoptosis or inflammatory responses, or other effective anti-disease responses, only in the disease cells. Furthermore, the subject signal activated polynucleotide constructs reduce the potential for non-specific gene knock down in healthy cells by employing multiple layers of discrimination between diseased and healthy cells. For instance, the subject constructs allow the use of other independent probe systems to examine SNPs and other disease related RNA sequences in more discerning manners, and activate RNAi by releasing signaling factors. In addition, the subject constructs allow the integration of multiple signals to reduce error rates. Multiple constructs could interact in a chemical feedback network to determine the presence of disease. Last but not least, the subject signal activated polynucleotide constructs may be chemically modified to minimize cellular immunity (e.g., PKR-response).

Thus in one aspect, the signal-activated polynucleotide constructs of the invention may be present in either an active state or an inactive state. In the active state, the signal-activated polynucleotide constructs can be processed to mediate destruction of one or more targets (such as mRNA targets or other targets), or to regulate translation of certain mRNA transcripts (for example, via a microRNA or miRNA type mechanism). In the inactive state, the signal-activated polynucleotide constructs cannot be processed to regulate activity of the targets.

Accordingly, one aspect of the invention provides a signal-activated polynucleotide construct, comprising: (1) a guide sequence and a sense sequence capable of forming a duplex region that can either become an siRNA or miRNA or be cleaved by Dicer to generate an siRNA or an miRNA comprising the guide sequence, wherein the guide sequence is substantially complementary to a transcript of a target gene; and, (2) a signal detecting sequence capable of binding I hybridizing with either: (a) one or more signals (e.g., signal polynucleotides), or, (b) one or more regions comprising part of the guide sequence and/or part of the sense sequence; wherein, (i) in the absence of the signal polynucleotides, the signal detecting sequence hybridizes with the one or more regions comprising part of the guide sequence and/or part of the sense sequence, wherein generation of the siRNA or miRNA (e.g., by Dicer cleavage) is inhibited, and/or productive incorporation of the siRNA or miRNA into RISC is inhibited; (ii) in the presence of the signal polynucleotides, the signal detecting sequence hybridizes with the signal polynucleotides, and allows, enables, or promotes the formation of the duplex region for the generation (e.g., for cleavage by Dicer) of the siRNA or the miRNA. Preferably, the siRNA or miRNA can be productively incorporated into RISC to effect gene silencing of the target gene.

As used herein, "siRNA/miRNA" includes any small interfering RNA I microRNA that can be loaded into RISC complex and inhibit target gene expression through the RNA interference mechanism (e.g., either cleave the target sequence, or inhibit target mRNA translation). The siRNA I miRNA does not have to be between 19-21 nucleotides in length. Preferably, the siRNA does not require Dicer cleavage to be loaded into RISC.

In certain embodiments, the signal is a signal polynucleotide (DNA, RNA, DNA-RNA hybrids, with or without chemical modifications, and with or without nucleotide analogs or non-canonical nucleotides), which is capable of hybridizing with the signal detection sequence under high stringency hybridization conditions or physiological conditions of a cell.

A nucleic acid molecule is "hybridizable" to another nucleic acid molecule, such as a cDNA, genomic DNA, or RNA, when a single stranded form of the nucleic acid molecule can anneal to the other micleic acid molecule under the appropriate conditions of temperature and solution ionic strength (see Sambrook et al. Molecular Cloning: A Laboratory Manual, Second Edition (1989) Cold Spring Harbor Laboratory Press, Cold Spring Harbor, N.Y.). The conditions of temperature and ionic strength determine the "stringency" of the hybridization. Low stringency hybridization conditions correspond to a $T_m$ (melting temperature) of 55° C., e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringency conditions" are understood to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. Current Protocols in Molecular Biology, John Wiley & Sons, N.Y. (1989), 6.3.1-6 or 13.3.6; or pages 9.47-9.57 of Sambrook, et al. (1989) Molecular Cloning, 2nd ed., Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$, for hybrids of nucleic acids having those sequences. The relative stability (corresponding to higher $T_m$) of micleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

In other embodiments, the signal may be a small molecule (e.g., one that is no more than 2000 Da, 1500 Da, 1000 Da, 500 Da, 200 Da, 100 Da, 50 Da etc.), such as a metablite or intermediates thereof, polypeptide, protein, lipids, vitamin, etc., which may bind to, for example, aptamers on the signal detecting sequence. The small molecule signal may be either endogenous or exogenous to a cell.

In general, any transcript of a target gene can be a target of the subject constructs. In certain embodiments, the target may be an mRNA or a target gene. In certain embodiments, the target may be a non-coding RNA of interest. In certain embodiments, the target may be another (identical and/or different) signal activated polynucleotide construct. If the target is an identical signal activated polynucleotide construct, the construct is capable of self-modulating through a feedback control mechanism. In addition, one or more target transcripts sharing a common target sequence maybe targeted simultaneously by the same signal activated polynucleotide construct. Conversely, one or more signal activated polynucleotide constructs may be activated by different signals but target the same target sequence.

The target gene can be any gene of interest, including genes coding for proteins or non-protein products. The target gene may be either disease-associated genes or normal genes (such as essential genes required for cell viability). Merely to illustrate, exemplary disease-associated genes include BCL-1 (apoptosis), HSF-1 (heat shock factor, important to pancreatic cancer and others), NOX-4 (pancreatic cancer), etc. In certain preferred embodiments, the target gene is an intended/desired/pre-determined (as opposed to a spurious) target gene.

As used herein, "productive incorporation (of the siRNA or miRNA) into RISC" includes the proper loading of the siRNA or miRNA into the RISC complex, such that the resulting complex is at least partially or substantially functional in terms of inhibiting gene expression through the RNAi mechanism. Certain polynucleotides may be improperly loaded into RISC, but the resulting complex is substantially not functional. Such RISC loading is not productive within the meaning of the invention. According to the instant invention, certain parts or regions of the subject constructs can be potentially loaded into RISC spuriously, or loaded into RISC in the absence of signal. Thus the invention provides design principles concerning such features as the size, the junction structure, and/or any chemical modifications that may make such parts or regions poor substrates for direct incorporation into RISC.

In certain embodiments, in the absence of the signal polynucleotides, generation of the siRNA or miRNA, generation of the off-target siRNA or miRNA (e.g., those using the sense sequence as the guide strand in a RISC complex), and/or productive incorporation of the siRNA or miRNA into RISC is inhibited by at least about 2-fold (i.e., to 50%), 5-fold (i.e., to 20%), 10-fold (i.e., to 10%), or 20-fold (i.e., to 5%) or more. Preferably, the conformation of the signal activated polynucleotide construct in the absence of a signal polynucleotide has a lower free energy at 37° C. in physiological conditions than does the conformation in the presence of the signal polynucleotides. The difference in free energy is preferably at least about 5 kcal/mole, or at least about 10 kcal/mole. Such free energy difference may be partly based on the base-pair pattern differences between the two conformations, the use of wobble base-pairing, the use of chemically modified nucleotides, and/or the substitution of A-T base-pairs with G-C base-pairs (or vice versa), etc. Any art-recognized free-energy calculation software may be used to calculate the free energies (and differences thereof) between different conformations of the subject constructs.

In certain embodiments, the signal-activated polynucleotide constructs may comprise two or more single-stranded polynucleotides. Collectively, the several single-stranded polynucleotides may fold into substantially the same structures that a continuous and uninterrupted single-stranded construct would adopt. Preferably, the multi-stranded construct may have substantially the same free energy as the single-stranded counterpart. Any resultant interruptions, gaps, nicks, or regions between the two or more single-stranded polynucleotides may occur at any location in the polynucleotide molecule. In some embodiments, the single-stranded sequence is found in the loop region of the signal-activated polynucleotide, while in other embodiments, the single-stranded sequence is found in the stem region. In other embodiments, assembly of single-stranded polynucleotides allows chimeric nucleotides (e.g., some single-stranded polynucleotide may be DNA, while others are RNA or polynucleotides with chemical modifications) to be formed. Such chimeric constructs may be advantageous since certain chemically modified nucleotides can be incorporated in the multi-stranded construct, while the rest of the construct can be easily synthesized by transcription or chemical synthesis. In certain preferred embodiments, free energy of such multi-stranded constructs may be adjusted (supra) such that the assembly/complex formed from the single-stranded polynucleotides does not dissociate at a rate faster than the period of time that the construct will remain in the cell.

In certain embodiments, single-stranded regions in the multi-stranded constructs (or any of the subject constructs in general) may optionally be protected against nuclease degradation by, for example, using chemical modifications, including inverted dT, DNA/LNA nucleotides (against exonucleases, e.g., XRN1), and 2'-O-Me, 2'-F, and phosphothioate modifications for single-stranded regions (against endonucleases).

In certain embodiments, a safe pathway of degradation is provided, such that degradation of one or more strands from the assembly of single-stranded polynucleotides does not inadvertently activate RNAi or RNAa mechanisms, or create undesirable side products. Thus the region of the signal-activated polynucleotide that contains the RNAi guide strand may be less protected from degradation to ensure that it will be degraded first.

In certain embodiments, nucleotides with chemical modifications may be largely or mostly present on one or more of the single-stranded nucleotides. For example, in certain embodiments, most nucleotides on the signal detection sequence may be modified.

In certain embodiments, the signal-activated polynucleotide is not activated in the absence of the signal polynucleotides when one or more of the single-stranded polynucleotides are removed from the construct.

In certain embodiments, two or more of the single-stranded polynucleotides may be covalently linked by a linker moiety (such as PEG) or a bond other than canonical polynucleotide linkage. This allows the single-stranded polynucleotide components to be linked together after the multi-stranded construct is assembled. Linkage may be achieved via enzymatic ligation of the individual strands, use of chemical linker moieties, such as PEG, or formation of bonds other than canonical polynucleotide linkages.

In certain embodiments, only one 5'-end and one 3'-end within the signal-activated polynucleotide construct is compatible for Dicer cleavage and RISC incorporation. For example, in a multi-stranded construct, other ends may be chemically modified to become incompatible for Dicer cleavage and/or RISC loading. Suitable chemical modification may include, for example, inverted dT or a stretch of a few DNA bases, etc. Other blocking groups for Dicer cleavage/RISC loading are described in other sections or are known in the art.

In a related aspect, a signal polynucleotide may come together with an active Dicer substrate to create an inactivated construct, such as one described herein. Such a signal polynucleotide may be an mRNA, a miRNA, a DNA or may be any other signal, as described herein. Thus, according to this aspect of the invention, the target gene is not targeted by the Dicer substrate in the presence of the signal. In other words, a signal may be used either to activate components of the RNAi pathway, or to inactivate the RNAi pathway.

In certain embodiments, the guide sequence and the sense sequence form a short duplex region of no more than 19 base pairs in length in the absence of the signal polynucleotides. For example, the duplex region formed by the guide sequence and the sense sequence may be about 11, 16, or 18 base pairs in length. In certain embodiments, the short duplex region is more than 11 base pairs in length. In some embodiments, the short duplex region comprises one or more chemical modifications that confer resistance to nuclease degradation. Suitable chemical modifications for conferring nuclease resistance include: LNA, DNA (if DNA:RNA hybrid portions exist, the hybrid is preferably shorter than 5 bp to prevent RNase H degradation), DNA:DNA duplexes (e.g., those located in the first 8 bases from the 5' of the guide strand), 2'-O-methyl, 2'-deoxy-2'-Fluoro, Phosphorothioate, Morpholino, diaminopurines, 2'-O-MOE, 4' thio, boranophosphate, 2,4-difluorotoluyl, etc. Other modifications are provided herein below.

In certain embodiments, in the absence of the signal polynucleotides, the guide sequence and the sense sequence form a double-stranded region comprising one or more chemical modifications that inhibits Dicer cleavage (e.g., modification at or around the Dicer cleavage site) and/or productive RISC incorporation. The double-stranded region may or may not be less than 19 base pairs. The sense sequence, or any other undesired sequence in the construct that can potentially be loaded into RISC to cause off-target effect, may be modified to prevent effective Dicer cleavage and/or RISC loading. In some embodiments, suitable chemical modifications may comprise DNA bases, 2'-O-Me, LNA, fluorescein end-labels, and PEG segments, incorporated in or around the Dicer cleavage site. Internal fluorescein/2'-O, 4'-O-ethylene thymidine (eT)/2-hydroxyethylphosphate modified thymidine (hp)/etc. may be present on the sensing region forming the Y-junction or chimeric mask to reversibly block RISC incorporation.

For example, in one embodiment (sometimes referred to as the "reverse chimera embodiment"), the signal-activated polynucleotide may adopt an inactive conformation because of the presence of several DNA bases in the duplex region formed by the guide sequence and the sense sequence. Specifically, the duplex region may be more than 19 base pairs in length (e.g., 21 bps), and can potentially become a Dicer substrate. However, substituting a few RNA nucleotides around the predicted Dicer cleavage site with DNA base will block Dicer processing (see FIG. 16, panels A-C, sequence B*, a 3-bp DNA, within the 21-bp duplex region). In the presence of the signal polynucleotide, an adjacent RNA sequence B displaces DNA sequence B* (partly due to the higher stability of RNA:RNA duplex over RNA/DNA hybrid) and creates a Dicer substrate. In this active conformation, the signal-activated polynucleotide can be cleaved by Dicer and/or loaded into RISC.

In certain embodiments, part of the guide sequence and part of the sense sequence, when forming part of the duplex region, comprises one or more mismatched base pairs. For example, both sides of the mismatch loop can be 3 nucleotides. Alternatively, an asymmetric bulge can be created such that, for example, 3 bases are on one side and 2 bases or less are on the opposite side. For miRNAs, 4 or more base mismatches may be tolerated.

In some embodiments, a continuous stretch of 3 or fewer nucleotides in the guide sequence are complementary to the signal-detecting sequence. In some embodiments, a continuous stretch of 5 or fewer nucleotides in the sense sequence are complementary to the signal-detecting sequence. Requiring fewer nucleotide overlaps between the guide/sense sequences and the signal detecting sequence ensures maximum sequence selection independence concerning the signal polynucleotides and the target for the siRNA/miRNA.

In certain embodiments, the guide/sense sequences and the signal-detecting sequence could pair asymmetrically, such that one or more nucleotides are unpaired and forms an asymmetrical bulge.

In certain embodiments, the guide sequence may comprise a 2-nucleotide 3' overhang.

In certain embodiments, a continuous stretch of 5 or more nucleotides in the guide/sense sequences are complementary to the signal-detecting sequence. This design shortens the duplex region that forms between the guide strand and the sense strand in the absence of a signal. The larger sequence overlap pushes the junction between the blocking strand and the Dicer substrate further towards the end of the duplex, thus more effectively inhibits Dicer cleavage and/or productive RISC loading. Use of a larger sequence overlap to block Dicer cleavage is particularly easy to achieve in combination with chemically-modified bases, or when incorporated into a so-called Chimera Masking Platform.

For example, FIGS. 17A-B show a subject construct having two single-stranded polynucleotides. The heavily modified (e.g., 2'-O-Me modification on every nucleotide except for the 2 nucleotides on the 5' end, which are LNA) signal detection sequence is 5' to the unmodified guide sequence. The 3'-end 16 nucleotides of the guide sequence consist of 14 nucleotides in a duplex region, and a 2-nucleotide 3' overhang. In contrast, the part of the sense sequence that is complementary to the guide sequence and forms the 14-bp duplex region is modified by 2'-O-Me at alternative nucleotide positions, while the part of the sense sequence that hybridize with the signal detecting sequence (or the 2'-O-Me modified chimeric making sequence) are unmodified. In this construct, the 14-bp duplex comprising the guide sequence is Dicer resistant because of its short length (and possibly the sense strand modification). The 22-hp duplex region formed between the signal detecting sequence and part of the sense sequence is also Dicer resistant because of the chemical modification on the signal detecting sequence.

Upon hybridization between the signal and the signal detecting sequence, a 25-bp duplex region with an asymmetric bulge around the middle of the double-stranded region becomes a Dicer substrate. The 34-bp duplex region formed between the signal and the signal detecting sequence is not expected to trigger non-specific PKR-response, partly due to the heavy 2'-O-Me modification on one strand.

In another example, FIGS. 21A-B show a single-stranded signal-activated polynucleotide construct with base modifications. In this illustrative embodiment, the sense sequence can optionally be modified at the 5'-end to, for example, prevent spurious loading of this sense strand as a guide sequence, and/or provide enhanced stability of the entire construct. The sense sequence can also be modified by 2'-O-Me groups at alternative nucleotides on the partial duplex region formed between the sense and guide sequences (shown here as being modified on even numbered nucleotides). The 3'-end of the sense sequence (i.e., nucleotides 13-21) may form a mini hairpin structure, and may have different modification patterns. For example, the stem region of this mini hairpin may be modified, either by 2'-O-Me or deoxyribonucleotides (DNA). Similar DNA modifications may also occur elsewhere to replace 2'-O-Me modification. The loop of the mini hairpin is preferably 4 bp, but other loop length is also possible. The 3'-end of the sense sequence can alternatively exist as an unstructured single-stranded stretch of sequence.

The signal detection sequence is 3' to the sense sequence, comprising a sequence (nucleotides 26-59) that can hybridize with a signal polynucleotide. As shown herein, the 5'-end and the 3'-end of the sequence that can hybridize with (and detect) a 3'-UTR sequence in the human Lin28B mRNA is shown, and some or all of the nucleotides of that sequence can be modified by, for example, 2'-O-Me. A portion of this sequence may hybridize with the 5'-end of the guide sequence (nucleotides 80-86 in this case), another portion may hybridize with a sequence just 5' to the guide sequence. Such hybridization forms a long double-stranded region that is chemically modified (e.g., the 2'-O-Me modification in the Lin-28B-hybridizing sequence), and is thus a poor Dicer substrate.

Yet another portion of the Lin28B-hybridizing sequence may be within a single-stranded loop region. One or more "spacer region" nucleotides (optionally also chemically modified for nuclease resistance, for example) may also be present in the construct. Such single-stranded region in the Lin28B-hybridizing sequence may serve as a toehold for the incoming signal polynucleotide, and initiates the hybridization between the Lin28B mRNA and the Lin28B-hybridizing sequence on the signal detection sequence. In addition, the presence of the single-stranded spacer region may relieve any strain or tension in the activated construct.

The sequence that forms the double-stranded region with the Lin28B-hybridizing sequence may be free of or largely free of chemical modifications, and the entire guide sequence, which is at the 3'-end of the entire signal-activated polynucleotide constructs, may be free of any chemical modifications. There may be a 2-nucleotide overhang at the 3'-end of the construct. The guide sequence may target any target sequence, such as human NADPH oxidase 4.

The structure and folding of the construct (for design verification, for example) may be generated using any art recognized software, such as Mfold (see mfold.bioinfo.rpi dot edu/cgi-bin/ma-form1.cgi).

In certain embodiments, the guide sequence may comprise a 2-nucleotide 3' overhang. In other embodiments, presence of a signal polynucleotide leads to the formation of an extension duplex region, comprising base pairs between the guide sequence and the sense sequence. In some embodiments, each strand in the extension duplex region comprises about 1, 2, 3, 4, 5, 6, 7, 8, 9, or more nucleotides. The strands may be complementary to one another, or may comprise one or more mismatched base pairs.

In some embodiments, a portion of the signal-detecting sequence may hybridize with a portion of the guide sequence and/or a portion of the sense sequence, thereby forming a first and/or a second additional duplex region. When there is only one such additional duplex region, it may be formed between the signal-detecting sequence and either the guide sequence or the sense sequence.

Preferably, neither of the two additional duplex regions (either alone or in combination) triggers a PKR-response in mammalian cells. In some embodiments, avoidance of the PKR response is due in part to the size of the duplex regions. For example, the duplex regions may be 9, 10, 11, or 12 base pairs in length. Moreover, the total combined length of all duplex regions may be no more than 29 base pairs in length. This number may include a short duplex of no more than 19 nucleotides that is formed by the guide sequence and the sense sequence, plus each of the additional duplex regions described above. In other embodiments, however, the length of the additional duplex regions may each be more than 19-20 base pairs in length, and may comprise wobble base pairing or mismatches located in every 4-8 nucleotides. Wobble base pairs and mismatches may be created by substituting U for C and/or G for A. The presence of such mismatches and/or wobble base-pairing substantially reduces or eliminates PKR-response.

In other embodiments, avoidance of the PKR response is due in part to the presence of chemical modification in the duplex regions. For example, the subject signal-activated polynucleotide constructs may further comprise one or more 2'-o-methyl modifications that inhibit PKR and/or TLR activation. According to this embodiment, the combined length of the adjacent short duplex regions can be (but does not need to be) more than 29 bp in length. The presence of such 2'-O-Me modifications in DNA/RNA effectively prevents PKR-TLR response.

In certain signal-activated polynucleotides, spurious or undesirable Dicer cleavage and/or RISC incorporation may result when the construct has one or more adjacent duplex regions. For example, sequences and mismatches around the junction region of the duplex regions could cause two adjacent stems to stack together and form a Dicer-cleavable substrate. Such spurious Dicer cleavage may result in an active RISC complex directed to an unintended target. Alternatively, even though unproductive RISC loading is the ultimate result, the spurious Dicer cleavage effectively decreases the intracellular stability of the constructs.

Thus, in certain embodiments, the subject constructs comprise means or design features that control the formation of specific tertiary structures or conformations and inhibit spurious Dicer processing I RISC loading. Specifically, in certain embodiments, the subject signal-activated polynucleotide constructs may further comprise one or more single-stranded segments and/or additional duplexes around: (1) the three-way junction region, (2) the first additional duplex region (e.g., formed by the signal detecting sequence and part of the guide sequence), and/or (3) the second additional duplex region (e.g., formed by the signal detecting sequence and part of the sense sequence). These additional structures may aid formation of specific tertiary conformations that inhibit Dicer cleavage and/or RISC incorporation.

In certain embodiments, a wide range of tertiary conformations can be introduced into the subject construct by adding single-stranded regions with different sequences around the three-way RNA junctions. Such regions control the formation of the undesirable tertiary structure formation via non-canonical base-pairings or chelation of poly-valent cations. See Lescoute and Westhof, *RNA* 12: 83-93, 2006.

Alternatively, mismatch regions around the junction formed by the inactivation constructs may also be used to create similar tertiary structures, which could be significantly resistant to spurious Dicer processing and RISC loading.

In yet another embodiment, additional duplex regions may be added around the existing junctions in the subject constructs to create four-way, five-way or higher order junctions to prevent spurious Dicer-cleavage and/or productive RISC loading.

Similar strategy may also be used to prevent spurious Dicer-cleavage and/or productive RISC loading based on the duplex formed between the signal detecting sequence and the signal polynucleotide. On the one hand, having long duplex stems in the signal detection domains of the subject constructs may be important for enhanced signal sequence specificity. On the other hand, the resulting dsRNA stems potentially poses risks for cellular immune activation (e.g., PKR-response), or Dicer processing and RISC loading for unintended targets. Thus, besides using-mismatches and chemical modifications to ameliorate these undesirable side effects, the additional junction regions or single-stranded bulges to long duplexes in the signal detection domains may help to reduce such effect.

In certain embodiments, one end of the first additional duplex region may comprise a first unstructured single-stranded region. Similarly, in other embodiments, one end of the second additional duplex region may comprise a second unstructured single-stranded region. The first and second unstructured single-stranded regions may each comprises, independently, about 5, 10, 15, 20, 25, 30, 35, 40, 45, 50, 60, 70, 80, 90 or more nucleotides. Preferably, the first unstructured single-stranded region and/or the second unstructured single-stranded region may, independently of one another, comprise modified bases that inhibit endonuclease (such as RNase A, RNase H, RNase I, RNase II, RNase L, RNase P, RNase T1, RNase T2, RNase U2, RNase VI, RNase V, etc.) degradation.

Not every nucleotide in the single-stranded region needs to be modified. For example, RNase.A and its variants selectively cleave 3' of pyrimidines (C and U). Therefore, for single stranded RNA regions flanked by double stranded areas, only C and U bases need to be modified with, for example, 2'-o-methyls or 2'-deoxy-2'-fluoro bases. Alternatively, susceptible Cs and Us could be replaced by DNA, LNA, or phosphorothioate bases. In addition, purine-only single stranded regions may be used.

For single stranded regions with a single stranded 5' or 3' end, LNA can be used for the last 2-3 bases, or DNA with inverted dT base may be used at the last position. LNA with the inverted base can also be used to slow down exonuclease degradation.

In some embodiments, the signal-detection sequence may comprise one or more deoxyribonucleotides or chemically-modified ribonucleotides. In certain embodiments, the chemical modifications may be present on the ribose sugar ring, the phosphodiester backbone, and/or the base. In certain embodiments, the chemically modified ribonucleotides in the signal-detection sequence may be attached to bulky chemical groups or polymer molecules.

For example, fluorescein is a hydrophobic group that may be used (see Kim et al., *Nature Biotech.* 23: 222-226, 2008). Other chemical groups exhibiting hydrophobic character may also be used. In addition, a DNA-binding polyamide or analogous molecule may be used for RNA designed to recognize a sequence near the Dicer cleavage site (see Nickols et al., *Proc. Natl. Acad. Sci. USA* 104: 10418-10423, 2007). A polymer with high molecular weight (e.g., greater than 10 kD or 100 kD, etc.), such as PEG, may also be used.

In certain embodiments, a safe pathway for degradation of the subject signal-activated polynucleotide has been engineered into the constructs. Because the polynucleotides are double-stranded, degradation of one of the strands could result in a single-stranded product that activates the RNAi pathway, or creates an undesirable side product. To avoid creating unintended products, some embodiments leave a portion of the signal-activated polynucleotide unprotected or less protected against degradation than other portions.

For example, the portion containing the RNAi guide strand may contain no or few chemically-modified bases, whereas the chemical modifications are largely/mostly present on the sense sequence. In some embodiments, the guide sequence has no chemical modifications. Such modification pattern may be used to preferentially degrade the guide sequence to prevent potential undesirable RNAi activation.

In other embodiments, the signal-activated polynucleotide may contain one or more chemical modifications that promote hybridization between, and/or increase the stability of the binding between the signal and signal-detecting sequence. For example, the base pairings of RNA bases with 2'-O-Me, 2'-O-fluoro, LNA, PNA, or morpholino bases are more stable than RNA:RNA base pairing. Such modifications may be used for the hybridization between the signal and signal-detecting sequence.

In some embodiments, a signal-activated polynucleotide with these modifications may show improved ability to invade the secondary structure of signal mRNA molecules, and thus, in certain embodiments, the subject signal-activated polynucleotide construct comprises one or more modifications could facilitate the delivery, activity, or function of a signal-activated polynucleotide.

For example, in some embodiments, such chemical modifications may enhance non-covalent association with one or more of: cholesterol, antibodies, nanoparticles, polymers, dendrimers, liposomes, proteins, and viral envelopes. An exemplary modification include an embedded aptamer that can bind directly to receptors or proteins that facilitate transfection (Zhou et al., *Molecular Therapy* 16: 1481-1489, 2008), or that can bind nanoparticles or other delivery aids. The non-covalent association may comprise one or more of electrostatic attraction, attachment via salt bridges, hydrogen bonds, polyion-condensation and charge inversion, van der Waals interactions, and hydrophobic/hydrophilic interactions. In some embodiments, chemical modifications may comprise chemical attachments to a 5'-end, a 3'-end, or an internal nucleotide of the construct. In some embodiments, hydrogen bonds may comprise base pairing between nucleotides attached to transfection aids with single-stranded portions of the signal-activated polynucleotide.

For example, a DNA strand may be covalently or non-covalently attached to a metal nanoparticle, an antibody, or a dendrimer. A DNA or RNA strand may also have one end being an aptamer that aids transfection, or binds to a nanoparticle, antibody, dendrimer, protein, etc. To attach a subject saRNA construct to the nanoparticle, dendrimer, etc., the DNA strand attached to the nanoparticle may hybridize with a single stranded segment on the saRNA. Once the construct enters the cell, the bases could dissociate; RNaseH may cleave the DNA-bound RNA segments; or Dicer, or endogenous miRNAs may break the connection between the saRNA and the delivery aid (nanoparticle, etc.).

The selection of optimal signal sequences and target sequences may require consideration of favorable parameters and constraining conditions. In some embodiments, the signal-activated polynucleotides bind to signal polynucleotides, which may be an mRNA, an miRNA, an siRNA, a ribozyme, or a non-coding RNA. In some embodiments, the signal polynucleotide comprises two or more independent polynucleotides that are not related to one another. In these embodiments, at least one of the signal polynucleotides is not a transcript of the target gene. In some embodiments, the signal activated polynucleotide may target a wild-type gene with normal expression. In some embodiments, the mRNA of the signal polynucleotide is not a transcript of the target gene, while in other embodiments the mRNA of the signal polynucleotide is a transcript of the target gene.

The signal polynucleotides may be within a 3' UTR region, reflecting the favorable selection of the 3' UTR as a target for RNAi. In some embodiments, the lack of interference from protein translation means that sequences in the 3' UTR also serves as a suitable template for selecting signal polynucleotides.

Some secondary structures may inhibit binding of the signal polynucleotide to the signal-detecting polynucleotide. Thus in some embodiments, the signal polynucleotides are substantially free of significant secondary structure. The elimination of undesirably secondary structures can be facilitated by the use of any art-recognized secondary structure prediction software (such as MFold etc.) and/or empirical testing. In some embodiments, the subject constructs leave open a segment of the signal polynucleotide which may bind to a single-stranded region (e.g., a "toehold") in the signal-detecting polynucleotide.

In certain embodiments, both the signal and the target polynucleotides may be within evolutionarily conserved sites for miRNA binding. In some embodiments, the signal polynucleotides are calculated to lack sequence identity with other sequences in the human genome. In other embodiments, the signal polynucleotides comprise mutations associated with a disease or cellular process.

In certain embodiments, the sequence of the signal-detecting sequence is adjusted to achieve optimal levels of hybridization with the signal sequence. The optimal level of hybridization in a given experiment may not necessarily reflect the maximum possible hybridization. Mismatch or wobble base-pairings, substituting G-C with A-T base pairing or other modified base-pairing may be used to fine-tune the optimal/desired level of hybridization.

In some embodiments, optimal levels of hybridization may be achieved by adjusting the signal or target sites on mRNAs to achieve optimal (again, not necessarily the maximum) level of hybridization with the target gene transcript. It is well-known in the art that different sites in mRNA transcripts may have different efficiencies as signals or targets for RNAi knockdown.

In some embodiments, adjustment of the guide sequence in the siRNA or miRNA may be used to achieve optimal levels of hybridization. It is also possible to add mismatches to detection or target sites. In certain embodiments, the target perfectly matches the seed region (i.e., guide sequence nucleotides 2-8, counting from the 5' end of the guide sequence).

The activity of the activated saRNA construct can be further fine-tuned by, for example, introducing chemical modifications on the guide strand, around the expected Dicer cleavage site. Evidence shows that when a RISC complex bind to a target mRNA, the RISC complex cleaves the target mRNA at the position opposite the 10th and the 11th nucleotides on the guide strand (counting from the 5' end). Thus, chemical modifications at or around those positions partially or completely disrupts base pairing between the guide strand and the target mRNA, leading to impairment of enzymatic cleavage by RISC. The RISC complex then functions more like an miRNA-loaded RISC, i.e., it inhibits mRNA translation and shorten mRNA half-life, without immediately degrading the target mRNA. Thus, the functioning/activity of the activated signal-activated RNA constructs can be fine-tuned (e.g., reduced).

Chemically-modified bases may also change the binding energy between the nucleotide strands, or may inhibit RISC cleavage of target mRNA. In other embodiments, the number or signal sites or target sites on any given mRNA may be varied. The variation may be facilitated by the use of two or more different signal-activated polynucleotides.

In some embodiments, a signal-activated polynucleotide may have a signal-detecting sequence that hybridizes with one or more regions in the guide sequence and also hybridizes with one or more regions in the sense sequence, and further comprises a 3-4 nucleotide single-stranded region between the sequences that hybridize to the portion of the guide sequence and the portion of the sense sequence. In other embodiments, two or more signal polynucleotides may bind simultaneously or sequentially to the different portions of the signal-detecting sequence. The presence of at least two such signal polynucleotides may be required for generation of siRNA or miRNA products, or, in alternate embodiments, may be sufficient for generation of siRNA or miRNA products. In some embodiments, one signal polynucleotide partially displaces the signal-detecting sequence, which subsequently allows complete displacement of the signal-detecting sequence by other hybridization events. For example, hybridization between the sequence in a loop region of a signal-activated polynucleotide and the remaining portion of the signal-detection sequence leads to complete displacement of the signal-detection sequence.

In an exemplary embodiment, a signal-activated polynucleotide forms an inactive 3-arm junction conformation comprising three duplex regions arrayed in a Y configuration. One duplex region comprises a portion of the guide strand of RNA, with at most 18 or 19 nucleotides (preferably about 16 nucleotides) paired to a complementary strand. The guide strand/sequence optionally contains a 2-nucleotide 3' overhang. The second duplex region (one arm of the Y configuration) comprises about 3 nucleotides of the guide strand and further comprises a sequence of RNA that is complementary to a portion of the signal-detecting sequence, paired with the complementary sequence from the signal-detecting sequence. The third duplex region (the other arm of the Y configuration) comprises the remainder of the signal-detecting sequence, and further comprises RNA that is complementary to the signal-detecting sequence and further comprises about 5 nucleotides of the passenger strand sequence. In this conformation, the guide strand and passenger strands form a duplex that is too short to be a substrate for Dicer, and the signal-activated polynucleotide is held in an inactive conformation. Optionally, chemical modifications of the short duplex region (such as those described above) may be used to further prevent the spurious Dicer cleavage and/or productive RISC loading in the absence of the signal.

To switch to the active conformation, the signal-activated polynucleotide binds to a signal polynucleotide or input strand. This input strand (such as a mRNA sequence) binds to the entirety of the signal-detecting sequence, displacing the two duplex regions that contain the signal-detecting sequence. This frees the constraints placed on the duplex region that contains the guide and passenger strands, such that all complementary nucleotides in the guide and passenger strands form an extension duplex region, which, in combination with the existing short duplex region formed between the guide sequence and the sense sequence, forms a double-stranded duplex region that is long enough to be processed by Dicer. In this embodiment, the sequences complementary to the signal-detecting strand are also complementary to one another, and act to elongate the duplex region further. Furthermore, the elongated duplex region may contain one or more mismatches or bulges that do not prevent Dicer cleavage and productive RISC loading. This may provide additional flexibility in terms of conferring sequence selection independence between the input/signal sequence and the siRNA/miRNA target.

In an alternative embodiment, the signal activated polynucleotide construct is degradation activated, in that binding of the signal polynucleotide to the complementary sequence on the signal-activated polynucleotide (the signal detecting sequence) induces cleavage of the signal activated polynucleotide constructs. For example, for DNA input strands, the formation of a DNA-RNA duplex can lead to the cleavage of the signal activated polynucleotide construct by RNAse H mechanisms. For RNA input strands, the resulting miRNA duplex can be cleaved by Ago2 mechanisms. Cleavage can also be mediated by allosteric ribozymes that are constructed into the loop regions of the two unstructured loop regions at the end of the optional additional duplex regions, and may be mediated by a nucleic acid binding event and/or the binding of some other factor (such as small molecule, peptide, etc.). To protect one portion of the stem regions from cleavage, at least 9 nucleotides of polyguanosine or other types of RNAse-resistant bases, such as 2'-OMe or LNA are signal-activated into the sequence adjacent or near to the sequence that will form the guide and passenger strands.

Once the loop regions have been cleaved, free 5' and 3' ends are created, which allows their degradation by processive exonucleases such as Xrn1 and exosome. Eventually, sequence that prevents the formation of the guide sequence/sense sequence duplex is degraded, resulting in a siRNA I miRNA, or a substrate for Dicer cleavage to generate such siRNA/miRNA.

In certain embodiments, however, generation of an active signal-activated polynucleotide construct does not necessarily require Dicer for a final activation step. In addition, in the tail degradation schemes described herein, nuclease processing after an initial signal-based cleavage step may not be necessary for productive RISC loading.

In some embodiments, the signal-activated polynucleotide construct is designed such that (i) in the absence of the signal polynucleotides, the signal detecting sequence hybridizes with one or more regions comprising part of the guide sequence and part of the sense sequence to create two additional duplex regions, wherein one of additional duplex regions is linked to a single-stranded loop with a nuclease-resistant sequence, and the other additional duplex regions is linked to a hairpin structure comprising two DNA segments, one on each strand of the hairpin structure, wherein the two DNA segments base pair with each other at about 2 nucleotides. On the other hand, in the presence of the signal polynucleotides, the signal detecting sequence hybridizes with signal polynucleotides, and disrupts the base pairing between the two DNA segments so as to allow RNase H to cleave an RNA sequence hybridized to one or both of the DNA segments.

In another related embodiment, a circular polynucleotide comprises three duplex regions joined at a three-way junction, wherein each end of the three duplexes opposite the three-way junction is linked by a single-stranded loop. Preferably, the loop is resistant to nuclease (e.g., the loop may comprise chemical modifications to resist nuclease digestion). In a related embodiment, each end of the three duplexes opposite the three-way junction is not linked by a single-stranded loop. Instead, nuclease-resistant polynucleotides (such as 16 nucleotides of polyguinosine) may be used to replace the loop functionality.

The three duplex regions of the construct, each individually or in combination, may not be good Dicer substrates because of short length (e.g., less than 19 bp) and/or chemical modifications (supra). One of the duplex regions may encode a siRNA/miRNA that targets a target gene. The other two arms of the construct may comprise an RNaseH cleavage signal—a DNA/RNA stretch (e.g., about 5 nt). Once the construct is in contact with RNaseH, these two arms can be digested by RNaseH to generate 3' or 5' ends, thus becoming susceptible for exonuclease digestion, which may lead to junction resolve. The resolved junction contains the duplex region that can be cleaved by Dicer to generate siRNA/miRNA, or the resolved junction may become the siRNA/miRNA without further Dicer processing. See FIG. 18.

In certain preferred embodiments, such as construct can be delivered in its inactive form to a given cell type via any art recognized transfection methods (naked injection of RNA, nanoparticle-mediated delivery, liposome, etc.). Lack of serum RNaseH activity in the media allows such a construct to remain stable until it is internalized by a target cell, in which cytoplasmic RNAseH may serve as the activating "signal" that cleaves the RNaseH cleavage signals, causing the three-way junction to resolve. Dicer generally cannot bind or process the uncleaved inactive circularized construct, but may or may not be needed to generate the siRNA I miRNA once the three-way junction is resolved.

In certain embodiments, the target sequence of the signal-activated polynucleotide construct may be fully independent of the input signal sequence. For example, in some embodiments, the signal-activated polynucleotide comprises (1) a guide sequence and a sense sequence capable of forming either an siRNA or an miRNA comprising the guide sequence, or a duplex region that can be cleaved by Dicer to generate the siRNA or miRNA, wherein the guide sequence is substantially complementary to a transcript of a target gene; (2) a blocking sequence capable of hybridizing with one or more regions comprising part of the guide sequence and/or part of the sense sequence; and (3) one or more signal detecting polynucleotides, each capable of hybridizing with one or more signal polynucleotides, wherein, (i) in the absence of the signal polynucleotides, the blocking sequence hybridizes with the one or more regions comprising part of the guide sequence and/or part of the sense sequence, wherein generation of the siRNA or miRNA, such as by Dicer cleavage, is inhibited, and/or productive incorporation of the siRNA or miRNA into RISC is inhibited; (ii) in the presence of the signal polynucleotides, the signal detecting polynucleotides hybridize with the signal polynucleotides, and allow the formation of the duplex region for the formation of the siRNA/miRNA, or cleavage by Dicer to generate the siRNA or the miRNA.

The blocking sequence structurally corresponds to the signal-detecting polynucleotide described in other embodiments above, but here it does not detect signal polynucleotides. Instead, the blocking sequence functions to inhibit the formation of a Dicer substrate and/or the formation of a molecule that can be loaded into RISC.

In certain embodiments; the signal detection sequence does not hybridize with the one or more regions comprising part of the guide sequence and/or part of the sense sequence. In certain embodiments, the inhibitor sequence does not hybridize with the signal polynucleotides.

In some embodiments, the presence of the signal polynucleotides leads to the hybridization between the signal detecting polynucleotides and the signal polynucleotides, thereby enabling hybridization of the blocking sequence with a compliment sequence. This base pairing relieves the inhibitory hybridization between the blocking sequence and one or more regions comprising part of the guide sequence and/or part of the sense sequence.

In other embodiments, the presence of the signal polynucleotides leads to hybridization between the signal detecting polynucleotides and the signal polynucleotides, which weakens the hybridization of the blocking sequence with one or more regions comprising part of the guide sequence and/or part of the sense sequence, and allows the formation of the duplex region.

In some embodiments, the signal-activated polynucleotide may be designed such that the absence of the signal polynucleotides leads to hybridization between a first part of the blocking sequence a region comprising part of the guide sequence to form a first additional duplex region and a first unstructured single-stranded region. Optionally, a second part of the blocking sequence may hybridize with a region comprising part of the sense sequence to form a second additional duplex region and a second unstructured single-stranded region. Conversely, the first part of the blocking sequence may hybridize to a region comprising part of the sense sequence to form a first additional duplex region and a first unstructured single-stranded region, whilst a second part of the blocking sequence may optionally hybridize with a region comprising part of the guide sequence to form a second additional duplex region and a second unstructured single-stranded region. Whatever the hybridization scheme, the signal-activated polynucleotide inhibits the generation of the siRNA or miRNA by Dicer when the signal polynucleotide(s) are absent. In these embodiments, one or more signal detecting polynucleotides may be located within first and/or second unstructured single-stranded regions.

The presence of the signal polynucleotides alters the hybridization between portions of the signal-activated polynucleotides of these embodiments. At least one of the one or more signal detecting polynucleotides may hybridize with the signal polynucleotides, and enable cleavage of the first and/or second unstructured single-stranded regions at one or more cleavage sites to create 5'- or 3'-OH groups. Creation of these 5'- or 3'-OH groups leads to degradation of the blocking sequence and the formation of siRNA or miRNA or formation of the duplex region for cleavage by Dicer to generate the siRNA or the miRNA.

In some embodiments, the signal-activated polynucleotides further comprise one or more stretches of nuclease-resistant sequences that inhibit the degradation of the duplex region. The stretches of nuclease-resistant sequences may comprise a stretch of at least about 9 nucleotides of polyguanosine, DNA, 2'-O-methyl modified nucleotide, or LNA.

In some embodiments, the cleavage at first and/or second unstructured single-stranded regions in the presence of signal polynucleotides may be mediated by an endonuclease. In other embodiments, the endonuclease may be an endoribonuclease. In further embodiments, the signal polynucleotides comprise DNA and the endoribonuclease is RNase H. For example, the signal polynucleotides may comprise output from artificial nucleic acid circuits (e.g., Enzyme-Free Nucleic Acid Logic Circuits. Seelig et al., Science 314: 1585-1588, 2006), DNA from the human genome, DNA from bacterial plasmids, DNA from genome integrating and non-integrating viruses, Mitochondrial DNA, DNA fragments from degradation of all of the above, and the degradation of the genome of other disease-causing organisms such as fungi or the malaria parasite.

In other embodiments, the endoribonuclease is RNase P, such as RNase P derived from bacteria, archaea, or eukaryotes.

Cleavage of unstructured single-stranded regions may be mediated by an endonuclease, and the endonuclease may be an endodeoxyribonuclease. In some embodiments, where both the signal polynucleotide and the signal-detecting sequence it binds to comprise DNA, the endodeoxyribonuclease may be a restriction endonuclease that cleaves dsDNA.

In some embodiments, the presence of signal polynucleotides leads to cleavage of unstructured single-stranded regions that is mediated by ribozymes. For example, a ribozymes may be a cis-acting hammerhead ribozyme that is incorporated into the first and/or second unstructured single-stranded regions, and is allosterically activated in the presence of the signal polynucleotides.

In some embodiments, the blocking sequence in a signal-activated polynucleotide is degraded by one or more exosomes and/or exonucleases. For example, the exonuclease Xrn 1 may degrade the blocking sequence.

In other embodiments, the signal-activated polynucleotide comprises two or more cleavage sites, at least two of which capable of being cleaved by different mechanisms.

The endonucleases described in these embodiments and the associate resistance mechanisms may also be applied to any other embodiments of signal-activated polynucleotides.

Another aspect of the invention provides a signal-activated polynucleotide construct that may be activated by degradation of a portion of the polynucleotide construct. Such a signal-activated polynucleotide construct may comprise: (1) a hairpin structure that comprises (a) a duplex region formed from a guide sequence and a sense sequence; and (b) a single-stranded loop linking the guide sequence and the sense sequence; wherein the duplex region can be cleaved by Dicer to generate an siRNA or an miRNA comprising the guide sequence, wherein the guide sequence is substantially complementary to a transcript of a target gene. Such a signal-activated polynucleotide further comprise (2) a single-stranded blocking sequence having a free end and is linked to the guide sequence or the sense sequence, wherein the blocking sequence comprises (c) a stretch of nuclease-resistant sequence at the free end that inhibits the degradation of the blocking sequence by exonuclease; and (d) one or more signal detecting polynucleotides, each capable of hybridizing with one or more signal polynucleotides.

In a related embodiment, the inactive construct does not comprise the duplex region formed between the guide sequence and the sense sequence. Instead, a blocking sequence linked to the sense sequence displaces the guide sequence for favorable hybridization with the sense sequence. See FIG. 19, panels A-B. This can be achieved because the hybridization between the blocking sequence and the sense sequence can be designed to be thermodynamically more stable that the alternative guide sequence/sense sequence hybridization. For example, the blocking sequence may have chemical modifications that enhances hybridization, or simply forms a longer duplex region due to the participation of extra nucleotide (such as those in the loop region when the guide sequence and sense sequence forms a stem-loop structure). Dicer cleavage of the blocking sequence/sense sequence is inhibited due to the presence of modified nucleotides, and/or the long terminal single-stranded sequences (one being the displaced guide sequence). The end (such as the 5' end) of the construct may comprise a polyguanosine stretch (e.g., >9 nt) or other nuclease-resistant bases (such as 2'-O-Me or LNA, etc.). Such a construct can be similarly activated via the RNaseH mechanism (if the signal polypeptide is DNA), via the Ago2 mechanism (if the signal is miRNA, or via cis-acting ribozyme allosterically regulated by a small-molecule-binding aptamer. Multiple signal detection sequences may be present on such a construct, including signal detection sequences present in the loop linking the blocking sequence and the sense sequence.

Once activated, the blocking sequence can be degraded by exo- and/or endo-nucleases, which does not degrade the sense strand for one or more reasons (supra). For example, there may be ribonuclease-unprocessible bases (e.g., 2'-O-Me, DNA, etc.) at the end of the sense sequence. Alternatively, the single-stranded region comprising the signal detection sequences may be DNA (outside of a potential miRNA cleavage region in case of a miRNA-mediated cleavage/activation), while the sense sequence may be an RNA. DNA exonucleases will stall at the end of the duplex region, and prevent or inhibit any RNases to degrade the dsRNA duplex formed between the sense and the guide sequences. Finally, nucleotide-type switching and linkage-switching (2')/blocking agents may also halt exonucleases at the sense sequence stem.

Similarly, the blocking sequence may be linked to the guide sequence (rather than the sense sequence) and forms a duplex region with the guide sequence. Similar design feature (e.g., the use of more nucleotides in the blocking sequence/guide sequence duplex, etc.) and activation schemes may be used in such embodiments. See FIG. 20, panels A-B.

Once activated, the blocking sequence can be degradated by exo- and/or endo-nucleases, which does not degrade the guide strand for one or more reasons (supra). For example, there may be ribonuclease-unprocessible bases (e.g., 2'-F, etc.) at the end of the guide sequence, which ribonuclease-unprocessible bases still permits RISC loading. Alternatively, the single-stranded region comprising the signal detection sequences may be DNA (outside of a potential miRNA cleavage region in case of a miRNA-mediated cleavage/activation), while the guide sequence, including its 2-nucleotide toehold, may be RNA. DNA exonucleases will stall at the end of the duplex region, and prevent or inhibit any RNases to degrade the dsRNA duplex formed between the sense and the guide sequences. Finally, nucleotide-type switching and linkage-switching (2')/blocking agents may also halt exonucleases at the toehold or the stem of the guide strand.

In these embodiments, the absence of signal polynucleotides leads to a conformation in which the blocking sequence inhibits proper Dicer cleavage of the duplex region and/or proper loading of the guide sequence in a Dicer cleavage product into a RISC complex. In contrast, the presence of signal polynucleotides leads to hybridization between at least one of the signal detecting polynucleotides and the signal polynucleotides, resulting in cleavage of the single-stranded blocking sequence at one or more cleavage sites to create 5'- or 3'-OH groups, degradation of the blocking sequence, and eventually, proper loading of the guide sequence in the Dicer cleavage product into the RISC complex.

The endonucleases described in previous embodiments may also be applied to these embodiments of signal-activated polynucleotides.

In certain embodiments, the duplex region formed between the guide sequence and the sense sequence is about 27 base pairs in length. In other embodiments, the guide sequence has a two-base pair nuclease-resistant sequence at its 5'-end. The two-base pair nuclease-resistant sequence may comprise 2'-F modification.

In other embodiments, the signal-activated polynucleotide construct comprises a single-stranded blocking sequence that further comprises deoxyribonucleotides and/or ribonucleotides. In other embodiments, the single-stranded blocking sequence is linked to the guide sequence. In alternate embodiments, the single-stranded blocking sequence is linked to the sense sequence.

To illustrate, an exemplary signal-activated polynucleotide may be protected from Dicer cleavage when the structures comprise a stem-loop structure formed by the nucleic acid guide strand and passenger strand, and further comprise a signal-detecting strand forming a tail at either the 3' or at the 5' end of the stem-loop hairpin. The signal-detecting strand may comprise a nucleotide sequence that is complementary to a signal polynucleotide. The signal-detecting strand may further comprise at least 9 nuclease-resistant bases, such as polyguanosine, 2'-OMe or LNA, preferably towards the free end of the tail. When the signal polynucleotide binds to the signal-detecting polynucleotide, cleavage of the signal-detecting strand by, for example, RNase H or other nucleases, may result. Cleavage may also be mediated by miRNA mechanisms, cleavage of DNA-RNA duplexes, or cleavage by a cis-acting allosteric ribozyme, depending on the signal polynucleotide and the mechanism signal-activated into the signal-detecting strand. Once the protective exonuclease-resistant nucleotides have been cleaved, either 5'- or 3'-OH groups are created. Endogenous and/or exogenous exonucleases digest the cleaved segment of the signal-activated polynucleotide. When a sufficient number of nucleotides have been truncated, the stem-loop structure can be cleaved by Dicer. Dicer cleavage should occur only when the 3' end (or the 5' end, depending on which end held the signal-detecting tail) has been sufficiently truncated.

Activation of a signal-activated polynucleotide may necessitate relaxation of steric hindrance formed by a blocking sequence. In another aspect, the invention provide a signal-activated polynucleotide construct comprising (1) a duplex region that can be cleaved by Dicer to generate an siRNA or miRNA that, in turn, inhibits the expression of a target gene via RNA interference mechanism; and (2) a blocking sequence that hybridizes with a portion of the signal-activated polynucleotide, and creates steric hindrance that inhibits Dicer cleavage of the duplex region; wherein the steric hindrance is relieved upon binding of a signal polynucleotide to the signal-activated polynucleotide, allowing the duplex region to be cleaved by Dicer to produce the siRNA or miRNA. Steric hindrance may also prevent loading of the signal-activated polynucleotide into RISC, whether or not cleavage by Dicer is necessary for generation of siRNA or miRNA.

In some embodiments, the duplex of the signal-activated polynucleotide is the stem of a stem-loop structure, and wherein the blocking sequence is within an overhang of the duplex region and hybridizes with the loop region of the stem-loop structure. Alternately, the signal-activated polynucleotide may comprise a second blocking sequence with a second overhang of the duplex region, and may hybridize with a second region in the loop region. The signal polynucleotide may hybridize with (1) a sequence in the loop region that does not hybridize with the blocking sequence, (2) a sequence in the loop region that does hybridize with the blocking sequence, or (3) a sequence in a linker that is between the blocking sequence and the end of the duplex region. In other embodiments, the signal polypeptide may hybridize with the sequence in the linker, which leads to cleavage of the linker and relief of the steric hindrance. The linker may be cleaved by cleaved by a cis-acting ribozyme, a trans-acting ribozyme, a DNase, an RNase, or a RISC complex.

These embodiments are partly based on the discovery that the activation state of a signal-activated polynucleotide may be partly dependent on the conformational dynamics of the RNA structure. For example, the inactive state of the signal-activated polynucleotide may be maintained such that the molecule cannot be cleaved by any of the Dicer family of proteins. This can be accomplished by way of using a blocking sequence that, when hybridized to the signal-activated polynucleotide, creates steric hindrance that prevents Dicer cleavage and productive loading into the RISC complex. For example, the blocking sequence may be operably linked to an end of the stem-loop structure of a shRNA or pre-miRNA. The blocking sequence may be complementary to a portion of the signal-activated polynucleotide nucleotide sequences found in the stem-loop structure, and moreover, may be also complementary to nucleotide sequences found in a signal polynucleotide. In the absence of a signal polynucleotide, the signal-detecting sequence binds to its complementary sequence in the stem-loop structure. The stem region may comprise at least 19 nucleotides (e.g., a potential Dicer substrate), while the complementary pairing of the signal-detecting sequence to the stem-loop structure is no more than 19 nucleotides (e.g., to prevent spurious Dicer cleavage and inadvertent activation of the potential Dicer substrate). The complementary pairing leads to the formation of a pseudoknot structure, comprising at least two helical segments connected by single-stranded regions or loops. In the presence of the pseudoknot, the stem-loop structure of the signal-activated polynucleotide is protected from cleavage by Dicer and incorporation into the RISC complex.

In order to switch the signal-activated polynucleotide into an active state, the pseudoknot structure must be resolved. Unknotting of the pseudoknot may be accomplished when a signal polynucleotide binds to one of three regions on the signal-activated polynucleotide. In one example, the signal polynucleotide binds to the signal-detecting nucleotide and displaces the pseudoknotting strand from the stem-loop structure. This exposes the stem-loop structure to cleavage by Dicer and processing by the RISC complex. In a second example, the signal polynucleotide binds to the signal-detecting nucleotide at a region upstream of the pseudoknot, causing compression and steric/electrostatic repulsion between the signal-detecting strand and the stem-loop structure. This causes dissociation of pseudoknotted region, and subsequent exposure of the stem-loop structure to the RNAi pathway. In a final example, the signal polynucleotide binds to complementary sequence in the loop region of the stem-loop structure. This binding induces strain into the signal-activated polynucleotide and so acts via indirect means to displace the signal-detecting strand from its pseudoknot binding. Displacement of the signal-detecting strand exposes the stem-loop structure to cleavage by Dicer and loading into the RISC complex.

In certain embodiments, the inactive, pseudoknotted form of the signal-activated polynucleotide may switch to an active form in the absence of a signal polynucleotide if the nucleotide region upstream of the pseudoknot is cleaved. The nucleotide region may be a linker between the end of the duplex region and the blocking sequence that binds to the signal-activated polynucleotide. In one example, the signal polynucleotide hybridizes to the linker, leading to cleavage of this double stranded structure. Following cleavage of the linker region, the pseudoknot structure is resolved and the duplex region is exposed to cleavage by Dicer. In another example, the linker sequence is cleaved by a self-cleaving ribozyme or aptamer switch that has been signal-activated to cleave upon binding of a factor or drug. After self-cleavage, the strand forming the pseudoknot eventually dissociates and diffuses away, although this step may not be necessary, provided that the stem-loop structure becomes accessible to Dicer cleavage and RISC binding.

In those embodiments where the signal-activated polynucleotide adopts a stem-loop structure, binding of the signal-activated polynucleotide to itself may create a pseudoknot that protects the stem region from Dicer cleavage. In the inactive form, the signal-activated polynucleotide features a large loop region that is long and flexible enough to hybridize to nucleotide sequences found in overhang regions at each end of the duplex region. This inactive, pseudoknotted form is switched to an active form if a signal polynucleotide mediates strand displacement reactions at both of these two sites and relieves the pseudoknot structure. Similarly, the pseudoknot is also relieved if the overhang regions undergo a cleavage reaction, mediated by ribozymes or aptamers.

Further, more complex gated pseudoknotted constructions of the signal-activated polynucleotides are made by binding arbitrary nucleic acid inputs or by incorporating self-cleaving ribozymes into sites in the loop region of the stem-loop structure or in sites near to or adjacent to the pseudoknot structure. A nucleic acid signal that displaces the binding of overhang regions to loop regions will relieve pseudoknot structures and switch the signal-activated polynucleotide to the active state. In addition, various sites in the loop region or in the overhang region may be designated as positions for self-cleaving ribozymes that can be activated by various factors or drugs. Cleavage at these strategic locations can relieve the pseudoknot structure and switch the signal-activated polynucleotide to the active form.

In some examples, the signal-activated polynucleotides are constructed such that more than one self-cleaving ribozyme is located in the molecule, and each self-cleaving enzyme is responsive to a different factor or drug. This creates gates that depend on a variety of different nucleic acids, drugs, and factors for activation. The overall molecule is thereby designed to make AND, OR, N-AND, N-OR, and other logic gates, or combinations thereof.

In other embodiments, the duplex region of the signal-activated polynucleotide comprises a mismatch that enables gross distortion of the duplex region upon binding of the blocking sequence to the portion of the signal-activated polynucleotide.

Dicer cleavage of a signal-activated polynucleotide may be inhibited by the presence of a blocking sequence, and may be made still more unfavorable by grossly distorting the structure of the duplex region. This can be accomplished by designing a single base (or a few base) mismatch in the stem structure. As in the examples above, switching between active and inactive forms of the signal-activated polynucleotides still relies on a signal, either the binding of a signal polynucleotide to the linker region, or on self-cleavage of the linker region. In either case, the active form of the signal-activated polynucleotide may be a stem-loop structure with at least 1 mismatched base pair in the stem region.

In some embodiments, the blocking sequence is a single stranded polynucleotide that hybridizes with both an overhang of the duplex region and the loop region of the stem-loop structure. For example, a single-stranded polynucleotide of about 20 nucleotides may be used to link the loop region of the signal-activated polynucleotide to sequence that overhangs the 5' end of the duplex region. In this example, the signal-stranded polynucleotide hybridizes to complementary sequences in both the loop region and the 5' overhang, forming a structure that Dicer cannot bind. To switch to the active state, the single-stranded polynucleotide must be removed. In one switching mechanism, a portion of a signal polynucleotide binds to the 5' overhang of the duplex, displacing the single-stranded polynucleotide and exposing the duplex region to Dicer cleavage. This active state may be switched back to the inactive state, if a portion of the unbound signal polynucleotide binds to single-stranded polynucleotide. This binding mediates release of a double-stranded product, and leaves the 5' overhang end free to bind to sequences in the loop region. When the 5' overhang binds to the loop region, the signal-activated polynucleotide is no longer accessible to Dicer cleavage.

In a related embodiment, the signal-activated polynucleotide is constitutively active, in that the potential blocking sequence that can hybridize with the loop region is "capped"/hybridized with another polynucleotide (the capping polynucleotide). However, a signal polypeptide might displace the capping polynucleotide, thus allowing the blocking sequence to hybridize to the loop region and create a steric hindrance to block Dicer processing and/or productive RISC loading.

In certain embodiments, activation of a signal-activated polynucleotide may require formation of a duplex structure and removal of sequences that block its formation. For instance, there may be at least 19 nucleotides available to form a duplex stem region, but the molecule adopts or is maintained in an inactive form because fewer than 19 nucleotides have paired to generate the stem. Instead, nucleotides at the 5' end are paired to single-stranded blocking sequence, and nucleotides at the 3' end form a single-stranded overhang. The blocking sequence may be a chimeric oligonucleotide, such that pairing of the signal-activated polynucleotide to the blocking sequence has more favorable free energy than the unpaired state. In order to switch the polynucleotide to its active form, the nucleotide sequence at the 5' end of the molecule must be separated from the blocking sequence. The separation is achieved by binding a signal polynucleotide to the blocking sequence, forming a duplex that drifts away. Subsequent formation of a full-length duplex stem in the signal-activated polynucleotide creates a molecule that can be cleaved by Dicer.

Similarly, the presence of an aptamer sequence at the 5' end of a stem region can also inhibit the formation of a full-length duplex, maintaining the signal-activated nucleotide in the inactive state. In order to switch the polynucleotide to its active state, the ligand for the aptamer is required to bind the aptamer and mediate a conformational switch. The change in conformation allows the full-length duplex region to form, thus generating a molecule that can be cleaved by Dicer.

Steric hindrance may inhibit the cleavage of a duplex region on the signal-activated polynucleotide. Thus another aspect of the invention provides a signal-activated polynucleotide construct comprising: (1) a guide sequence and a sense sequence forming a duplex region that can be cleaved by Dicer to generate an siRNA or an miRNA comprising the guide sequence, wherein the guide sequence is substantially complementary to a transcript of a target gene, plus (2) a signal detecting sequence that is capable of hybridizing with either (a) one or more signal polynucleotides, or, (b) one or more regions of the signal-activated polynucleotide other than the guide sequence and the sense sequence. In some embodiments, the signal-activated polynucleotide comprises a duplex region comprises that a mismatch, and a resulting bend of the duplex region that inhibits Dicer processing. In the absence of the signal polynucleotides, the signal detecting sequence hybridizes with one or more regions of the signal-activated polynucleotide, and creates steric hindrance to inhibit the cleavage of the duplex region by Dicer to generate the siRNA or miRNA. In the presence of the signal polynucleotides, the signal detecting sequence does not hybridizes with the regions of the signal-activated polynucleotide, and instead allows duplex region to be cleaved by Dicer to generate the siRNA or the miRNA.

In some embodiments, the duplex region of the signal-activated polynucleotide is within a stem-loop structure, and the signal detecting sequence hybridizes with the single-stranded loop region of the stem-loop structure in the absence of the signal polynucleotides. In some embodiments, the absence of a signal may lead the single-stranded loop region to hybridize with an overhang sequence of the duplex region. When present, signal polynucleotides may compete with signal detecting sequence for hybridization with the single-stranded loop region. In some embodiments, in the presence of the signal polynucleotide, the single-stranded loop region is cleaved to relieve steric hindrance and allows the duplex region to be cleaved by Dicer to generate an siRNA or miRNA. In other embodiments, signal polynucleotides hybridize with the signal detecting sequence. In further embodiments, the signal detecting sequence is linked to one end of the duplex region via a linker sequence. The linker sequences may hybridize with signal polynucleotides and eliminate the steric hindrance, ultimately allowing the duplex region to be cleaved by Dicer to generate the siRNA or the miRNA. In other embodiments, the presence of signal polynucleotides leads to the cleavage of the linker sequences, providing a different means to relieve the steric hindrance and allows the duplex region to be cleaved by Dicer to generate the siRNA or the miRNA. The linker sequence may be cleaved by an RNase H, an RNase P, a cis-acting ribozyme, a restriction endonuclease, or an miRNA-mediated mechanism.

In some embodiments, the signal-activated polynucleotide may comprise a signal detecting sequence that is an overhang of the duplex region, and one or more regions of the signal-activated polynucleotide is a separate single-stranded polynucleotide that hybridize to the overhang.

Signal-activated polynucleotides may be activated by the binding of an arbitrary nucleic acid molecule. In some embodiments, the signal-activated polynucleotide construct comprises two or more tandem stem-loop structures. Each stem-loop structure comprises (1) a guide sequence and a sense sequence forming a duplex region that can be cleaved by Dicer to generate an siRNA or an miRNA comprising the guide sequence, wherein the guide sequence is substantially complementary to a transcript of a target gene; and further comprises (2) a linker sequence linking two adjacent stem-loop structures. In the absence of the signal polynucleotides, the loop regions of the two adjacent stem-loop structures hybridizes with each other to create steric hindrance and to inhibit the cleavage of the duplex regions by Dicer to generate the siRNA or miRNA. In the presence of the signal polynucleotides, hybridization between the adjacent loop regions is disrupted to allow the adjacent duplex regions to be cleaved by Dicer to generate an siRNA or miRNA. In some embodiments, at least two of the duplex regions in the stem-loop structures are different. Thus, at least two distinct siRNA or miRNA products may be generated for the target gene. The siRNA or miRNA products may target the same gene or may target different genes.

In some embodiments, signal-activated polynucleotides comprising two tandem stem-loop structures may be constructed such that a pseudoknot structure is formed by hybridization of the sequences in the two loop regions. The steric hindrance created by this pseudoknot inhibits cleavage of the duplex region by Dicer, and the signal-activated polynucleotide is maintained in an inactive state. To mediate switching from the inactive state to an active state, the sequences in the loop regions of the two stem-loop structures may be constructed to contain an aptamer switching sites. Upon binding of the aptamer to its ligand, or the binding of one or more signal polynucleotides to sequence in one or both of the loop regions, the pseudoknot dissociates. Without the pseudoknot structure, the two stem-loop structures separate and each become substrates for cleavage by Dicer and processing by the RISC complex.

Thus another aspect of the invention provides a signal-activated polynucleotide construct comprise two or more tandem stem-loop structure, each comprising: (1) a guide sequence and a sense sequence forming a duplex region that can be cleaved by Dicer to generate an siRNA or an miRNA comprising the guide sequence, wherein the guide sequence is substantially complementary to a transcript of a target gene; and (2) a linker sequence linking two adjacent stem-loop structures. In the absence of the signal polynucleotides, the loop regions of the two adjacent stem-loop structures hybridize with each other to create steric hindrance and to inhibit the cleavage of the duplex regions by Dicer to generate an siRNA or miRNA. In the presence of the signal polynucleotides, hybridization between the signal polynucleotides and the linker sequence results in the cleavage of the linker sequence and the relief of the steric hindrance, and allows the adjacent duplex regions to be cleaved by Dicer to generate an siRNA or miRNA.

In some embodiments, a signal-activated polynucleotide may be maintained in the inactive state when it comprises two or more tandem stem-loop structures that are (1) linked to one another through a linker sequence continuous with each other, and (2) attached at the loop regions by a psuedoknot. The steric hindrance created by the pseudoknot inhibits Dicer from cleaving any of the stem-loop structures. Switching this molecule to the active state requires the linker sequence to serve as a target for miRNA. First, a signal nucleotide binds to the linker sequence, and forms a short duplex structure. This structure may be cleaved by Dicer, after which the stem-loop structures are no longer linked together at the base. Initially, the pseudoknot structure may connect the loop regions of the individual stem-loop structures, but the stem regions are accessible to Dicer cleavage and RISC complex processing. One or more of the stem regions may be cleaved and processed. Eventually, the pseudoknot dissociates, allowing the two stem-loop structures to separate.

The pseudoknotted stem-loop structures may also separate when the linker sequence is constructed as a self-cleaving ribozyme. Specifically, the ribozyme is constructed to cleave itself when a factor or a drug has bound to an aptamer domain in the ribozyme. As in the example above, the cleavage of the sequence intervening between the bases of the two stem-loop structures separates the stem-loop structures at the base. Once separated, one or more of the stem-loop structures are accessible to Dicer and the RISC complex.

Biophysical constraints in the signal-activated polynucleotides can also control the switching between active and inactive states of the nucleotides. Thus the invention provides a signal-activated polynucleotide construct comprising: (1) a guide sequence and a sense sequence capable of forming a duplex region that can be cleaved by Dicer to generate an siRNA or an miRNA comprising the guide sequence, wherein the guide sequence is substantially complementary to a transcript of a target gene; and, (2) a single-stranded linker sequence linking the guide sequence and the sense sequence. In the absence of one or more signal polynucleotides, the linker sequence hybridizes with a blocking polynucleotide (or signal detection polynucleotide) to create steric hindrance and inhibit the formation of the duplex region and the generation of the siRNA or miRNA by Dicer. However, in the presence of the signal polynucleotides, the signal polynucleotides hybridize with the blocking sequence to remove the steric hindrance and allows the formation of the duplex region for cleavage by Dicer to generate an siRNA or miRNA. In some embodiments, the single-stranded linker sequence that links the guide sense and sense sequences may comprise the blocking sequence.

Thus, an exemplary embodiment (see the Reverse Rip Loop scheme, FIG. 24, panels A-C) may be envisioned in which the signal-activated polynucleotide comprises a nucleic acid that is capable of forming a stem-loop structure, wherein the stem region of the hairpin is at least 19 bp (preferably a Dicer substrate). The loop region may be a single-stranded linker sequence between the guide sequence and the sense sequence. The signal-activated polynucleotide may be maintained in an inactive state when the linker sequence hybridizes with the blocking polynucleotide (or signal detection polynucleotide), and the steric hindrance created by this hybridization inhibits the formation of the full-length duplex between the guide sequence and the sense sequence (See Reverse Rip-Loop, FIG. 24, panels A-C). Specifically, fewer than 19 nucleotides, preferably fewer than 15 nucleotides may be able to form a partial duplex in the stem region because the linker sequence is bound to a blocking polynucleotide in the inactive state. In this example, a blocking polynucleotide may be a nuclease resistant sequence, such as an RNA molecule that has been modified into locked nucleic acid (LNA). Similarly, the single-stranded regions in the construct that are not in the partial guide sequence-sense sequence duplex, and not in the blocking polynucleotide duplex may be chemically modified so that such regions are also nuclease resistant.

To switch this signal-activated polynucleotide to an active state, the LNA or other blocking polynucleotide must be displaced. Strand displacement of the blocking polynucleotide may be achieved upon binding of the blocking polynucleotide to one or more signal polynucleotides, leading to partial or complete removal of the steric hindrance that previously inhibits the formation of the full-length guide I sense sequence duplex. This allows the extension of the previously partial duplex region to a longer stem, preferably a stem longer than 21 bp, which can then be cleaved by Dicer. To facilitate or initiate the hybridization between the incoming signal polynucleotides and the blocking polynucleotide, one or more single-stranded toehold regions may exist at the ends of the blocking polynucleotide duplex, which toehold regions may initiate hybridization events with the incoming signal polynucleotides.

Optionally, to prevent spurious loading of the sense sequence into RISC, the 5'-end of the sense sequence may be blocked by any of the RISC loading inhibitor described herein.

In similar exemplary embodiment, the duplex region of a signal-activated polynucleotide cannot form because linker sequence that is continuous with the guide sequence and the sense sequence further also comprise the blocking sequence. In this configuration, the linker sequence effectively binds to itself, creating steric hindrance that inhibits formation of the full-length duplex. The polynucleotide is maintained in the inactive state until this binding in the linker sequences is reversed. Reversal requires either strand displacement of the bound linker sequences or ribozyme cleavage in the linker region, mediated by aptamer switching. In either case, removal of the steric hindrance generated by binding in the linker sequences leads to the formation of a full-length duplex stem. This full-length stem can be cleaved by Dicer and processed by the RISC complex.

A variation of the same molecule features a stem that is unable to form a stem region of the requisite 18 or more nucleotides, due to the presence of one or more 3' to 5' inversion of nucleotide sequence in the linker region. Following strand displacement or aptamer switching at suitable sites in the linker, the signal-activated polynucleotide forms a stem region of at least 19 nucleotides, plus a loop structure. The loop may be bound to the signal polynucleotide that participated in the initial strand displacement reaction. Regardless, stem-loop structure is switched to the active form when the stem region becomes accessible to Dicer cleavage and processing by the RISC complex.

A signal-activated polynucleotide may be activated by ligation, in a mechanism that depends on the input of an RNA oligonucleotide. Such a signal-activated polynucleotide construct may comprise: (1) a stem-loop structure comprising a double-stranded stem region and a single-stranded loop region, wherein one end of the stem region comprises a single-stranded overhang; and (2) a single-stranded second polynucleotide that hybridizes to the overhang to form an overhang duplex, wherein a single-stranded gap region links the overhang duplex to the stem region. In the absence of the signal polynucleotides, the linker sequence hybridizes with a blocking polynucleotide to create steric hindrance and inhibit the formation of the duplex region and the generation of the siRNA or miRNA by Dicer. However, in the presence of a signal polynucleotides, the signal polynucleotides hybridizes with the single-stranded gap region and becomes covalently linked to the overhang duplex and the stem region to create a continuous duplex region, wherein the continuous duplex region is capable of being cleaved by Dicer to generate an siRNA or an miRNA that mediates sequence-dependent gene silencing of a target gene.

Thus, in some embodiments, a strategy to maintain the inactive state of the signal-activated polynucleotide is the omission of nucleotides from the stem region of the stem-loop structure. This can be accomplished in a signal-activated polynucleotide in which one end of a double-stranded stem region has a single-stranded overhang. The overhang, in turn, is hybridized to a single-stranded second polynucleotide, such that a gap region links the overhang duplex to the stem region. Because of the gap region, the polynucleotide is not an active form that can be cleaved by Dicer. To switch this molecule to the active state, input from a signal nucleotide is required. A signal polynucleotide hybridizes to the gap region and becomes covalently linked to the overhang duplex and the stem region. RNA ligases seal the nicks. Standard RNA ligases are used if the signal-activated polynucleotide has been constructed with adenylated 5' ends. Notably, pre-adenylated 5' ends can also be used in order to facilitate use of adenylation-deficient RNA ligases. Such ligases are safer to use for in vivo applications, although wild-type RNA ligase may also be used with non-adenylated nick 5'-end. When the completed stem-loop structure has been formed, the signal-activated polynucleotide is in the active form for Dicer cleavage and RISC complex processing.

Another aspect of the invention provides a signal-activated polynucleotide construct comprising a duplex region of less than 19 base pairs in length, wherein hybridization of the signal-activated polynucleotide with a signal sequence creates a duplex region of at least 19 base pairs in length. This duplex region may be capable of being cleaved by Dicer to generate a siRNA or miRNA that inhibits the expression of a target gene using an RNA interference mechanism.

In some embodiments, sequence homology between the duplex region of a signal-activated polynucleotide and the signal polynucleotide provides the basis for switching between activation states. For example, a stem region of 24 nucleotides may be incomplete because one strand of the duplex is missing at least one nucleotide. In the absence of a fully-formed duplex, the molecule is maintained in its inactive state and will not be cleaved by Dicer. To switch to the active state, the signal-activated polynucleotide binds to a complementary signal polynucleotide, which replaces the strand that does not share full complementarity.

In a similar scheme, the stem region of a signal-activated polynucleotide has at least 1 mismatched base pair. As in the previous example, this polynucleotide is maintained in the inactive state and will not be cleaved by Dicer. If the polypeptide has been signal-activated to include a 5' overhang region, however, it can be switched to the active state. Binding of the 5' overhang region to a signal polynucleotide leads to strand replacement, whereby the signal polynucleotide replaces one strand of the mismatched duplex. In the final stem duplex, at least 19 nucleotides are completely and complementarily base-paired, forming a substrate for Dicer cleavage.

Another aspect of the invention provides a signal-activated polynucleotide construct comprising a duplex region having one or more mismatches that inhibits the duplex region from being cleaved by Dicer, wherein hybridization of the signal-activated polynucleotide with a signal sequence creates a duplex region; the duplex region capable of being cleaved by Dicer to generate an siRNA or miRNA that inhibits the expression of a target gene using an RNA interference mechanism.

Thus, the signal-activated RNA polynucleotides may be maintained in the inactive state when mismatches in stem region of the stem-loop structure inhibit Dicer cleavage. The mismatches inhibit cleavage even when polynucleotides are as long as 38 nucleotides. In order to mediate switching to the active state, the signal-activated polynucleotide is constructed with extra nucleotides as an overhang and a nuclear export signal at the 3' of the sequence. Binding of a signal polynucleotide to the 3' overhang and to nucleotides in the mismatched stem region is required for switching. In this case, the signal polynucleotide is a cDNA molecule. The cDNA base pairs with its RNA complement, resulting in a duplex stem comprising the cDNA and the 3' portion of the original RNA duplex polynucleotide. At the same time, the opposing strand of the original RNA duplex folds into a stem-loop structure, owing to complementary sequences that are signal-activated into the molecule. The modified molecule is reconfigured in the active state, as the RNA stem-loop becomes a substrate for Dicer, whilst the cDNA-RNA duplex becomes a substrate for RNAse H.

In certain embodiments, the signal-activated polynucleotide adopts an inactive conformation when crossovers between the duplexes of two double-stranded RNA molecules hold the two double-stranded molecules together. The crossovers are signal-activated so that each duplex comprises at least 19 nucleotides of sequence. One duplex has at least one mismatched base pair within this sequence of 19 nucleotides. The position of the two crossovers applies enough strain to cause the two double-stranded duplexes to twist together into a helical twist. To switch this signal-activated polynucleotide to the active state, a signal polynucleotide is required. The signal polynucleotide is a cDNA strand that is complementary to the nucleotide sequence in the duplex that contains the one or more mismatched base pairs. Binding of this sequence to the cDNA is favored over binding to the mismatched base pairs, and the crossovers are resolved. The active conformation of the molecule is the remaining double-stranded RNA molecule, now linked to a new duplex structure of cDNA and RNA. The cDNA-RNA duplex is a target for RNAse H, whilst the double-stranded RNA molecule is an active substrate for Dicer.

In some embodiments, circularization of the signal-activated polynucleotide is a simple scheme to inhibit Dicer cleavage. Thus another aspect of the invention provides a circular signal-activated polynucleotide construct comprising a duplex region of at least 19 nucleotides, and may further comprise two single-stranded loop regions, one at each end of the duplex region, wherein one or both of the loop regions can hybridize with a signal polypeptide. In the absence of the signal polypeptide, the duplex region is not a Dicer substrate. However, in the presence of the signal polypeptide, the one or both loop regions hybridize with the signal polypeptide and enables cleavage of the loop regions, wherein the duplex region becomes a Dicer substrate upon cleavage of one or both loop regions, and wherein cleavage of the duplex region by Dicer produces an siRNA or miRNA that inhibits the expression of a target gene through an RNA interference mechanism.

In some exemplary embodiments, a duplex region of at least 19 nucleotides is continuous with single-stranded loop regions at each end of the duplex regions. One or both of the loop regions can hybridize with a signal polynucleotide. This molecule is maintained in the inactive state and cannot be cleaved by Dicer. To switch to the active state, a signal polynucleotide such as cDNA binds to complementary sequence in one of the loops. A cDNA-RNA duplex is a substrate for RNAse H. Alternatively, if the signal polynucleotide is RNA, the resulting RNA-RNA duplex is a substrate for processing in a RISC complex. As an additional alternative, ribozymes and cleavable linkers and aptamers can be used. The cleavage of the duplex formed in the loop region is designed to leave a 3' overhang of 2 nucleotides, which forms a suitable binding site for Dicer. The removal of one loop via signal polynucleotide binding acts as the switch to the active state of the polynucleotide, as the resulting structure is a duplex region with a single loop, a substrate for Dicer.

Additional embodiments relate to methods for inhibiting expression of target genes. In some embodiments, expression may be inhibited by using a method that comprises providing an effective amount of the signal-activated polynucleotide construct described above, and at least one signal polynucleotides. In some embodiments, the target gene is within a cell. In other embodiments, any of the signal-activated polynucleotide constructs described above contact a cell in vitro. Such a cell may be that of is that of a human, a non-human primate, a non-primate mammal, a rodent, a livestock animal, a bird, an insect (e.g., fly), a worm, or a plant.

Another aspect of the invention provides a pharmaceutical composition comprises an effective amount of one or more of the signal-activated polynucleotide constructs described herein, and a pharmaceutically acceptable amount of excipients, carriers, or diluents. In some embodiments, a mixture of different signal-activated polynucleotides may be present in the pharmaceutical composition. In any given pharmaceutical composition, the number of signal polynucleotides and/or the number of target sequences can be varied. One or more distinct signal-activated polynucleotides may target the same sequence on a target gene, or may target different sequences on a target gene. Alternately, one or more distinct signal-activated polynucleotides may each target different target genes. Different target genes may have the same target site, or may have different target sites. In other embodiments, signal-activated polynucleotides that target identical or similar sequences may be triggered by the same signal polynucleotides, or may be triggered by different signal polynucleotides.

Two or more stem-loop structures may be signal-activated into the loop region of a primary stem-loop structure. Because the primary stem region contains at least 19 nucleotides, the primary stem could be a substrate for Dicer, if not for steric hindrance provided by the presence of the two or more stem-loop structures. Because of the steric hindrance, the molecule is maintained in an inactive state. The intersection of the three stems, meanwhile, comprises a single-stranded linker region that contains either an aptamer or a binding site for a signal polynucleotide. Binding to the linker region, either through binding of aptamer to its ligand or binding of a signal polynucleotide to the linker causes the two or more stem-loop structures to open into a large loop. The signal-activated polynucleotide is switched to the active form when the primary stem-loop structure is no longer sterically hindered.

In a variant of the multiple-stem structure, the primary stem-loop hairpin structure comprises a stem region of at least 22 complementary base pairs, but only 18 or fewer base pairs form the stem. The remaining base pairs are branched out to form two additional stem-loop hairpin structures. One of these stem-loop structures comprises only the 4 additional base pairs. Supporting this small, 4-base pair containing stem is another stem-loop structure, which comprises the 4 additional base pairs in a stem structure, and further comprises 15 or more additional base pairs in the same stem, and an aptamer site in the loop region. Because the primary stem region is not long enough to be a Dicer substrate, the molecule is maintained in the inactive state. To switch the molecule to the active state, a signal polynucleotide is required. The signal polynucleotide binds to its complement in the larger of the two additional stem-loop structures. This binding causes the additional stem loop structures to open, and the primary stem region is now able to base pair along the entire 22 or more complementary base pairs. Thus paired, the molecule may be cleaved by Dicer.

Signal-activated polynucleotides are maintained in the inactive state when they comprise a stem-loop structure that forms a pseudoknot with a long single-strand of nucleic acid. The single strand of nucleotides can be a 5' overhang of the duplex region. The single strand associates with the duplex region via Coulomb attraction, and penetrates the major and minor grooves of the stem. The twisted backbone configuration of the overall molecule makes it incompatible with the binding domain in Dicer. In addition, the single strand forms a pseudoknot in the loop region of the stem-loop structure. The sequence of the single strand of nucleic acid around the pseudoknot may be constructed to comprise an aptamer position or modified bases that confer a positive charge. Formation of this pseudoknot, or activity of the aptamer, mediate switching to the active form of the signal-activated polynucleotide. When a signal polynucleotide binds to complementary sequence in the single strand of nucleic acid, or when a ligand binds to the aptamer, the psuedoknot is dissociated. After the pseudoknot has been dissociated, the stem region of the stem-loop structure can be cleaved by Dicer.

Signal-activated polynucleotides constructed with at least one nucleotide modified with poly-ethylene glycol (PEG) may modulate switching between active and inactive states. Here, the signal-activated polynucleotide folds into a stem-loop structure and further comprises (1) a signal-detecting sequence that is complementary to the loop region and (2) PEG-modification of at least one nucleotide at the 5' end of the molecule, which confers weak association between the modified nucleotides and the major/minor grooves of the stem region. An aptamer region could also be added to the signal-detecting strand, where it binds to the loop region of the signal-activated polynucleotide. Between the binding of the signal detecting strand to the loop region and the weak association between the PEG-modified nucleotides and the stem region, the signal-activated polynucleotide is held in the inactive state. However, upon binding of the signal-detecting strand to either a signal polynucleotide or a ligand for an aptamer, both constraints are removed from the stem region and the loop region. The molecule switches to the active state, and may be cleaved by Dicer.

In some embodiments, signal-activated polynucleotides target the 3' UTR of target mRNAs if the sequence of the signal-activated polynucleotides is complementary to the sequence in the 3' UTR. The target sequence comprises short stretches of nucleotides that form secondary structures such as stem-loop structures. The signal-activated polynucleotide, meanwhile, is constructed of nucleotides that are complementary to the sequences in the stem-loop structures of the target mRNA. Because the signal-activated polynucleotide also therefore contains sequences that can form a stem-loop structure, it too folds into a duplex stem-loop structure. In the presence of this structure, the molecule is held in the inactive state, since the region that will bind to the mRNA is sequestered in a duplex. The molecule is switched to the active state in the presence of either a signal polynucleotide that will open the duplex stem-loop structure of the signal-activated polynucleotide, or else a ligand for an aptamer that has been signal-activated into the polynucleotide. In either case, the signal-activated polynucleotide adopts the active conformation when it has been opened and binds to the target 3' UTR of the mRNA.

Another aspect of the invention provides a vector encodes the signal-activated polynucleotide constructs described above.

Another aspect of the invention provides a cell comprises the signal-activated polynucleotide constructs described above.

Another aspect of the invention provides a non-human organism comprises one or more cells that further comprise the signal-activated polynucleotides described above.

Another aspect of the invention provides a molecular signaling network or circuit, comprises (1) one or more input signals; (2) one or more signal-activated polynucleotide constructs or vectors as described above, wherein each of the constructs is independently capable of being activated by at least one of the input signals, as manifested by the production of the siRNA or miRNA, and, (3) one or more target gene transcripts, wherein the expression of the target gene transcripts is inhibited by the siRNA or miRNA. Such molecular signaling network or circuit may be used to engineer an intracellular signaling network, in which one or more input signals may be used to predictably control (inhibit or enhance) the expression of heterologous genes.

II. Additional Features of the Signal-Activated Polynucleotide Constructs

This section provides additional features that may be generally applicable to all embodiments of the invention described above, and may be combined with any of the features described herein.

a) Inhibiting/Blocking RISC Loading

In certain embodiments, the subject signal-activated polynucleotide constructs are designed to have regions that are resistant to Dicer cleavage and/or productive RISC loading (e.g., either not loaded into RISC at all, or substantially not functional even if loaded into RISC). Such regions may include parts of the construct that are potential but not intended Dicer substrate, and regions designed to be part of the Dicer substrate only in the presence of the signal (polynucleotide). For example, in the absence of the signal (polynucleotide), the partial duplex region formed between the guide sequence and the sense sequence should not be cleaved by Dicer or productively loaded into RISC. Any of the means described below may be used to inhibit Dicer cleavage and/or productive RISC loading. In the presence of the signal (polynucleotide), the duplex region between the guide sequence and sense sequence may be extended by the formation of additional duplex regions, resulting in a longer duplex region that can be cleaved by Dicer. Alternatively, in the presence of the signal (polynucleotide), the 3'-end of the guide sequence and the 5'-end of the sense sequence may be created by a degradation event (such as degradation by exo- and endo-nucleases in the subject degradation-activated constructs).

The simplest modification to block entry into RISC may involve just a hairpin at the 5' end of the guide strand. To prevent the cleavage of the hairpin loop region by nucleases, chemical modifications (2'-O-methyl/fluoro, or LNA, etc.) may be used in the loop region. There are many other art-recognized 5' end, 3' end, or internal base modifications that will inhibit Dicer cleavage and/or RISC loading. Such modifications can all be used in the subject constructs.

In general, almost all modification blocking the 5' end (or 5'-phosphorylation) of the guide/antisense strand significantly inhibits RISC processing/loading. Merely to illustrate, Schwarz et. al. (Mol. Cell 10: 537-548, 2002) showed that placement of a methyl group at the 5' end (5'-OMe) of the guide strand abolishes RNAi activity in *Drosophila* extracts and in HeLa cells. But when a 5'-modification containing a properly positioned phosphate group (e.g., 6-amino-hexyl phosphoester), RNAi activity was restored. See also Chiu & Rana, Mol. Cell 10: 549-561, 2002, which shows that inverted deoxyabasic residues on the 5' end of the guide strand abolishes RNAi activity, and that a 5'-aminopropyl phosphodiester on the guide strand abolished RNAi activity. Thus, it seems that any modification at the 5' end of the guide strand inhibits RNAi, except in rare cases where an appropriately positioned phosphate group is at the 5' end. See *RNA Interference: RNA Interference*, By David R. Engelke, John J. Rossi, Contributor David R. Engelke, John J. Rossi (Published by Academic Press, 2005, ISBN 0121827976, 9780121827977, incorporated by reference) and *RNA Interference Technology: From Basic Science to Drug Development*, By Krishnarao Appasani, Andrew Fire, Marshall W. Nirenberg, Contributor Andrew Fire, Marshall W. Nirenberg (Published by Cambridge University Press, 2004, ISBN 0521836778, 9780521836777, incorporated by reference).

To inhibit Dicer cleavage and/or productive RISC loading, one can also use DNA (and other modified bases such as 2'-fluoro, 2'-methyl, 2'-O-allyl, LNA, etc.) with 5' hydroxyls at the 5' end, so long as the modified nucleotides are poor substrates for endogenous kinase. See, for example, Amarzguioui et. al. (*Nucleic Acid Research* 31: 589-595, 2003, showing that 2'-allyl modifications inhibit kination of the 5'-hydroxyl group and RISC activity); and Schwartz (supra, showing that target cleavage is significantly inhibited when the 5' end was capped with a 2'-deoxy dT base with a hydroxyl group, but that the effect was reversed with chemical 5' phosphorylation of this DNA base).

In contrast, as to the 3' end, except for rare cases involving special bulky groups, modifications of 3' end on the guide or passenger strand, or modification of the 5' end of the passenger strand do not seem to have much of an effect on RNAi activity. For example, Chiu & Rana (supra) ruled out puromycin and biotin conjugations on the 3' ends of the guide/passenger strand as RISC inhibitors. The known special exceptions include: 3'-fluorescein (or other dyes/bulky groups), see Harborth et al., *Antisense Nucleic Acid Drug Dev.* 13(2): 83-105, 2003; and 2'-O, 4'-O-ethylene thymidine (eT) & 2-hydroxyethylphosphate modified thymidine (hp), see Hamada et al., *Antisense Nucleic Acid Drug Dev.* 12(5): 301-309, 2002 (showing that the only tolerated modification was a single 3' modification by one of these moieties on the sense/passenger strand—any such modified nucleotides at the 3' end of the guide/antisense strand totally abolished RISC activity).

Other modifications, such as adding bulky groups (e.g., PEG) may also be used to prevent spurious Dicer cleavage/RISC loading.

As to internal base modifications, Chiu & Rana (*RNA* 9: 1034-1048, 2003, incorporated by reference) provides a table of internal base modifications that are tolerated for RNAi (or to what extent such modifications can be tolerated). According to this table, uniform deoxy (i.e. DNA-base) modification or 2'-OMe modification of the guide strand is not tolerated, and is only very poorly tolerated on the passenger strand. N3-methyl uridine (3MU) modification, which contains a large bulky group that will protrude into the major groove and disrupt H-bonding, also abolishes RNAi activity even when only placed at the 11th nucleotide from the 5' end of the guide strand.

In certain embodiments, chemical crosslinking (i.e., formation of diadducts between strands) of certain duplex regions, such as crosslinking the strands nearest the 5' end of the guide strand (where duplex unwinding is initiated), can be used to inhibit Dicer cleavage and/or productive RISC loading. See Chiu & Rana (*Mol. Cell* 10: 549-561, 2002, incorporated by reference). Psoralen or certain photo-crosslinking modifications (e.g., opposing halogenated bases/intercalating groups, etc.) may be used to crosslink duplex regions. In addition, chemical or polymer groups may be used to cross-link one end of a double-stranded region.

In yet other embodiments, a duplex region of the subject construct not intended to be a Dicer substrate or properly loaded into RISC may be made artificially long (e.g., >30 nucleotides) to inhibit RNAi activity even if such region is spuriously loaded into RISC. For example, base modification may be used to inhibit Dicer cleavage of such long duplex regions.

b) RNAi in the Nucleus/Sensing Targets in the Nucleus

The RISC complex, though loaded cytoplasmically, may be imported into the nucleus for certain nuclear targets. See, for example, Ohrt et al., *Nucleic Acids Res.* 36(20): 6439-6449, 2008. Nuclear import moieties are known in the art. See, for example, Hwang et al., *Science* 315: 97, 2007, describing a hexanucleotide 3' end motif (AGUGUU), and a relaxed consensus sequence (AGNGUN, where N is any nucleotide), which are capable of directing nuclear import of any given microRNA. In addition, 2'-O-methyl modifications can be used to direct nuclear import.

Thus, in certain embodiments, the subject signal activated polynucleotide constructs may comprise one or more moieties for directing nuclear import.

In one embodiment, the subject activated constructs with such nuclear import moiety may be imported into the nucleus to target certain nuclear targets.

In another embodiment, the subject constructs may be imported into the nucleus to be activated by certain nuclear signals, including spliced or unspliced mRNA, small molecules for the ribozymes, introns, and other nuclear signals, etc. This can be achieved by using signal detection sequences that interact/bind/hybridize with such signals. For example, CD4$^+$ cells that are latently infected with HIV have unspliced or spliced transcripts that are retained in the nucleus (see "Nuclear Retention of Multiply Spliced HIV-I RNA in Resting CD4+ T Cells" by Lassen et al., PLoS Pathog. 2(7): e68, 2006). The subject constructs capable of sensing such nuclear signals can be used to reduce the number of latently infected cells (without activation) in an HIV-positive individual.

Elongated 5' tail on siRNA/shRNA can be used in such constructs since they disrupt Exportin 5 shuttling out of the nucleus. See Zeng et al., Nucleic Acids Res. 32(16): 4776-4785, 2004. Thus, the subject saRNA constructs can be engineered to have longer 5' tails (such as in the tail degradation scheme), multiple 2'-O-methyl modifications in single-stranded or duplex regions, and/or even a protein nuclear localization tag to direct nuclear import. Once the constructs are in the nucleus, they can be activated and then be shuttled out into the cytoplasm as an activated construct, which can target certain cytoplasmic targets.

Nuclear import of saRNAi via an elongated 5' tail has an added advantage of blocking spurious RISC loading, and prevents premature/false-positive activation of the subject constructs.

In certain embodiments, certain introns inside the nucleus can be the signal that activates the subject constructs. Preferably, activation of the subject constructs also removes (e.g., via ribozyme cleavage, or degradation schemes, etc.) the nuclear localization signal (e.g., protein-based, or extended 5' end, etc.) to facilitate the export of the activated construct into the cytoplasm.

c) Deoxyribozymes/Ribozymes Used in saRNAi Activation Schemes

In certain embodiments, certain aptamer domains may be used in the subject constructs to sense/detect small molecule signals, protein subdomains, etc. For example, an allosteric deoxyribozyme or ribozyme may be used in the degradation-activated saRNA constructs, such that upon binding of the signal to the aptamer, the cis-acting deoxyribozyme or ribozyme effects cleavage in the loop region and initiates nuclease degradation-mediated activation of the subject saRNA constructs.

In certain embodiments, constructs comprising the allosteric deoxy/ribozymes may produce a direct-to-Dicer (e.g., constructs that can be directly cleaved by Dicer)/direct-to-RISC (e.g., constructs that can be directly loaded into RISC without first cleaved by Dicer) product without the need for additional nuclease processing.

d) Blocking RNase-A Degradation in Serum

RNase A works by catalyzing the cleavage of a P—O5' bond on the 3' side of a pyrimidine residue (i.e., cytosine or uridine). Thus, in certain embodiments, the subject constructs contain RNase A-resistant single-stranded regions, in which the sequences of such regions are restricted to concatenations of guanosine, adenine, and other modified bases (such as 2'-O-methyl, 2'-fluoro, LNA, DNA, etc.). Similar sequence modifications may also be used to create regions that are resistant to other serum exonucleases.

e) Fully Single-Stranded Signal Detection Domain (i.e. Rip-Loop)

In certain embodiments, once the input signal hybridizes with the signal detection sequence in the loop region, a strong thermodynamic gradient is formed for dissociating the blocking sequence or for resolving the three-way junction that blocks Dicer processing. Preferably, the hybridization creates a duplex region that forms about 3, e.g., about 2.5-3.5 base-pairs for every one that splits apart on duplex region of the mask/junction-arm.

To provide an illustrative example, a single-stranded signal detection sequence with 3N nucleotides may be used to dissolve ("rip apart") a double-stranded region of N nucleotides (optionally connected to a downstream duplex region). This is partly because the base-to-base distance is different between two contiguous nucleotides in a single-stranded loop vs. the same nucleotides in a double-stranded duplex. Specifically, the base-to-base distance between any two contiguous nucleotides (DNA or RNA) is about 0.43 nm, while this distance is shortened when the same nucleotides are in a DNA/RNA/hybrid duplex. Therefore, for each pair of nucleotides "split apart" because of the formation of dsRNA (with a base-to-base distance of 0.26 nm, in A-form duplex), about 3.3 bp of dsRNA is needed for each by of split (0.43×2/0.26=~3.3). Similarly, for each pair of nucleotides "split apart" because of the formation of dsDNA (with base-to-base distance of 0.34 nm, in B-form duplex), about 2.5 bp of dsDNA is needed for each by of split (0.43×2/0.34=~2.5). For DNA/RNA hybrid (base-to-base distance is ~0.30 nm, in B'-form duplex), there is a 2.9 bp per split ratio (0.43×2/0.30=~2.9).

f) Catalytic/Autocatalytic Schemes Possibly Using Multiple saRNAi Species

In certain embodiments, the target for the subject constructs may be the subject signal activated polynucleotide constructs. For example, a feed-back mechanism may be employed in the subject constructs, in that the activated saRNA targets the signal activated polynucleotide construct itself (possibly in addition to knocking down a target mRNA). Similarly, in other embodiments, the target may be one or more different saRNA constructs (optionally, in addition to targeting one or more target mRNAs). In a related embodiment, the invention provide a cascade of siRNAs with different target sequences by taking advantage of the ability of the subject saRNA constructs to cleave other saRNA constructs. The enables the creation of a complex chemical reaction network involving multiple saRNA species that can act on one another or themselves catalytically or auto-catalytically.

Such catalytic/autocatalytic schemes are most useful where the concentration of the signal to be detected is very low (e.g., unspliced HIV transcripts in cell nuclei), or where the signal to be detected is partially unknown or is mutating frequently (e.g., oncogenes/viral transcripts etc.). In these cases, multiple saRNA constructs can be used to detect different sections of the same transcript, and the activation of one saRNA construct can be engineered to lead to the activation of all related saRNA constructs. Such schemes may also be useful in situations where a given siRNA is to be released (e.g., to kill a target cell) whenever one or more active oncogenes are detected.

g) Endogenous Ligand-Stabilized saRNAi

In certain embodiments, the subject signal activated polynucleotide constructs may be stabilized in its inactive form by one or more endogenous ligands, which ligand is preferably present intracellularly at a high concentration. The ligand may associate with different portions of the subject saRNA construct to stabilize the inactive conformation. The construct can be switched to the active state when ligand binding is disrupted.

In certain embodiments, the ligand may bind near the Dicer cleavage site on the guide sequence/sense sequence duplex. In certain embodiments, part of the aptamer is at the Dicer cleavage site itself, and the ligand binding disrupts Dicer cleavage at that site. See exemplary illustration in FIG. 30, panels A-D.

In certain embodiments, the ligand may bind at a site away from the Dicer cleavage site per se, but energetically stabilizes the inactive conformation. Such site may include aptamers within the first and the second additional duplex regions formed between the signal detection sequence/blocking sequence and part of the guide sequence/sense sequence (see FIG. 30, panels A-D). Such site may also include a junction region connected to two or more hairpin structures, each can bind and sense the presence of one or more input signals (polynucleotide, small molecule, etc.). See FIG. 30, panels A-D.

The ligands can be proteins or small molecules that recognize a certain sequence of double stranded or single stranded nucleotides. Preferably, the ligands bind aptamers. Preferred ligands include many different chemical species that are normally at a high concentration inside the cell, for example, metabolites suet as ATP, TPP, nucleotides, coenzymes (see Soukup and Soukup, *Current Opinions in Structural Biology* 14: 344, 2004), non coding RNA (ncRNA), most significantly, tRNA, individual amino acids or protein subdomains such as L-arginine (see Nucleic Acids Research Vol 24, Issue 6, 1029-1036).

In an illustrative embodiment, such ligand-stabilized saRNA may be activated by using a "rip-loop" (supra) to distort or otherwise disable the aptamer site (see FIG. 31, panels A-D). This can be achieved by, for example, using strand-displacement mechanism to disrupt a stem important for the integrity or function of the aptamer site. By taking advantage of sequence overlaps, the signal polynucleotide may cover a part of the aptamer, or part of the "rip-loop," or any linker between the rip-loop and the aptamer, or a combination thereof.

The ligands may be present in high enough levels inside the cell under normal conditions, and aptamers may bind them with sufficiently high equilibrium constants. In the absence of the signal polynucleotides, the saRNA structure is highly likely (~90% or more) to be in the inactive state. Thus, in certain embodiments, the saRNA should be at least 50% less effective than the activated construct in the absence of the signal polynucleotide.

h) Direct RISC-Loading saRNAi

In certain embodiments, the subject signal activated polynucleotide constructs may be loaded directly into RISC and become function, without the need to be first cleaved by Dicer or RNase III. Such construction optionally may be cleaved by certain endo- or exonucleases, such as ribozyme (such as allosteric cis-acting ribozyme, RNase H, or miRNA/siRNA mediated cleavage of the inactive conformation, etc.).

FIG. 27, panels A-I, shows some exemplary embodiments where certain constructs may or may not be productively loaded into RISC. As described herein above, some chemical modifications may inhibit RISC loading from the 5' and/or the 3' ends. For example, certain 3' end modification will inhibit loading of an siRNA-like duplex into RISC, if the 3' end of the guide strand is changed to DNA bases. On the other hand, if the first 8 base pairs on the 5' end of the guide strand are entirely modified to DNA, the siRNA remains effect (supra). In another example, inter-strand crosslinking of the guide and sense sequences using halogen or psorelin bases will also stop RISC loading. See the "INACTIVE" panels.

However, such RISC loading information can also be used to design some embodiments of the saRNA that can be activated in the presence of the signal polynucleotides.

Thus in certain embodiments, such as in the so-called keyhead or telescoping design shown in FIG. 29, panels A-C, the 5' end of the guide sequence is directly 3' to a first stretch of RNA sequence that (1) comprises a 5' end RISC loading blocking modification (supra), and (2) hybridizes with the signal detection sequence. The 3' end of the sense sequence is directly 5' to a second stretch of DNA. Wherein the signal detection sequence comprises an RNA region that hybridize with the first stretch of RNA sequence and a DNA region that hybridize with the second stretch of DNA. Optionally, the second stretch of DNA is linked to the DNA region on the signal detection sequence via a single-stranded loop. Upon signal sequence binding, the signal detection sequence is displaced, allowing the first stretch of RNA sequence and the second stretch of DNA to form an extended duplex region. This extended DNA/RNA hybrid can be cleaved by RNase H to expose the 5'-end phosphorylated guide sequence, which can then be loaded into RISC without Dicer cleavage. The 5' end of the first stretch of RNA sequence may be protected by a 5'-RISC loading complex blocking modification (supra). The signal polynucleotide, especially at the regions hybridizing with the DNA segments, may be cleaved by RNase H.

In certain embodiments, such as in the so-called chimera-masking design shown in FIG. 29, panels A-C, the signal detection sequence may comprise a Dicer-resistant RNA polynucleotide (the middle portion) that hybridizes with parts of the guide sequence and forms a duplex region, which duplex region contains a 3' chemical group that interferes with RISC loading. The signal detection sequence also comprises two single-stranded DNA segments flanking the middle RNA portion, one of which is linked to the 5'-end of the 21-nt sense sequence. Upon hybridization by a signal polynucleotide, such as an mRNA, the signal stranded DNA regions flanking the Dicer-resistant middle RNA sequence form DNA/RNA hybrids with the signal polynucleotide, and eventually directs the degradation of the signal polynucleotides by RNaseH. Meanwhile, an extended duplex regions (e.g., about 21 bp in length) is formed between the guide and the sense sequences. Due to the presence of the DNA segment directly 5' to the sense sequence, RNaseH also degrades the RNA comprising the 3' chemical groups linked to the guide sequence, thus allowing the resulting 21-nt guide sequence to be directly incorporated into RISC without having to be first cleaved by Dicer.

In another embodiment, as shown in FIG. 26, panels A-D, the 5' end of the guide sequence is linked to a signal detection sequence comprising one or more signal activated cleavage sites (supra). Optionally, the 5' end of the guide sequence and/or the 3' end of the sense sequence comprise one or more (up to 8) nuclease-resistant bases. Optionally, the 5' end of the sense sequence comprises a 5' RISC loading complex blocking group (supra). Upon signal binding to the signal detection sequence, the signal activated cleavage site is cleaved (e.g., via RNaseH, Ago2, cis-acting ribozyme, or any other means described herein above), exposing sites that are susceptible to 5' exonuclease activity. Degradation by one or more exo- or endo-nucleases of the signal detection sequence eventually will stop at the nuclease resistant bases at the 5' end of the guide sequence, leading to the creation of a siRNA-like construct, with the 5'-phosphorylation generated by the exonucleases.

Alternatively, the 5' end of the 21-nt guide sequence may be blocked by a sense-strand-associated 5' binding aptamer or blocking ligand. RISC loading of the guide sequence cannot proceed unless such 5' binding aptamer or blocking ligand is removed. The signal detection sequence may comprise a signal activated cleavage site, and is linked to the 5' end of the sense sequence. Upon signal binding to the signal detection sequence, the signal activated cleavage site is cleaved (e.g., via RNaseH, Ago2, cis-acting ribozyme, or any other means described herein above), exposing sites that are susceptible to 5' exonuclease activity. Alternatively, upon signal binding to the signal detection sequence, a rip-loop like mechanism may disrupt the structure of the 5' binding aptamer or blocking ligand, leading to the exposure of the guide sequence 5' end with phosphorylation. The guide sequence can subsequently be loaded into RISC without first going through Dicer cleavage.

In certain embodiments, multiple inhibition mechanisms may be used on the same construct to create a logic gate for multiple inputs. For example, an inhibitory 3' modification (such as a Fluorescine dye) and an inhibitory 5' group (such as an inverted-dT base) may be added to the 3' end and the 5' end, respectively, of a guide strand. Optionally, on the 3' end of the sense sequence, another blocking group (such as another fluorescine dye) may be added to further interfere with the binding to the 5' end of the guide strand by the RISC loading complex (RLC). Using mechanisms described above, such a construct may be activated by cleaving off the 3' and 5' ends of the guide strand and the 3' end of the passenger strand using different input signals, leading to an AND gate with 3 inputs. Such constructs can be especially useful, for example, when it is desirable to integrate several different miRNA or small molecule signals.

i) Pri-miRNA Tail

Recent studies (see McBride et al., PNAS 105: 5868, 2008) show that transcription of constructs with pri-miRNA conformation is less toxic than directly transcribing shRNAs. Thus in certain embodiments, the subject saRNAs may comprise a tail form that resembles a pri-miRNA (see, for example, FIG. 25). Specifically, the saRNA construct may comprise a microprocessor domain, which is directly linked to the guide sequence and the sense sequence. After importation of such a construct into the nucleus, the Microprocess/Drosha complex cleaves the construct to its tail-less saRNA form. The 5'end of the microprocessor domain may be capped, while its 3' end may comprise a poly-A sequence.

The subject constructs having the pre-miRNA tail may have reduced toxicity compared to unmodified corresponding saRNA.

j) Computational/Automated Design of saRNAi

Computer algorithms may be used to automate the design of the subject saRNA constructs.

III. Applications of Signal-Activated RNAi Technology

The invention now being generally described, it will be more readily understood by reference to the following uses. These uses and applications of signal-activated RNAi technology are included merely for purposes of illustration of certain aspects and embodiments of the present invention, and are not intended to limit the invention.

a) Signal-Activated RNAi in Cancer

The presence of mutated mRNA sequences, changes in the levels of certain miRNAs, the presence of normally dormant transcription factors and or other changes in the transcriptome are associated with all cancers. Studies have shown that patterns in the expression of mutated mRNAs, normally dormant developmental factors, and the level of miRNA expression could be further correlated with the likelihood of metastasis in some cancers. Signal-activated RNAi allows the delivery of small RNA structures using existing or future methods for siRNA delivery to cancer cells. Upon entry into the cytoplasm, the structures detect the presence of various cancer markers or signals in the transcriptome and initiate RNA interference.

In traditional RNA interference, the target gene must be a gene that cancer cells depend on to a degree more than healthy cell, or a gene that has a mutated sequence in cancer. One example is a mutated K-RAS mRNA. This allows RNAi therapy to interfere with the growth and development of cancer cells but may not allow RNAi to directly repress genes critical to the cancer cell's survival. In contrast, signal-activated RNAi can detect the transcriptome cancer markers and activate to induce RNAi against critical cellular processes, thereby directly inducing apoptosis, inflammatory responses, or other responses that more directly destroy the cancer cell. Furthermore, since signal-activated RNAi is only active inside cancer cells, we can deliver a much higher dose of therapeutic RNA structures using methods such as nanoparticle transfection through the Enhanced Uptake and Retention effect without causing harm to organs where nanoparticles or other delivery structures tend to accumulate. Overall, these advantages could lead to dramatically increased and more selective lethality against cancer cells.

Several genes are likely candidates for signal polynucleotides. Examples comprise targetable cancer markers, such as K-RAS, mutations of which have been associated with pancreatic, breast, and lung cancers; fusion oncogenes; viral RNAs corresponding to viruses that may induce sarcomas; miRNAs that are reported to be upregulated in solid tumors (see Volinia et al, *PNAS*, 103, 2257; Ma et al, *Nature*, 449, 682; He et al, *Nature*, 435, 828), such as the mir-17-92 cluster, mir-10a, mir-21, and more.

Novel small and microRNA targets in human cancers given in the following papers have been described in recent publications. Unique targets may be found for human cervical cancer (Liu, Pourmand, Patterson, and Fire, *Cancer Res*, 67, 6031 (2007)), chronic lymphocytic leukemia (Borkhardt, Arndt, Fuchs, Uta, and Tuschl, Tom, *The New England Journal of Medicine*, 354, 524 (2006) and Calin et al, *The New England Journal of Medicine*, 353, 1703 (2005)).

Developmental transcriptional factors such as Twist may be targeted by signal-activated RNAi. Data from a recent study (*Cell*, 117, 927 (2004)) suggests that developmental transcription factors are reactivated in metastatic cancer cells. Twist and other developmental transcription factors may be expressed in normal cells of one body organ but only in cancer cells of another body organ. Thus, they are cancer indicators only in certain types of human cells. In some embodiments, RNAi may use an n-AND gate switching mechanism that determines the cell type and the presence of abnormal developmental factors before activating RNAi.

In addition, through the use of n-AND gates that recognize several transcriptome markers, signal-activated RNAi may be used to target cancer cells that exhibit phenotypes consistent with the cancer stem cell hypothesis. Several lines of evidence support the cancer stem cell hypothesis in myeloid leukemia (Bonnet D and Dick J E. *Nat Med* 3:730-7(1997)), breast cancer cells (Al-Hajj et al. *Proc Natl Acad Sci USA* 100(7):3983-8(2003)), human brain tumors (Singh S K, Clarke I D, Terasaki M, Bonn V E, Hawkins C, Squire J, Dirks P B. *Cancer Res.* 63:5821-8 (2003)) and colon cancer (O'Brien C A, Pollett A, Gallinger S, Dick J E. "A human colon cancer cell capable of initiating tumor growth in immuno-deficient mice." *Nature.* 445:106-10 (2007)).

Exemplary target genes are described below.

BCL-1 (Entrez GeneID: 595) encodes the Cyclin D1 protein, which acts to control G1 progression and G1/S transition. Cyclin D1 forms a complex with and functions as a regulatory subunit of CDK4 or CDK6, whose activity is required for cell cycle G1/S transition. This protein has been shown to interact with tumor suppressor protein Rb and the expression of this gene is regulated positively by Rb. Mutations, amplification and overexpression of this gene, which alters cell cycle progression, are observed frequently in a variety of tumors and may contribute to tumorigenesis. Overexpression of the bcl-I gene has been found in lymphoma, leukemia, and myeloma, where it may act to accelerate the cell transit through the G1 phase of the cell cycle. Accordingly, bcl-1/Cyclin DI may be used for signal-activated RNAi. As a target, bcl-1/Cyclin D1 knockdown may provide a means for controlling unchecked cell growth. As a signal polynucleotide, bcl-1 gene products may be used to target other RNAi pathways against genes during the specific time point that bcl-1 is expressed.

NADPH oxidase 4 (Nox4, Entrez Gene ID 50507) has been postulated to function in the kidney as an oxygen sensor that regulates the synthesis of erythropoietin (EPO) in the renal cortex. The gene has also been associated with pancreatic cancer, so signal-activated RNAi directed against this target could be a particularly useful therapy against pancreatic cancer, as well as other types of cancer or any other disorders associated with dysregulation of reactive oxidative species (ROS).

Mammalian lin-28 (Entrez GeneID: 79727) is a homolog of the *C. elegans* lin-28. In humans, lin-28 has been implicated in tumor metastasis and invasion. Low levels of Lin-28 expression are present in the other organs, but high expression may also appear selectively in tumors. Regulation of mRNA is a conserved feature of the lin-28 gene in diverse animals. The long isoform of Lin-28-B is a specific inhibitor of let-7 mRNA and Lin-28 downregulation by miR-125 involves a reduction in both translational efficiency and mRNA abundance. Therefore, modulation (e.g., inhibition) of Lin-28 expression may be used to inhibit cancer invasion and metastasis.

Pancreatic stellate cells (PaSCs) are used to repair injury in the pancreas. Examples of injury include long-term activation by oxidative stress and repetitive injury that leads, in turn, to fibrosis. In other capacities, PaSCs may aid in tumor growth and invasion of surrounding tissue. Thus, modulating the function of PaSCs may useful for inhibiting tumor growth and invasion, or controlling repair of injured tissue. General features of PaSCs in the quiescent and activate state have been characterized and compared. Notably, expression of the molecular marker a-SMA is higher in activated PaSCs than in quiescent PaSCs. Thus, α-SMA could be used as a signal to target the polynucleotides described herein to activate PaSCs.

Heat shock transcription factor 1 (HSF1, Entrez Gene ID 3297) is a heat shock transcription factor that is induced after temperature stress. HSF1 up-regulates chaperone machinery in response to cellular stress, and may play a role in cancer and neurodegeneration. In recent studies, HSF1 knockdown was shown to be selectively lethal towards cancer cells, while other studies suggest that generalized knockdown of HSF1 could lead to side effects including exacerbation of neurodegeneration. HSFI could be a target for signal-activated RNAi, or may be useful as a signal that will activate RNAi in select cells.

Bcl-2 (Entrez GeneID 596) and the Bcl family of proteins govern mitochondrial outer membrane permeabilization and are either pro-apoptotic or anti-apoptotic. Mutations in a variety of Bcl proteins have been associated with pathological conditions, including cancer. Thus, where Bcl proteins act to inhibit apoptosis, knockdown of gene or protein function is expected to induce apoptosis. Bcl-2 or other Bcl family members could serve as gene targets, or, alternately, mutant forms of the proteins could serve as signals for diseased cells or cells that are susceptible to deficits.

The target sequence need not be identical to the signal polynucleotide. In one design, the signal-activated polynucleotide is designed to hybridize to α-SMA mRNA, which displaces a duplexes formed between the signal-detecting strand and other sequences, and enables or promotes formation of a duplex between the guide sequence and the sense sequence. This duplex may be cleaved by Dicer or loaded into RISC. In this example, the guide strand comprises 21 nucleotides directed against RelA (also known as p65, Entrez GeneID 5970). RelA(p65) is a member of the NF-κB family of transcription factors, which are contribute to such cellular processes as the immune response, cell proliferation, cell differentiation. Constitutive activation of proteins from this family have been associated with many pathological conditions such as rheumatoid arthritis, inflammatory bowel syndrome, AIDS and cancer. RNAi-mediated knockdown of RelA(p65) or other NF-κB family members may be useful for treating these conditions. More specifically, the use of a-SMA as a signal polynucleotide directs the knockdown of RelA(p65) to α-SMA expressing cells.

ABCB5 (Entrez GeneID 340273) is expressed in melanocytes and a minority of melanoma cells, but recent evidence suggests that ABCB5 is a likely presence in all melanoma may be play a role in all melanoma metastasis activity. ABCB5 may be a target for signal-activated RNAi in diseases such as cancer and melanoma. As ABCB5 may be involved in multiple-drug resistance, and traditional chemotherapy regimens could enrich ABCB5+ cells, or mAb to ABCB5 may cause unwanted immune response against melanocytes. Thus, local delivery of signal-activated RNAi may be the safest treatment.

DNM3 TB proteins are expressed in a variety of cancers, including myeloid leukemia, lymphoid leukemia, follicular lymphoma, breast cancer, cervical cancer, mesothelioma, head and neck cancer, small cell lung cancer, colorectal cancer, gastric cancer, hepatocellular carcinoma, glioma, primary lymphoid leukemias, primary lymphoblastic leukemias, and more. These proteins are not necessarily present in normal tissue, and the genes encoding the proteins have novel intron sequences. Thus, DNM3 TB gene products may be useful for signal-activated RNAi, either as the signal polynucleotide that activates the RNAi pathway, or as a target for RNAi.

The secretin receptor (pp32, Entrez GeneID 6344) may be involved in cancer. In both pancreatic and liver tumors, a novel mRNA splice-form created by deletion of exon 3 and 4 has been observed. Either pp32 (Entrez GeneID 6343) or its receptor could be targets for signal-activated RNAi. pp32, which normally acts as a tumor suppressor, is located on chromosome 15, whereas pp32r1 and pp32r2 are tumorigenic and are located on chromosomes 4 and 12.

b) Signal-Activated RNAi in Viral Infection

A number of viruses utilize RNA interference at crucial stages in their life cycle or lack mechanisms for completely disabling the cellular RNA interference pathways. Signal-activated RNAi could be used to target crucial viral replication pathways to halt replication, critical cellular processes to induce apoptosis or inflammatory responses, or drug resistance pathways to increase the effectiveness of antiviral therapies. Targets for signal-activated RNAi may comprise viral RNA. For example, signal-activated RNAi may be used to detect HIV associated mRNAs, miRNAs and latency transcripts in latent HIV infected cells.

As reviewed in Cullen, B. R. (2006) Viruses and micro-RNAs. Nature Genetics 38: S25-S30, several viruses have been shown to encode miRNA. Subsequently, RNAi could be used to induce apoptosis of infected cells. In another example, signal-activated RNAi could be activated by herpes latency-associated transcripts. For example, nuclear import signals may be used to bring the signal-activated polynucleotide to the nucleus, where RNA from the herpes virus serves as a signal to activate the polynucleotide.

In addition, latent HIV CD4+ cells show abundance of aborted mRNA transcripts, any of which may serve either as signal polynucleotides or as targets for signal-activated RNAi. Further, there is a high population of HIV DNA in viral reservoirs in the gut.

c) Signal-Activated RNAi in Autoimmune Disease

In some embodiments, signal-activated RNAi may be used to detect transcriptome markers of autoimmune disease. Moreover, signal-activated RNAi may be used to induce senescence in the immune system cells involved in systematic and effective attacks on the body's own cells.

d) Specific Gene/Disease Targets

Signal-activated technology platforms may be useful in antimicrobial applications. For example, signal-activated polynucleotides may be used against *mycobacterium tuberculosis* (TB). TB uses secreted factors to alter the early phagosome of the host macrophage, creating a hospitable environment for replication and potentially for a latent infection (LTBI). Subsequently, enveloped TB bacteria secrete additional factors to block fusion of the phagosome with lysosomes, which normally forms a phagolysosome. TB secreted factors include protein kinases such as PknG, found in the macrophage cytoplasm, secretory protein ESAT-6, CFP-10, and SapM which has PI3P phosphatase activity and interacts with PI3P on the cytoplasmic leaflet of the phagosome. To counteract the effects of the secreted factors, a signal-activated polynucleotide may be used. Degradation-based signal-activated polynucleotide constructs, such as ribozyme aptamers, may be transfected into liver cells. In one embodiment, the ribozyme aptamer binds to a target on PknG (or any other secreted factor) and induces activation through conformational changes and degradation of sequences on the signal-activated polynucleotide. This activity induces apoptosis by production of caspases with signal-activated IRES sequences, or by RNAi-mediated downregulation of pro-apoptotic proteins. Bcl-2 is one potential target. Apoptosis of infected cells subverts necrosis and kills the bacteria.

Signal-activated polynucleotides may also be used to combat infection by the malaria parasite. The sporozoites or hypnozoites establish or maintain an infection by secreting proteins into a parasitophorous vacuolar membrane (PVM). Proteins incorporated into the PVM membrane can be displayed in the host's cytoplasm. UIS3 and UIS4 are two examples of transmembrane proteins that may be used. Parasites such as P. vivax and P. ovale can produce hypnozoites in liver cells, causing a liver infection that can become active months or years later. As a defense, signal-activated polynucleotides, designed as degradation-based platforms are transfected into liver cells. Ribozyme aptamers built in the signal-activated polynucleotides binds to the cytoplasmic side of UIS3 or UIS4 proteins in the PVM transmembrane. This binding activates the signal-activated polynucleotide via a degradation mechanism, through conformational changes and degradation of sequences on the signal-activated polynucleotide. This activity induces apoptosis by production of caspases with signal-activated IRES sequences, or by RNAi-mediated downregulation of pro-apoptotic proteins. Bcl-2 is one potential target. Apoptosis of infected cells subverts necrosis and kills the parasites.

Signal-activated apoptosis or labeling of selected cells may be used to purify or enrich stem cells or transformed cells. A signal-activated polynucleotide may be any RNAi, signal-activated IRES, signal-activated ribozyme, signal-activated antisense molecule, or other embodiments described in the specification. A chosen signal-activated platform is transfected by methods known in the art into a culture of stem cells and/or transformed cells. One or more targets may be found in a cell and one or more signals may also be required for activation of the signal-activated polynucleotide constructs. The targets may distinguish specific cells from others, so that a specific cell type may be purified. For example, the target can trigger production of fluorescent markers which can be used to sort cells by FACS. Targets can be disease signals such as activated oncogenes or viral gene products. Alternately, targets can be endogenous mRNAs or other endogenous molecules that should only be expressed in properly transformed cells, such as induced pluripotent stem cells (IPS), or transcription factors or tissue specific factors that can be used for separating differentiated stem cells, or factors specific to a cell-cycle phase. Types of cells isolated may comprise primitive quiescent cells or differentiated stem cells, which can be silenced by polycomb group proteins in stem cells. The following functions can be induced in a cell after activation of a signal-activated polynucleotide: apoptosis, production of a specific marker, RNAi knockdown of endogenous surface receptors or surface-receptor subunits. Either constitutively-expressed proteins or new or transiently expressed surface receptors may be targeted. In the case where transformed cells are to be isolated, targets or signals could comprise newly-expressed or transiently-expressed factors. In other cases, it is desirable to induce apoptosis of cells wherein disease or viral markers are present. It is also possible to run multiple rounds of transfection of signal-activated polynucleotides, followed by purification, and cell-culture of transfected cells. This iterative process will enrich for a population of cells carrying the desired phenotype.

Diseased cells may be targeted by signal-activated polynucleotides, provided that diseased cells can be distinguished from non-diseased cells. In some embodiments, diseased cells can be distinguished by overexpression of endogenous receptors, or by expression of disease-specific receptors. In epithelial cancer cells, the folate receptor is overexpressed, while in HIV-infected cells, the HIV-1 glycoprotein Env is expressed. In other embodiments, diseased cells can be distinguished by changes in the intercellular serum pH. For example, elevated pH in local extracellular environment may signal disease. In tumors, heterogeneous perfusion impairs removal of acidic metabolic waste and requires cells to have higher levels of anaerobic glycolysis. In other embodiments, properties of intracellular proteins may indicate that a cell is diseased. Virus or cancer proteins may be misfolded, or protein expression levels may change. In cancerous cells, high levels of thymidylate synthase (TS) are indicative of malignancy and correlate with poor survival rates in patients. TS is also expressed at elevated levels in cells that have been transformed with tumor viruses. Finally, irregular morphologies of cells or cellular structures often correlate with disease. Irregular chromatin distribution in the nucleus, an increased nucleus to cytoplasm (N:C) ratio, and other atypical morphologies may signal cell malignancy.

e) Cell Lines, Plant, and Animal Models with Multiple Dormant Signal-Activated RNAi Transcripts Signal-activated polynucleotides may be incorporated into cell lines or into multicellular organisms. This scheme enables selective, correlated activation of RNAi against one or more targets, based on specific predetermined signals. In some embodiments, one or more signal-activated polynucleotides may be used as a transgene in cell lines or in multicellular organisms. Activation of transgenic signal-activated polynucleotides may be mediated by specific signals in the cells or by molecules administered to the cells. One or more signal-activated polynucleotide may be expressed in any given cell.

In some embodiments, one or more signal-activated polynucleotides may be used in combination with transgenic plants and animals, wherein signals in the transgenic organism activate the signal-activated polynucleotides. In one embodiment, the transgene or some product of a signaling pathway modulated by the transgene is used to activate a signal-activated polynucleotide.

f) Inhibition of Special Cap Structure Recognition by Cellular Defense Proteins

Techniques in which phage or bacterial polymerases are used for plasmid transcription inside the cytoplasm can often lead to the presence of a special cap on the 5' end of product mRNAs. For example, T7 phage RNA polymerase produces a 5' tri-phosphate cap on mRNA. In some embodiments, pseudoknot motifs on signal-activated polynucleotides can be used to sequester these structures by using internal ribosome entry site (IRES) structures such as the HCV IRES to initiate translation. This is partly because complex tertiary structures of ribozymes and aptamers (such as the Internal Ribosome Entry Sites of viruses) can conceal the cap from protein recognition. This embodiment avoids problems with activation of cellular defenses and inflammation signals.

g) SNP Discrimination Schemes

Discrimination of single nucleotide polymorphisms is difficult because of the small difference in the free energy of binding between two oligonucleotides that vary by only a single base. In some embodiments, a strand displacement type probe is used to interrogate the SNP region. Strand displacement is a process that is kinetically inhibited by SNP presence near the toehold for the start of the reaction. The kinetic trapping effect is used as the first screen. The bound SNP section provides a viable substrate for dicer cleavage. The SNP is placed near the dicer cleavage site to allow a single base mismatch to inhibit cleavage. In some embodiments, flanking mismatches or chemically modified bases can also be added near the SNP to further enhance cleavage inhibition by single base mismatch and inhibit cleavage of the target substrate (since Dicer cleaves both strands in a duplex). Cleavage of the probe strand upon binding to the correct SNP releases a signal strand.

In other embodiments, Dicer cleavage of a SNP-incorporating duplex segment is formed by a strand displacement-type probe. Here, the signal strand may incorporated into the resulting siRNA like motif with the SNP at the scission site expected for the RISC complex. A single base mismatch at this position could significantly inhibit scission of the 'passenger' strand, thereby inhibiting the maturation of the RISC complex (see Leuschner, Ameres, Kueng, and Martinez, *European Mal. Biol. Org. Reports*, 7, 314 (2006)). The resulting RISC complex may be used as a signal for switching of saRNAi.

In some embodiments, the active form of a signal-activated polynucleotide recognizes and targets mRNA with a specific SNP. The polynucleotide comprises a signal detecting sequence at the 5' end of the molecule, followed by sequence that is complementary to the mRNA target, including the SNP. Flanking the sequence that is complementary to the SNP are modified bases. The signal-activated polynucleotide forms a stem-loop structure with an additional strand of nucleotides called a protecting strand. The protecting strand is not continuous with the signal-activated polynucleotide. Binding of a signal polynucleotide to the signal-detecting sequence on the signal-activated polynucleotide causes a conformational change in the signal-activated polynucleotide, such that the protecting strand dissociates and the signal-activated polynucleotide binds to the target. The duplex formed between the target mRNA and the signal-activated polynucleotide is designed such that the Dicer cleavage site is located at the site of the SNP. Only if the SNP has paired to its suitable complement will the duplex be cleaved by Dicer. This way, only the target mRNA with the SNP that complements the signal-activated polynucleotide will be degraded.

In a similar variation, the signal-activated polynucleotide is a double stranded duplex comprising a first sequence that includes the SNP and a protecting strand that is base paired to the first sequence. When the signal-activated polynucleotide binds to the target mRNA, the SNP is positioned such that it is 9 nucleotides from the 3' end of the duplex. This is the predicted cleavage position, and only the correct pairing of SNP and its complement will result in cleavage by Dicer and processing by the RISC complex. Thus, only the target mRNA that contains a SNP complementary to the signal-activated polynucleotide will be degraded.

h) Protection of Small Antisense RNA Oligonucleotides

The 5' or 3' ends of small antisense oligonucleotides may be reversibly sequestered when a combination of inactivation mechanisms is used along with switching mechanisms. In some embodiments, the sequestered 5' and 3' ends can be used to inhibit degradation by exonucleases, thereby controlling the stability of and concentration of the oligonucleotide in vivo. For example, the 5' or 3' ends in duplexes or in tertiary structures may be hidden such that Xrn 1 and other nuclease will not have a sufficiently long lead sequence with which to start degrading the ends.

IV. Synthesis

The signal activated polynucleotide constructs of the invention or parts thereof can be synthesized by any method known in the art, e.g., using enzymatic synthesis and/or chemical synthesis. The polynucleotide constructs can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J Am. Chem. Soc.* 106:6077; Stec et al. 1985. *J Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26: 1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

V. Delivery/Carrier a) Uptake of Polynucleotide Constructs by Cells

The subject polynucleotide constructs are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the polynucleotide constructs of the invention are contacted with human cells.

Polynucleotide constructs of the invention can be contacted with cells in vitro, e.g., in a test tube or culture dish, (and may or may not be introduced into a subject) or in vivo, e.g., in a subject such as a mammalian subject. The polynucleotide constructs are taken up by cells at a slow rate by endocytosis, but endocytosed polynucleotide constructs are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of the subject polynucleotide constructs into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91116024; WO 91117424; U.S. Pat. No. 4,897,355; Bergan et al. 1993. *Nucleic Acids Research.* 21:3567). Enhanced delivery of polynucleotide constructs can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. Proc. Natl. Acad. Sci. 88:4255).

The optimal protocol for uptake of polynucleotide constructs will depend upon a number of factors, the most crucial being the type of cells that are being used. Other factors that are important in uptake include, but are not limited to, the nature and concentration of the polynucleotide constructs, the confluence of the cells, the type of culture the cells are in (e.g., a suspension culture or plated) and the type of media in which the cells are grown.

b) Conjugating Agents

Conjugating agents bind to the polynucleotide constructs in a covalent manner. In one embodiment, polynucleotide constructs can be derivatized or chemically modified by binding to a conjugating agent to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254:129-132). Conjugation of octyl, dodecyl, and octadecyl residues enhances cellular uptake by 3-, 4-, and 10-fold as compared to unmodified oligonucleotides (Vlassov et al., 1994, Biochimica et Biophysica Acta 1197:95-108). Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci. USA* 84:648).

Certain protein carriers can also facilitate cellular uptake of the subject polynucleotide constructs, including, for example, serum albumin, nuclear proteins possessing signals for transport to the nucleus, and viral or bacterial proteins capable of cell membrane penetration. Therefore, protein carriers are useful when associated with or linked to the subject polynucleotide constructs. Accordingly, the present invention provides for derivatization of polynucleotide constructs with groups capable of facilitating cellular uptake, including hydrocarbons and non-polar groups, cholesterol, long chain alcohols (i.e., hexanol), poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes, and steroids. A major advantage of using conjugating agents is to increase the initial membrane interaction that leads to a greater cellular accumulation of the polynucleotide constructs.

In certain embodiments, gamma carboxyglutamic acid residues may be conjugated to the subject polynucleotide constructs to increased their membrane stickiness, and/or to slow clearance and improve general uptake (infra).

Certain conjugating agents that may be used with the instant constructs include those described in WO04048545A2 and US20040204377A 1 (all incorporated herein by their entireties), such as a Tat peptide, a sequence substantially similar to the sequence of SEQ ID NO: 12 of WO04048545A2 and US20040204377A 1, a homeobox (hox) peptide, a MTS, VP22, MPG, at least one dendrimer (such as PAMAM), etc.

Other conjugating agents that may be used with the instant constructs include those described in WO07089607 A2 (incorporated herein), which describes various nanotransporters and delivery complexes for use in delivery of nucleic acid molecules (such as the subject constructs) and/or other pharmaceutical agents in vivo and in vitro. Using such delivery complexes, the subject polynucleotide constructs can be delivered while conjugated or associated with a nanotransporter comprising a core conjugated with at least one functional surface group. The core may be a nanoparticle, such as a dendrimer (e.g., a polylysine dendrimer). The core may also be a nanotube, such as a single walled nanotube or a multi-walled nanotube. The functional surface group is at least one of a lipid, a cell type specific targeting moiety, a fluorescent molecule, and a charge controlling molecule. For example, the targeting moiety may be a tissue-selective peptide. The lipid may be an oleoyl lipid or derivative thereof. Exemplary nanotransporter include NOP-7 or HBOLD.

c) Encapsulating Agents

Encapsulating agents entrap polynucleotide constructs within vesicles. In another embodiment of the invention, polynucleotide constructs may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the polynucleotide constructs, or improve the pharmacokinetic or toxicologic properties thereof.

For example, the polynucleotide constructs of the present invention may also be administered encapsulated in liposomes, pharmaceutical compositions wherein the active ingredient is contained either dispersed or variously present in corpuscles consisting of aqueous concentric layers adherent to lipidic layers. The polynucleotide constructs, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 run to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

d) Complexing Agents

Complexing agents bind to the polynucleotide constructs of the invention by a strong but non-covalent attraction (e.g., an electrostatic, van der Waals, pi-stacking, etc. interaction). In one embodiment, polynucleotide constructs of the invention can be complexed with a complexing agent to increase cellular uptake of polynucleotide constructs. An example of a complexing agent includes cationic lipids. Cationic lipids can be used to deliver polynucleotide constructs to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl$^-$, Br$^-$, I$^-$, F$^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropy 1-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Polynucleotide constructs can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant polynucleotide constructs can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of polynucleotide constructs (Kamata, et al., 1994. *Nucl. Acids. Res.* 22:536). In another embodiment, polynucleotide constructs are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of polynucleotide constructs. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. J Am. Chem. Soc. 114:10646; Zuckermann, R. N., et al. 1992. *Int. J Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. USA.* 93:3176). In one embodiment, a composition for delivering polynucleotide constructs of the invention comprises a number of arginine, lysine, histidine or ornithine residues linked to a lipophilic moiety (see e.g., U.S. Pat. No. 5,777,153).

In another embodiment, a composition for delivering polynucleotide constructs of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, the cells to be contacted with a polynucleotide constructs of the invention are contacted with a mixture comprising the polynucleotide constructs and a mixture comprising a lipid, e.g., one of the lipids or lipid compositions described supra for between about 12 hours to about 24 hours. In another embodiment, the cells to be contacted with an polynucleotide construct composition are contacted with a mixture comprising the polynucleotide construct and a mixture comprising a lipid, e.g., one of the lipids or lipid compositions described supra for between about 1 and about five days. In one embodiment, the cells are contacted with a mixture comprising a lipid and the polynucleotide construct for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and a polynucleotide construct composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, polynucleotide constructs are modified by attaching a peptide sequence that transports the polynucleotide constructs into a cell, referred to herein as a "transporting peptide." In one embodiment, the composition includes an polynucleotide construct which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Polynucleotide constructs can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. J. Neurosci. 16:253), Vives et al. 1997. *J. Biol. Chem.* 272:16010). For example, in one embodiment, polynucleotide constructs bearing an activated thiol group are linked via that thiol group to a cysteine present in a transport peptide (e.g., to the cysteine present in the turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleotide, and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

e) Targeting Agents

The delivery of polynucleotide constructs can also be improved by targeting the polynucleotide constructs to a cellular receptor. The targeting moieties can be conjugated to the polynucleotide constructs or attached to a carrier group (i.e., poly(L-lysine) or liposomes) linked to the polynucleotide constructs. This method is well suited to cells that display specific receptor-mediated endocytosis.

For instance, polynucleotide constructs conjugate to 6-phosphomannosylated proteins are internalized 20-fold more efficiently by cells expressing mannose 6-phosphate specific receptors than free oligonucleotides. The polynucleotide constructs may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197: 95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eukaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target polynucleotide constructs to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

f) Delivery of Signal-Activated Polynucleotides Across the Blood-Brain Barrier and Cell-Specific Targeting without Cell-Specific Delivery Signal-activated RNAi allows cell, organ, or disease specific targeting of RNA interference using non-specific delivery mechanisms. In some embodiments, one or more cells in a multicellular organism may contain a signal-activated polynucleotide, but the signal required to activate the polynucleotide may be present only in a specific population or type of cells. This mechanism may be used to activate RNAi in specific cells in the brain, bypassing the need for cell-specific delivery methods to the brain. Some cell-specific delivery methods do not effectively deliver molecules across the blood-brain barrier, or may not confer the desired levels of specificity. In contrast, individual signal-activated polynucleotides can be engineered to pass through the blood brain barrier where they are activated by one or more specific transcripts inside specific predetermined cells (Kumar et al, *Nature* 448: 39).

VI. Administration

The optimal course of administration or delivery of the polynucleotide constructs may vary depending upon the desired result and/or on the subject to be treated. As used herein "administration" refers to contacting cells with polynucleotide constructs and can be performed in vitro or in vivo. The dosage of polynucleotide constructs may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the polynucleotide constructs in inducing the cleavage of a target RNA can be determined.

Any of the above-described polynucleotide construct compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Polynucleotide constructs may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject polynucleotide constructs with an osmotic pump providing continuous infusion of such polynucleotide constructs, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intra-arterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The polynucleotide constructs of the invention can be formulated in liquid solutions, preferably in physiologically compatible buffers such as Hank's solution or Ringer's solution. In addition, the polynucleotide constructs may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the polynucleotide constructs are formulated into conventional oral administration forms such as capsules, tablets, and tonics. For topical administration, the polynucleotide constructs of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described polynucleotide constructs may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the polynucleotide construct to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the polynucleotide construct at the lymph node. The polynucleotide construct can be modified to diffuse into the cell, or the liposome can directly participate in the delivery of either the unmodified or modified polynucleotide construct into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 μm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and antioxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of polynucleotide constructs are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (M0750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of polynucleotide constructs from the gastrointestinal tract, as well as improve the local cellular uptake of polynucleotide constructs within the gastrointestinal tract, vagina, buccal cavity and other areas of administration.

In an embodiment, the present invention employs various penetration enhancers to affect the efficient delivery of nucleic acids, particularly polynucleotide constructs, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The polynucleotide constructs, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., *Journal of Biomedical Materials Research*, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular polynucleotide construct and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the polynucleotide constructs, the amount of lipid compound that is administered can vary and generally depends upon the amount of the polynucleotide constructs being administered. For example, the weight ratio of lipid compound to polynucleotide construct is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular polynucleotide construct, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the polynucleotide construct is administered in a form in which any toxic effects are outweighed by the therapeutic effects of the polynucleotide construct. In one embodiment, polynucleotide constructs can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of a polynucleotide construct of the present invention is defined as an amount effective, at dosages and for periods of time necessary to achieve the desired result. For example, an active amount of an oligonucleotide may vary according to factors such as the type of cell, the polynucleotide construct used, and for in vivo uses the disease state, age, sex, and weight of the individual, and the ability of the polynucleotide construct to elicit a desired response in the individual. Establishment of therapeutic levels of polynucleotide constructs within the cell is dependent upon the rates of uptake and efflux or degradation. Decreasing the degree of degradation prolongs the intracellular half-life of the polynucleotide construct. Thus, chemically-modified polynucleotide constructs, e.g., with modification of the phosphate backbone, may require different dosing.

The exact dosage of a polynucleotide construct and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regima may be adjusted to provide the optimum therapeutic response. For example, the polynucleotide construct may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject polynucleotide constructs, whether the polynucleotide constructs are to be administered to cells or to subjects.

VII. Assays of Polynucleotide Constructs Stability

Preferably, the subject polynucleotide constructs are stabilized, i.e., substantially resistant to endonuclease and exonuclease degradation. A polynucleotide construct is substantially resistant to nucleases when it is at least about 3-fold more resistant to attack by an endogenous cellular nuclease, and is highly nuclease resistant when it is at least about 6-fold more resistant than a corresponding, single-stranded oligonucleotide. This can be demonstrated by showing that the polynucleotide constructs of the invention are substantially resistant to nucleases using techniques which are known in the art.

One way in which substantial stability can be demonstrated is by showing that the polynucleotide constructs of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol Chem. 266:18162-71; T. Fisher, et al. 1993. Nucleic Acids Research. 21 3857).

The ability of a polynucleotide construct composition of the invention to inhibit protein synthesis can be measured using techniques which are known in the art, for example, by detecting an inhibition in gene transcription or protein synthesis. For example, Nuclease Si mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, polynucleotide construct compositions that do not target a promoter can be identified by fusing a portion of the target nucleic acid molecule with a reporter gene so that the reporter gene is transcribed. By monitoring a change in the expression of the reporter gene in the presence of the polynucleotide construct composition, it is possible to determine the effectiveness of the polynucleotide construct composition in inhibiting the expression of the reporter gene. For example, in one embodiment, an effective polynucleotide construct composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a polynucleotide construct of the invention is measured and compared to a control, e.g., an RNAi molecule typically used in the art (e.g., a duplex oligonucleotide of less than 25 nucleotides in length and comprising 2 nucleotide base overhangs).

We claim:

1. A signal-activatable polynucleotide construct for enzyme-assisted molecular delivery, the construct comprising:
   a targeting domain and
   a sensor domain covalently bound to the targeting domain, the sensor domain comprising:

a signal detection region complementary to at least one signal polynucleotide, a first chimeric sequence comprising at least one RNA region, a second chimeric sequence comprising a DNA region complementary to an RNA region of the at least one RNA regions of the first chimeric sequence, and a masking segment complementary to the first chimeric sequence;

wherein the sensor domain is configured such that:

in absence of the signal polynucleotide, the masking segment hybridizes with the first chimeric sequence, the DNA region of the second chimeric sequence is in a configuration not processable by RNase H, and the signal detection region is presented for binding to the signal polynucleotide; and in presence of the signal polynucleotide, the signal detecting region hybridizes with the signal polynucleotide, the masking segment is displaced from the first chimeric sequence, and the DNA region of the second chimeric sequence hybridizes with the complementary RNA region of the at least RNA region of the first chimeric sequence to provide an RNase H binding site presented for binding to RNase H, and the sensor domain is configured to allow release of the targeting domain from the sensor domain upon cleavage of the RNase H binding site by the RNase H.

2. The signal activatable construct of claim 1, wherein the second chimeric sequence and the targeting domain are located at opposite sides of the first chimeric sequence.

3. The signal activatable construct of claim 1, wherein the inactive conformation the DNA region of the second chimeric sequence hybridizes with an RNA-DNA region of the second chimeric sequence.

4. The signal activatable construct of claim 1, wherein the complementary binding of the at least one signal polynucleotide to the signal detection region results in a duplex polynucleotide having approximately 20 consecutive base pairs.

5. The signal-activated polynucleotide construct of claim 1, wherein the construct comprises one or more 2'-o-methyl modifications that inhibit PKR and/or TLR activation.

6. The signal-activatable polynucleotide construct of claim 1, wherein the signal activatable construct is in a configuration such that at 37° C. in physiological conditions, a form of the signal activatable construct in absence of the signal polynucleotide is at least about 5 kcal/mole, lower in free energy than a form of said signal activatable construct in presence of the signal polynucleotide.

7. The signal-activatable polynucleotide construct of claim 1, comprising two or more single-stranded polynucleotides.

8. The signal-activatable polynucleotide construct of claim 7, wherein nucleotides with chemical modifications, if any, are largely present on one or more said single-stranded polynucleotides.

9. The signal-activatable polynucleotide construct of claim 7, wherein the signal-activatable polynucleotide is not activated in the presence of the signal polynucleotide when one or more said single-stranded polynucleotides are removed from the construct.

10. The signal-activatable polynucleotide construct of claim 7, wherein two or more of said single-stranded polynucleotides are covalently linked by a linker moiety (such as PEG) or a bond other than canonical polynucleotide linkage.

11. The signal-activatable polynucleotide construct of claim 1, configured to have two or more signal polynucleotides bind simultaneously or sequentially to different portions of said signal detection region.

12. The signal-activatable polynucleotide construct of claim 1, wherein the targeting domain comprises a guide sequence and a sense sequence forming a duplex region of no more than 19 base pairs in length.

13. The signal-activatable polynucleotide construct of claim 12, wherein the duplex region comprises one or more chemical modifications that confer resistance to nuclease degradation.

14. The signal-activatable polynucleotide construct of claim 12, wherein in the absence of the signal polynucleotide, the guide sequence and the sense sequence form a double-stranded region comprising one or more chemical modifications that inhibits Dicer cleavage and/or productive RISC incorporation.

15. The signal-activatable polynucleotide construct of claim 12, wherein the guide sequence is substantially complementary to a transcript of a target gene.

16. The signal-activatable polynucleotide construct of claim 1, wherein the targeting domain is configured to interfere with a target intracellular process of the cells through RNAi in presence of the signal polynucleotide.

17. The signal-activatable polynucleotide construct of claim 1, wherein the targeting domain comprises siRNA, microRNA, and/or additional duplex structure is suitable to be used in connection with RNA interfering.

18. The signal-activatable polynucleotide construct of claim 1, wherein in the absence of the signal polynucleotide, generation of the siRNA or miRNA and/or productive incorporation of said siRNA or miRNA into RISC is inhibited by at least about 2-fold, 5-fold, 10-fold, or 20-fold or more.

19. A method to inhibit expression of a target gene, comprising providing an effective amount of the signal-activated polynucleotide construct of claim 1 and the said signal polynucleotide.

20. The method of claim 19, wherein said target gene is within a cell.

21. The method of claim 20, wherein the cell is contacted with the signal-activated polynucleotide construct in vitro.

22. The method of claim 20, wherein the cell is that of a human, a non-human primate, a non-primate mammal, a rodent, a livestock animal, a bird, an insect, a fly, a worm, or a plant.

23. A pharmaceutical composition comprising an effective amount of one or more of the signal-activated polynucleotide construct of claim 1 and a pharmaceutically acceptable amount of excipients, carriers, or diluents.

24. A vector encoding the signal-activated polynucleotide construct of claim 1.

25. A cell comprising the signal-activated polynucleotide construct of claim 1.

* * * * *